United States Patent
Imran

(10) Patent No.: US 8,721,620 B2
(45) Date of Patent: May 13, 2014

(54) SWALLOWABLE DRUG DELIVERY DEVICE AND METHODS OF DRUG DELIVERY

(75) Inventor: Mir Imran, Los Altos Hills, CA (US)

(73) Assignee: Rani Therapeutics, LLC, San Jose, CA (US)

(*) Notice: Subject to any disclaimer, the term of this patent is extended or adjusted under 35 U.S.C. 154(b) by 461 days.

(21) Appl. No.: 12/978,233

(22) Filed: Dec. 23, 2010

(65) Prior Publication Data

US 2011/0160699 A1 Jun. 30, 2011

Related U.S. Application Data

(60) Provisional application No. 61/395,304, filed on May 10, 2010, provisional application No. 61/340,331, filed on Mar. 15, 2010, provisional application No. 61/339,941, filed on Mar. 10, 2010, provisional application No. 61/284,766, filed on Dec. 24, 2009.

(51) Int. Cl.
*A61M 31/00* (2006.01)

(52) U.S. Cl.
USPC .............................. 604/503; 604/60

(58) Field of Classification Search
USPC ......... 604/890.1–892.1, 500–503, 57, 65–67, 604/103.01, 59, 60
See application file for complete search history.

(56) References Cited

U.S. PATENT DOCUMENTS

| | | | |
|---|---|---|---|
| 3,788,322 A | 1/1974 | Micheals | |
| 4,425,117 A | 1/1984 | Hugemann et al. | |
| 4,596,819 A | 6/1986 | Nicolaides et al. | |
| 4,663,308 A | 5/1987 | Saffran et al. | |
| 4,781,685 A | 11/1988 | Lehmann et al. | |
| 5,129,915 A | 7/1992 | Cantenys | |
| 5,137,669 A | 8/1992 | Leonard et al. | |
| 5,217,449 A | 6/1993 | Yuda et al. | |
| 5,271,945 A | 12/1993 | Yoshioka et al. | |
| 5,474,785 A | 12/1995 | Wright et al. | |

(Continued)

FOREIGN PATENT DOCUMENTS

| CN | 101511305 | 8/2009 |
|---|---|---|
| WO | WO 03/068061 A1 | 8/2003 |

(Continued)

OTHER PUBLICATIONS

U.S. Appl. No. 13/532,589, filed Jun. 25, 2012, Imran.

(Continued)

*Primary Examiner* — Bhisma Mehta
*Assistant Examiner* — Bradley Osinski
(74) *Attorney, Agent, or Firm* — Wilson, Sonsini, Goodrich & Rosati

(57) ABSTRACT

Embodiments of the invention provide swallowable devices, preparations and methods for delivering drugs and other therapeutic agents within the GI tract. Some embodiments provide a swallowable device such as a capsule for delivering drugs into the intestinal wall or other GI lumen. The device comprises a capsule sized to be swallowed and pass through the intestinal tract. The capsule can include at least one guide tube, one or more tissue penetrating members positioned in the guide tube, a delivery member, an actuating mechanism and a release element. The release element degrades upon exposure to various conditions in the intestine so as to release and actuate the actuating mechanism. Embodiments of the invention are particularly useful for the delivery of drugs which are poorly absorbed, tolerated and/or degraded within the GI tract.

29 Claims, 45 Drawing Sheets

(56) References Cited

U.S. PATENT DOCUMENTS

| | | | |
|---|---|---|---|
| 5,674,205 | A | 10/1997 | Pasricha et al. |
| 5,683,435 | A | 11/1997 | Truex et al. |
| 5,750,926 | A | 5/1998 | Schulman et al. |
| 5,795,591 | A | 8/1998 | Lee et al. |
| 5,849,327 | A | 12/1998 | Berliner et al. |
| 5,904,935 | A | 5/1999 | Eckenhoff et al. |
| 5,987,358 | A | 11/1999 | Sosebee et al. |
| 6,645,988 | B2 | 11/2003 | Phillips |
| 6,656,155 | B2* | 12/2003 | Freyman ............... 604/103.01 |
| 6,975,906 | B2 | 12/2005 | Rusin et al. |
| 7,083,578 | B2 | 8/2006 | Lewkowicz et al. |
| 7,083,579 | B2 | 8/2006 | Yokoi et al. |
| 7,396,265 | B2 | 7/2008 | Darley et al. |
| 7,502,649 | B2 | 3/2009 | Ben-Haim et al. |
| 7,569,032 | B2 | 8/2009 | Naimark et al. |
| 7,785,291 | B2 | 8/2010 | Marco et al. |
| 7,854,745 | B2 | 12/2010 | Brister et al. |
| 8,353,863 | B2 | 1/2013 | Imran |
| 2002/0198470 | A1 | 12/2002 | Imran et al. |
| 2004/0093039 | A1 | 5/2004 | Schumert |
| 2004/0122315 | A1 | 6/2004 | Krill |
| 2004/0143221 | A1 | 7/2004 | Shadduck |
| 2004/0253304 | A1* | 12/2004 | Gross et al. ............... 424/451 |
| 2004/0267240 | A1 | 12/2004 | Gross et al. |
| 2005/0038415 | A1 | 2/2005 | Rohr et al. |
| 2005/0065463 | A1 | 3/2005 | Tobinaga et al. |
| 2005/0095246 | A1 | 5/2005 | Shafer |
| 2005/0183733 | A1 | 8/2005 | Kawano et al. |
| 2007/0016262 | A1 | 1/2007 | Gross et al. |
| 2007/0066557 | A1 | 3/2007 | Monia et al. |
| 2007/0100378 | A1 | 5/2007 | Maschino |
| 2007/0123809 | A1 | 5/2007 | Weiss et al. |
| 2007/0161851 | A1 | 7/2007 | Takizawa et al. |
| 2007/0265598 | A1* | 11/2007 | Karasik ................ 604/891.1 |
| 2007/0277374 | A1 | 12/2007 | Suaning |
| 2007/0288033 | A1 | 12/2007 | Murature et al. |
| 2008/0065181 | A1 | 3/2008 | Stevenson |
| 2008/0255543 | A1* | 10/2008 | Tanaka et al. ............ 604/891.1 |
| 2008/0275430 | A1 | 11/2008 | Belsky et al. |
| 2009/0004266 | A1 | 1/2009 | Sung et al. |
| 2009/0030473 | A1 | 1/2009 | Khawaled et al. |
| 2009/0041849 | A1 | 2/2009 | New |
| 2009/0088387 | A1 | 4/2009 | Castillo et al. |
| 2009/0093617 | A1 | 4/2009 | Shenoy et al. |
| 2009/0187229 | A1 | 7/2009 | Lavie |
| 2009/0258519 | A1 | 10/2009 | Dilmaghanian et al. |
| 2009/0306633 | A1 | 12/2009 | Trovato et al. |
| 2010/0021536 | A1 | 1/2010 | Gross |
| 2010/0034823 | A1 | 2/2010 | Borhani et al. |
| 2010/0049120 | A1 | 2/2010 | Dijksman et al. |
| 2010/0056948 | A1 | 3/2010 | Hornby et al. |
| 2010/0094256 | A1 | 4/2010 | Kassab et al. |
| 2010/0100117 | A1 | 4/2010 | Brister et al. |
| 2011/0046053 | A1 | 2/2011 | Kidron |
| 2011/0098651 | A1 | 4/2011 | Falo, Jr. et al. |
| 2011/0160129 | A1 | 6/2011 | Imran |
| 2011/0160699 | A1 | 6/2011 | Imran |
| 2011/0208270 | A1 | 8/2011 | Imran et al. |
| 2012/0010590 | A1 | 1/2012 | Imran |

FOREIGN PATENT DOCUMENTS

| | | |
|---|---|---|
| WO | WO 2005/105053 A2 | 11/2005 |
| WO | WO 2006/064502 A2 | 6/2006 |
| WO | WO 2007/093806 A1 | 8/2007 |

OTHER PUBLICATIONS

U.S. Appl. No. 13/538,728, filed Jun. 29, 2012, Imran.
U.S. Appl. No. 13/538,748, filed Jun. 29, 2012, Imran.
U.S. Appl. No. 13/583,770, filed Jun. 29, 2012, Imran.
U.S. Appl. No. 13/538,783, filed Jun. 29, 2012, Imran.
U.S. Appl. No. 13/538,793, filed Jun. 29, 2012, Imran.
U.S. Appl. No. 13/538,812, filed Jun. 29, 2012, Imran.
U.S. Appl. No. 13/538,823 filed Jun. 29, 2012, Imran.
U.S. Appl. No. 13/538,841, filed Jun. 29, 2012, Imran.
U.S. Appl. No. 13/538,852, filed Jun. 29, 2012, Imran.
U.S. Appl. No. 13/538,875, filed Jun. 29, 2012, Imran.
U.S. Appl. No. 13/538,903, filed Jun. 29, 2012, Imran.
U.S. Appl. No. 13/538,912, filed Jun. 29, 2012, Imran.
U.S. Appl. No. 13/539,019, filed Jun. 29, 2012, Imran.
U.S. Appl. No. 13/539,031, filed Jun. 29, 2012, Imran.
International search report dated Sep. 5, 2012 for International Application No. PCT/US2012/045138.
International search report and written opinion dated Sep. 21, 2010 for PCT/US2010/044265.
International search report dated Sep. 23, 2011 for International Application No. PCT/US2010/062070.
International search report dated Sep. 29, 2011 for International Application No. PCT/US2010/062073.
International search report dated Dec. 7, 2012 for International Application No. PCT/US2012/044441.
Office action dated Nov. 7, 2012 for U.S. Appl. No. 12/978,164.
Tao, et al. Gastrointestinal patch systems for oral drug delivery. Drug Discov Today. Jul. 1, 2005;10(13):909-15.
Whitehead, et al. Oral delivery of macromolecules using intestinal patches: applications for insulin delivery. J Control Release. Jul. 23, 2004;98(1):37-45.
U.S. Appl. No. 13/837,025, filed Mar. 15, 2013, Imran.
U.S. Appl. No. 13/970,446, filed Aug. 19, 2013, Imran.
Betancourt, et al. Micro- and nanofabrication methods in nanotechnological medical and pharmaceutical devices. Int J Nanomedicine. 2006;1(4):483-95.
European search report and opinion dated Jul. 26, 2013 for EP Application No. 10840193.6.
Irons, et al. Bioadhesives in Drug Delivery. Taylor and Francis Group, LLC. 2003. Ch 48.
Jain. The manufacturing techniques of various drug loaded biodegradable poly(lactide-co-glycolide) (PLGA) devices. Biomaterials. 2000; 21:2475-2490.
Office action dated Jun. 5, 2013 for U.S. Appl. No. 12/849,574.
Office action dated Jun. 20, 2013 for U.S. Appl. No. 13/538,912.
Office action dated Jul. 8, 2013 for U.S. Appl. No. 13/539,019.
Office action dated Jul. 9, 2013 for U.S. Appl. No. 12/978,164.
Office action dated Jul. 9, 2013 for U.S. Appl. No. 13/538,852.
Office action dated Aug. 26, 2013 for U.S. Appl. No. 13/538,728.
Office action dated Aug. 27, 2013 for U.S. Appl. No. 13/538,770.
Yoncheva, et al. Pegylated nanoparticles based on poly(methyl vinyl ether-co-maleic anhydride): preparation and evaluation of their bioadhesive properties. Eur J Pharm Sci. Apr. 2005;24(5):411-9.
Basic Pharmacokinetics; Chapter 6. www.pharmpress.com/files/docs/php-bph-c06.pdf [online] retrieved on Oct. 25, 2013; 22 pages.
Bauer, et al. Pharmazeutische Technologie. Gustav Fischer Verlag, Germany. Jan. 1, 1997; 337-349. (in German).
European search report and opinion dated Jun. 26, 2013 for EP Application No. 10807036.8.
European search report and opinion dated Oct. 24, 2013 for EP Application No. 10847622.7.
Frandsen, et al. Abrams' Clinical Drug Therapy. 2013 Lippincott Williams & Wilkins. 3 pages.
Office action dated Oct. 29, 2013 for U.S. Appl. No. 13/538,823.
Office action dated Oct. 31, 2013 for U.S. Appl. No. 13/539,031.
Office action dated Nov. 6, 2013 for U.S. Appl. No. 13/970,446.
Roberts, et al. Pharmacokinetics and anaesthesia. (Continuing Education in Anaesthesia, Critical Care & Pain, 2007, vol. 7: 25-29).
U.S. Appl. No. 14/179,215, filed Feb. 12, 2014, Imran et al.
Office action dated Dec. 19, 2013 for U.S. Appl. No. 13/532,589.

* cited by examiner

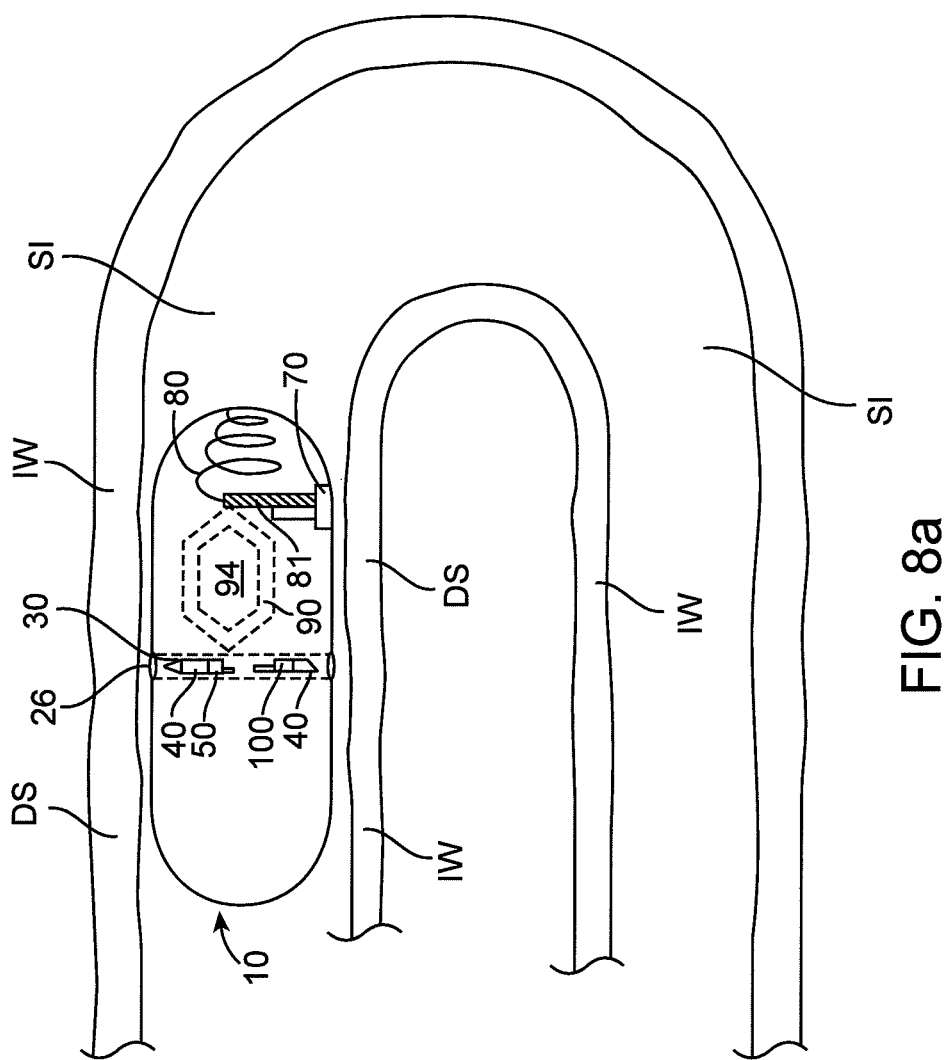

Degradation

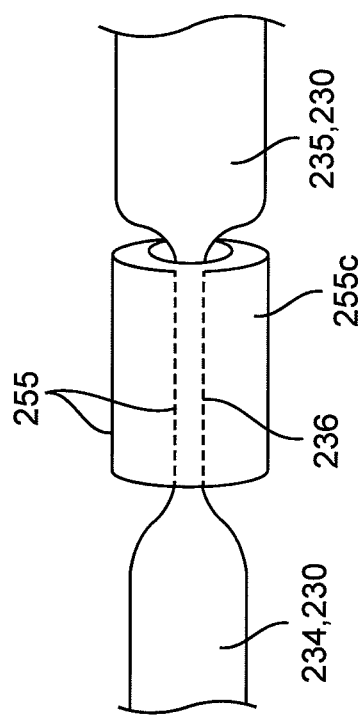

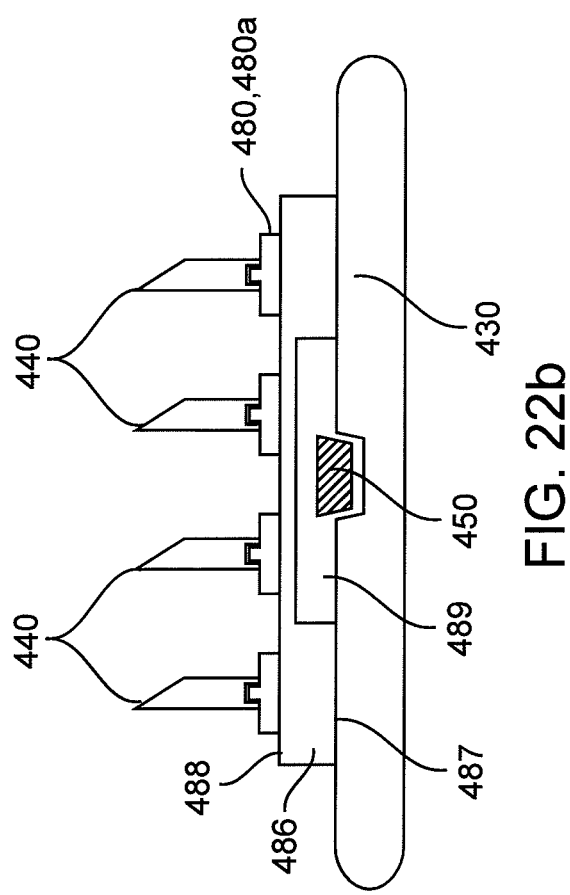

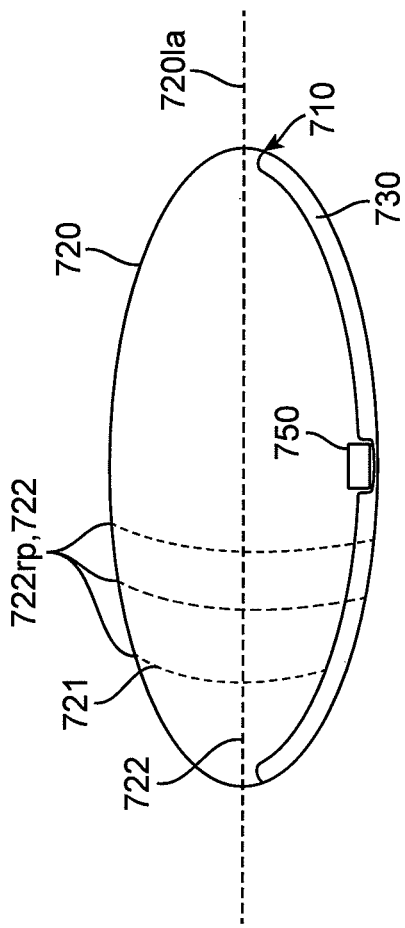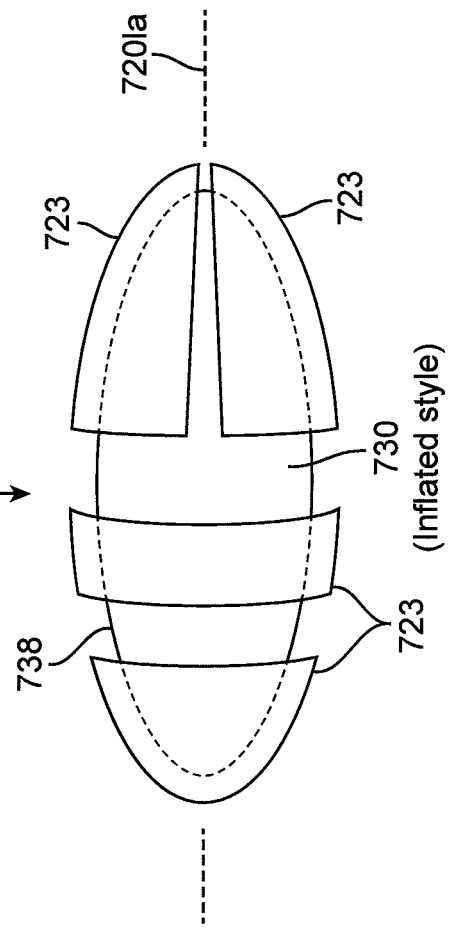

SWALLOWABLE DRUG DELIVERY DEVICE AND METHODS OF DRUG DELIVERY

CROSS-REFERENCES TO RELATED APPLICATIONS

This application claims the benefit of priority to U.S. Application Ser. Nos. 61/339,941 filed Mar. 10, 2010, entitled, "Swallowable Drug Delivery Device and Methods of Delivery", 61/284,766, filed Dec. 24, 2009, entitled, "Swallowable Drug Delivery Device and Methods of Drug Delivery", 61/340,331, filed Mar. 15, 2010, entitled "Swallowable Drug Delivery Device and Methods of Delivery"; and 61/395,304, filed May 10, 2010, entitled, "Swallowable Drug Delivery Device and Method of Delivery" all of which are fully incorporated by reference herein for all purposes. This application is also related to U.S. application Ser. No. 12/978,301, filed Dec. 23, 2010, entitled "Swallowable Drug Delivery Device and Method of Delivery"; and Ser. No. 12/978,164, filed Dec. 23, 2010, entitled, "Therapeutic Agent Preparations for Delivery into a Lumen of the Intestinal Tract Using a Swallowable Drug Delivery Device"; all of which are fully incorporated by reference herein for all purposes.

BACKGROUND OF THE INVENTION

Field of the Invention

Embodiments of the invention relate to swallowable drug delivery devices. More specifically, embodiments of the invention relate to swallowable drug delivery devices for delivering drugs to the small intestine.

While there has been an increasing development of new drugs in recent years for the treatment of a variety of diseases, many have limited application because they cannot be given orally. This is due to a number of reasons including: poor oral toleration with complications including gastric irritation and bleeding; breakdown/degradation of the drug compounds in the stomach; and poor, slow or erratic absorption of the drug. Conventional alternative drug delivery methods such as intravenous and intramuscular delivery have a number of drawbacks including pain and risk of infection from a needle stick, requirements for the use of sterile technique and the requirement and associated risks of maintaining an IV line in a patient for an extended period of time. While other drug delivery approaches have been employed such as implantable drug delivery pumps, these approaches require the semi-permanent implantation of a device and can still have many of the limitations of IV delivery. Thus, there is a need for an improved method for delivery of drugs and other therapeutic agents.

BRIEF SUMMARY OF THE INVENTION

Embodiments of the invention provide devices, systems, kits and methods for delivering drugs and other therapeutic agents to various locations in the body. Many embodiments provide a swallowable device for delivering drugs and other therapeutic agents within the Gastrointestinal (GI) tract. Particular embodiments provide a swallowable device such as a capsule for delivering drugs and other therapeutic agents into the wall of the small intestine, large intestine or other GI organ wall. Embodiments of the invention are particularly useful for the delivery of drugs and other therapeutic agents which are poorly absorbed, poorly tolerated and/or chemically degraded (e.g. breakdown of the chemical structure of the molecule) within the GI tract (e.g. the digestive enzymes and acids in the stomach). Further, embodiments of the invention can be used to deliver drugs which were previously only capable of or preferably delivered by intravenous or other form of parenteral administration (e.g., intramuscular, etc). Additionally, embodiments of the invention are useful for achieving rapid release of a drug into the blood stream via oral delivery.

Embodiments of the invention provide devices, systems, kits and methods for delivering drugs and other therapeutic agents to various locations in the body. Many embodiments provide a swallowable device for delivering drugs and other therapeutic agents within the Gastrointestinal (GI) tract. Particular embodiments provide a swallowable device such as a capsule for delivering drugs and other therapeutic agents into the wall of the small intestine or other GI organ wall. Embodiments of the invention are particularly useful for the delivery of drugs and other therapeutic agents which are poorly absorbed, poorly tolerated and/or degraded within the GI tract. Further, embodiments of the invention can be used to deliver drugs which were previously only capable of or preferably delivered by intravenous or other form of parenteral administration (e.g., intramuscular, etc).

In one aspect, the invention provides a swallowable device for delivering drugs or other therapeutic agent into the wall of the small or large intestine. The device comprises a capsule sized to be swallowed and pass through the intestinal tract. The capsule includes an interior volume and can be fabricated from various biocompatible polymers known in the art including various biodegradable polymers. The capsule can include at least one guide tube, one or more tissue penetrating members positioned in the at least one guide tube, a delivery member and an actuating mechanism. Alternatively, the tissue penetrating member can be positioned in the capsule without a guide tube. The tissue penetrating member will typically comprise a hollow needle or other like structure and will have a lumen or other compartment and a tissue penetrating end for penetrating a selectable depth into the intestinal wall. In various embodiments, the device can include a second and a third tissue penetrating member with additional numbers contemplated. Each tissue penetrating member can include the same or a different drug. In preferred embodiments having multiple tissue penetrating members, the tissue penetrating members can be symmetrically distributed around the perimeter of the capsule so as to anchor the capsule onto the intestinal wall during delivery of drug. In some embodiments, all or a portion of the tissue penetrating member (e.g., the tissue penetrating end) can be fabricated from the drug itself. In these and related embodiments, the drug can have a needle or dart-like structure (with or without barbs) configured to penetrate and be retained in the intestinal wall.

The tissue penetrating member can be fabricated from various biodegradable materials (e.g., PGLA) so as to degrade within the small intestine and thus provide a fail-safe mechanism for detaching the tissue penetrating member from the intestinal wall should this component become retained in the intestinal wall. Additionally, in theses and related embodiments, selectable portions of the capsule can be fabricated from such biodegradable materials so as to allow the entire device to controllably degrade into smaller pieces. Such embodiments facilitate passage and excretion of the devices through GI tract. In particular embodiments, the capsule can include seams of biodegradable material which controllably degrade to produce capsule pieces of a selectable size and shape to facilitate passage through the GI tract. The seams can be pre-stressed, perforated or otherwise treated to accelerate degradation. The concept of using biodegradable seams to produce controlled degradation of a swallowable device in the GI tract can also be applied to other swallowable devices such as swallowable cameras to facilitate passage through the GI tract and reduce the likelihood of a device becoming stuck in the GI tract.

The delivery member is configured to advance the drug from the capsule through the tissue penetrating member lumen and into the intestinal wall. Typically, at least a portion of the delivery member is advanceable within the tissue penetrating member lumen. The delivery member can have a piston or like structure sized to fit within the delivery member lumen. The distal end of the delivery member (the end which is advanced into tissue) can have a plunger element which advances the drug within tissue penetrating member lumen and also forms a seal with the lumen. The plunger element can be integral or attached to the delivery member. Preferably, the delivery member is configured to travel a fixed distance within the needle lumen so as to deliver a fixed or meter dose of drug into the intestinal wall. This can be achieved by one or more of the selection of the diameter of the delivery member (e.g., the diameter can be distally tapered), the diameter of the tissue penetrating member (which can be narrowed at its distal end), use of a stop, and/or the actuating mechanism. For embodiments of the device having a tissue penetrating member fabricated from drug (e.g., a drug dart), the delivery member is adapted to advance the dart out of the capsule and into tissue.

The delivery member and tissue penetrating member can be configured for the delivery of liquid, semi-liquid or solid forms of drug or all three. Solid forms of drug can include both powder or pellet. Semi liquid can include a slurry or paste. The drug can be contained within a cavity of the capsule, or in the case of the liquid or semi-liquid, within an enclosed reservoir. In some embodiments, the capsule can include a first second, or a third drug (or more). Such drugs can be contained within the tissue penetrating member lumen (in the case of solids or powder) or in separate reservoirs within the capsule body.

The actuating mechanism can be coupled to at least one of the tissue penetrating member or the delivery member. The actuating mechanism is configured to advance the tissue penetrating member a selectable distance into the intestinal wall as well as advance the delivery member to deliver the drug and then withdraw the tissue penetrating member from the intestinal wall. In some embodiments, e.g., where the tissue penetrating member is itself the drug, the actuating mechanism is configured to leave the tissue penetrating member within the intestinal wall. In various embodiments, the actuating mechanism can comprise a preloaded spring mechanism which is configured to be released by the release element. Suitable springs can include both coil (including conical shaped springs) and leaf springs with other spring structures also contemplated. In particular embodiments, the spring can be cone shaped to reduce the length of the spring in the compressed state even to the point where the compressed length of the spring is about the thickness of several coils (e.g., two or three) or only one coil.

In particular embodiments the actuating mechanism comprises a spring, a first motion converter, and a second motion converter and a track member. The release element is coupled to the spring to retain the spring in a compressed state such that degradation of the release element releases the spring. The first motion converter is configured to convert motion of the spring to advance and withdraw the tissue penetrating element in and out of tissue. The second motion converter is configured to convert motion of the spring to advance the delivery member into the tissue penetrating member lumen. The motion converters are pushed by the spring and ride along a rod or other track member which serves to guide the path of the converters. They engage the tissue penetrating member and/or delivery member (directly or indirectly) to produce the desired motion. They are desirably configured to convert motion of the spring along its longitudinal axis into orthogonal motion of the tissue penetrating member and/or delivery member though conversion in other directions is also contemplated. The motion converters can have a wedge, trapezoidal or curved shape with other shapes also contemplated. In particular embodiments, the first motion converter can have a trapezoidal shape and include a slot which engages a pin on the tissue penetrating member that rides in the slot. The slot can have a trapezoidal shape that mirrors or otherwise corresponds to the overall shape of the converter and serves to push the tissue penetrating member during the upslope portion of the trapezoid and then pull it back during the down slope portion. In one variation, one or both of the motion converters can comprise a cam or cam like device which is turned by the spring and engages the tissue penetrating and/or delivery member.

In other variations, the actuating mechanism can also comprise an electro-mechanical device/mechanism such as a solenoid, or a piezoelectric device. In one embodiment, the piezoelectric device can comprise a shaped piezoelectric element which has a non-deployed and deployed state. This element can be configured to go into the deployed state upon the application of a voltage and then return to the non-deployed state upon the removal of the voltage. This and related embodiments allow for a reciprocating motion of the actuating mechanism so as to both advance the tissue penetrating member and then withdraw it.

The release element is coupled to at least one of the actuating mechanism or a spring coupled to the actuating mechanism. In particular embodiments, the release element is coupled to a spring positioned within the capsule so as to retain the spring in compressed state. Degradation of the release element releases the spring to actuate the actuation mechanism. In many embodiments, the release element comprises a material configured to degrade upon exposure to chemical conditions in the small or large intestine such as pH. Typically, the release element is configured to degrade upon exposure to a selected pH in the small intestine, e.g., 7.0, 7.1, 7.2, 7.3, 7.4, 8.0 or greater. However, it can also be configured to degrade in response to other conditions in the small intestine. In particular embodiments, the release element can be configured to degrade in response to particular chemical conditions in the fluids in the small intestine such as those which occur after ingestion of a meal (e.g., a meal high in fats or proteins).

Biodegradation of the release element from one or more conditions in the small intestine (or other location in the GI tract) can be achieved by selection of the materials for the release element, the amount of cross linking of those materials as well as the thickness and other dimensions of the release elements. Lesser amounts of cross linking and or thinner dimensions can increase the rate of degradation and visa versa. Suitable materials for the release element can comprise biodegradable materials such as various enteric materials which are configured to degrade upon exposure to the higher pH or other condition in the small intestine. The enteric materials can be copolymerized or otherwise mixed with one or more polymers to obtain a number of particular material properties in addition to biodegradation. Such properties can include without limitation stiffness, strength, flexibility and hardness.

In particular embodiments, the release element can comprise a film or plug that fits over or otherwise blocks the guide tube and retains the tissue penetrating member inside the guide tube and/or capsule. In these and related embodiments, the tissue penetrating member is coupled to a spring loaded actuating mechanism such that when the release element is degraded sufficiently, it releases the tissue penetrating member which then springs out of the guide tube to penetrate into the intestinal wall. In other embodiments, the release element can be shaped to function as a latch which holds the tissue penetrating element in place. In these and related embodiments, the release element can be located on the exterior or the interior of the capsule. In the interior embodiments, the capsule and guide tubes are configured to allow for the ingress of intestinal fluids into the capsule interior to allow for the degradation of the release element.

In some embodiments, the actuating mechanism can be actuated by means of a sensor, such as a pH or other chemical sensor which detects the presence of the capsule in the small intestine and sends a signal to the actuating mechanism (or to an electronic controller coupled to the actuating mechanism to actuate the mechanism). Embodiments of a pH sensor can comprise an electrode-based sensor or it can be a mechanically-based sensor such as a polymer which shrinks or expands upon exposure to the pH or other chemical conditions in the small intestine. In related embodiments, an expandable/contractable sensor can also comprise the actuating mechanism itself by using the mechanical motion from the expansion or contraction of the sensor.

According to another embodiment for detecting that the device is in the small intestine (or other location in the GI tract), the sensor can comprise a strain gauge or other pressure/force sensor for detecting the number of peristaltic contractions that the capsule is being subject to within a particular location in the intestinal tract. In these embodiments, the capsule is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments detection of the number of peristaltic contractions can be used to not only determine if the capsule is in the small intestine but the relative location within the intestine as well.

As an alternative or supplement to internally activated drug delivery, in some embodiments, the user may externally activate the actuating mechanism to deliver drug by means of RF, magnetic or other wireless signaling means known in the art. In these and related embodiments, the user can use a handheld device (e.g., a hand held RF device) which not only includes signaling means, but also means for informing the user when the device is in the small intestine or other location in the GI tract. The later embodiment can be implemented by including an RF transmitter on the swallowable device to signal to the user when the device is in the small intestine or other in the GI tract location (e.g., by signaling an input from the sensor). The same handheld device can also be configured to alter the user when the actuating mechanism has been activated and the selected drug(s) delivered. In this way, the user is provided confirmation that the drug has been delivered. This allows the user to take other appropriate drugs/therapeutic agents as well as make other related decisions (e.g., for diabetics to eat a meal or not and what foods should be eaten). The handheld device can also be configured to send a signal to the swallowable device to over-ride the actuating mechanism and so prevent, delay or accelerate the delivery of drug. In use, such embodiments allow the user to intervene to prevent, delay or accelerate the delivery of drug based upon other symptoms and/or patient actions (e.g., eating a meal, deciding to go to sleep, exercise etc).

The user may also externally activate the actuating mechanism at a selected time period after swallowing the capsule. The time period can be correlated to a typical transit time or range of transit times for food moving through the user's GI tract to a particular location in the tract such as the small intestine.

Another aspect of the invention provides methods for the delivery of drugs into the walls of the GI tract using embodiments of the drug swallowable drug delivery devices. Such methods can be used for the delivery of therapeutically effective amounts of a variety of drugs and other therapeutic agents. These include a number of large molecule peptides and proteins which would otherwise require injection due to their chemical breakdown in the stomach/GI tract e.g., growth hormone, parathyroid hormone, insulin, interferons and other like compounds. Suitable drugs and other therapeutic agents which can be delivered by embodiments of invention include various chemotherapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents, immune suppression agents and anti parasitic agents such as various anti malarial agents. The dosage of the particular drug can be titrated for the patient's weight, age or other parameter.

In various method embodiments, embodiments of the drug swallowable drug delivery device can be used to deliver a plurality of drugs for the treatment of multiple conditions or for the treatment of a particular condition (e.g., protease inhibitors for treatment HIV AIDS). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream at about the same time. Due to differences in chemical makeup, molecular weight, etc, drugs can be absorbed through the intestinal wall at different rates, resulting in different pharmacokinetic distribution curves and so reaching the target tissue at different times. Embodiments of the invention address this issue by injecting the desired drug mixtures at about the same time. This in turn improves pharmacokinetics and thus, the efficacy of the selected mixture of drugs.

Embodiments of the invention provide devices, systems, kits and methods for delivering drugs and other therapeutic agents to various locations in the body. Many embodiments provide a swallowable device for delivering drugs and other therapeutic agents within the GI tract. Particular embodiments provide a swallowable device such as a capsule for delivering drugs and other therapeutic agents into the wall of the small intestine or other GI organ wall. Embodiments of the invention are particularly useful for the delivery of drugs and other therapeutic agents which are poorly absorbed, poorly tolerated and/or chemically degraded (e.g. a breakdown of the chemical structure of the molecule) within the GI tract (e.g., by the digestive enzymes and acids in the stomach). Further, embodiments of the invention can be used to deliver drugs which were previously only capable of or preferably delivered by intravenous or other form of parenteral administration (e.g., intramuscular, etc).

In one aspect, the invention provides a swallowable device for delivering drugs or other therapeutic agent into the wall of the small or large intestine. The device comprises a capsule sized to be swallowed and pass through the intestinal tract.

The capsule includes an interior volume and can be fabricated from various biocompatible polymers known in the art including various biodegradable polymers. The capsule includes at least one guide tube, one or more tissue penetrating members positioned in the at least one guide tube, a delivery member and an actuating mechanism. The tissue penetrating member will typically comprise a hollow needle or other like structure and will have a lumen and a tissue penetrating end for penetrating a selectable depth into the intestinal wall. In various embodiments, the device can include a second and a third tissue penetrating member with additional numbers contemplated. Each tissue penetrating member can include the same or a different drug. In preferred embodiments having multiple tissue penetrating members, the tissue penetrating members can be symmetrically distributed around the perimeter of the capsule so as to anchor the capsule onto the intestinal wall during delivery of drug. In some embodiments, all or a portion of the tissue penetrating member (e.g., the tissue penetrating end) can be fabricated from the drug itself. In these and related embodiments, the drug can have a needle or dart-like structure (with or without barbs) configured to penetrate and be retained in the intestinal wall.

The tissue penetrating member can be fabricated from various biodegradable materials (e.g., PGLA) so as to degrade within the small intestine and thus provide a fail-safe mechanism for detaching the tissue penetrating member from the intestinal wall should this component become retained in the intestinal wall. Additionally, in theses and related embodiments, selectable portions of the capsule can be fabricated from such biodegradable materials so as to allow the entire device to controllably degrade into smaller pieces. Such embodiments facilitate passage and excretion of the devices through GI tract. In particular embodiments, the capsule can include seams of biodegradable material which controllably degrade to produce capsule pieces of a selectable size and shape to facilitate passage through the GI tract. The seams can be pre-stressed, perforated or otherwise treated to accelerate degradation. The concept of using biodegradable seams to produce controlled degradation of a swallowable device in the GI tract can also be applied to other swallowable devices such as swallowable cameras to facilitate passage through the GI tract and reduce the likelihood of a device becoming stuck in the GI tract.

The delivery member is configured to advance the drug from the capsule through the tissue penetrating member lumen and into the intestinal wall such as the wall of the small intestine. Typically, at least a portion of the delivery member is advanceable within the tissue penetrating member lumen. The delivery member can have a piston or like structure sized to fit within the delivery member lumen. The distal end of the delivery member (the end which is advanced into tissue) can have a plunger element which advances the drug within tissue penetrating member lumen and also forms a seal with the lumen. The plunger element can be integral or attached to the delivery member. Preferably, the delivery member is configured to travel a fixed distance within the needle lumen so as to deliver a fixed or metered dose of drug into the intestinal wall. This can be achieved by one or more of the selection of the diameter of the delivery member (e.g., the diameter can be distally tapered), the diameter of the tissue penetrating member (which can be narrowed at its distal end), use of a stop, and/or the actuating mechanism. For embodiments of the device having a tissue penetrating member fabricated from drug (e.g., a drug dart), the delivery member is adapted to advance the dart out of the capsule and into tissue.

The delivery member and tissue penetrating member can be configured for the delivery of liquid, semi-liquid or solid forms of drug (or other therapeutic agent) or all three. Solid forms of drug can include both powder or pellet. Semi liquid can include a slurry or paste. The drug can be contained within a cavity of the capsule, or in the case of the liquid or semi-liquid, within an enclosed reservoir. In some embodiments, the capsule can include a first second, or a third drug (or more). Such drugs can be contained within the tissue penetrating member lumen (in the case of solids or powder) or in separate reservoirs within the capsule body.

The actuating mechanism can be coupled to at least one of the tissue penetrating member or the delivery member. The actuating mechanism is configured to advance the tissue penetrating member a selectable distance into the intestinal wall as well as advance the delivery member to deliver the drug and then withdraw the tissue penetrating member from the intestinal wall. In various embodiments, the actuating mechanism can comprise a preloaded spring mechanism which is configured to be released by the release element. Suitable springs can include both coil (including conical shaped springs) and leaf springs with other spring structures also contemplated. In particular embodiments, the spring can be cone shaped to reduce the length of the spring in the compressed state even to the point where the compressed length of the spring is about the thickness of several coils (e.g., two or three) or only one coil.

In particular embodiments the actuating mechanism comprises a spring, a first motion converter, and a second motion converter and a track member. The release element is coupled to the spring to retain the spring in a compressed state such that degradation of the release element releases the spring. The first motion converter is configured to convert motion of the spring to advance and withdraw the tissue penetrating element in and out of tissue. The second motion converter is configured to convert motion of the spring to advance the delivery member into the tissue penetrating member lumen. The motion converters are pushed by the spring and ride along a rod or other track member which serves to guide the path of the converters. They engage the tissue penetrating member and/or delivery member (directly or indirectly) to produce the desired motion. They are desirably configured to convert motion of the spring along its longitudinal axis into orthogonal motion of the tissue penetrating member and/or delivery member though conversion in other directions is also contemplated. The motion converters can have a wedge, trapezoidal or curved shape with other shapes also contemplated. In particular embodiments, the first motion converter can have a trapezoidal shape and include a slot which engages a pin on the tissue penetrating member that rides in the slot. The slot can have a trapezoidal shape that mirrors or otherwise corresponds to the overall shape of the converter and serves to push the tissue penetrating member during the upslope portion of the trapezoid and then pull it back during the down slope portion. In one variation, one or both of the motion converters can comprise a cam or cam like device which is turned by the spring and engages the tissue penetrating and/or delivery member.

In other variations, the actuating mechanism can also comprise an electro-mechanical device/mechanism such as a solenoid, or a piezo-electric device. In one embodiment, the piezo-electric device can comprise a shaped piezo-electric element which has a non-deployed and deployed state. This element can be configured to go into the deployed state upon the application of a voltage and then return to the non-deployed state upon the removal of the voltage. This and related embodiments allow for a reciprocating motion of the actuating mechanism so as to both advance the tissue penetrating member and then withdraw it.

The release element is coupled to at least one of the actuating mechanism or a spring coupled to the actuating mechanism. In particular embodiments, the release element is coupled to a spring positioned within the capsule so as to retain the spring in a compressed state. Degradation of the release element releases the spring to actuate the actuation mechanism. In many embodiments, the release element comprises a material configured to degrade upon exposure to chemical conditions in the small or large intestine such as pH. Typically, the release element is configured to degrade upon exposure to a selected pH in the small intestine, e.g., 7.0, 7.1, 7.2, 7.3, 7.4, 8.0 or greater. However, it can also be configured to degrade in response to other conditions in the small intestine. In particular embodiments, the release element can be configured to degrade in response to particular chemical conditions in the fluids in the small intestine such as those which occur after ingestion of a meal (e.g., a meal high in fats or proteins).

Biodegradation of the release element from one or more conditions in the small intestine (or other location in the GI tract) can be achieved by selection of the materials for the release element, the amount of cross linking of those materials as well as the thickness and other dimensions of the release elements. Lesser amounts of cross linking and or thinner dimensions can increase the rate of degradation and visa versa. Suitable materials for the release element can comprise biodegradable materials such as various enteric materials which are configured to degrade upon exposure to the higher pH or other condition in the small intestine. The enteric materials can be copolymerized or otherwise mixed with one or more polymers to obtain a number of particular material properties in addition to biodegradation. Such properties can include without limitation stiffness, strength, flexibility and hardness.

In particular embodiments, the release element can comprise a film or plug that fits over or otherwise blocks the guide tube and retains the tissue penetrating member inside the guide tube. In these and related embodiments, the tissue penetrating member is coupled to a spring loaded actuating mechanism such that when the release element is degraded sufficiently, it releases the tissue penetrating member which then springs out of the guide tube to penetrate into the intestinal wall. In other embodiments, the release element can be shaped to function as a latch which holds the tissue penetrating element in place. In these and related embodiments, the release element can be located on the exterior or the interior of the capsule. In the interior embodiments, the capsule and guide tubes are configured to allow for the ingress of intestinal fluids into the capsule interior to allow for the degradation of the release element.

In some embodiments, the actuating mechanism can be actuated by means of a sensor, such as a pH or other chemical sensor which detects the presence of the capsule in the small intestine and sends a signal to the actuating mechanism (or to an electronic controller coupled to the actuating mechanism to actuate the mechanism). Embodiments of a pH sensor can comprise an electrode-based sensor or it can be a mechanically-based sensor such as a polymer which shrinks or expands upon exposure to the pH or other chemical conditions in the small intestine. In related embodiments, an expandable/contractable sensor can also comprise the actuating mechanism itself by using the mechanical motion from the expansion or contraction of the sensor.

According to another embodiment for detecting that the device is in the small intestine (or other location in the GI tract), the sensor can comprise a strain gauge or other pressure/force sensor for detecting the number of peristaltic contractions that the capsule is being subject to within a particular location in the intestinal tract. In these embodiments, the capsule is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments detection of the number of peristaltic contractions can be used to not only determine if the capsule is in the small intestine but the relative location within the intestine as well.

As an alternative or supplement to internally activated drug delivery, in some embodiments, the user may externally activate the actuating mechanism to deliver drug by means of RF, magnetic or other wireless signaling means known in the art. In these and related embodiments, the user can use a handheld device (e.g., a hand held RF device) which not only includes signaling means, but also means for informing the user when the device is in the small intestine or other location in the GI tract. The later embodiment can be implemented by including an RF transmitter on the swallowable device to signal to the user when the device is in the small intestine or other location (e.g., by signaling an input from the sensor). The same handheld device can also be configured to alter the user when the actuating mechanism has been activated and the selected drug(s) delivered. In this way, the user is provided confirmation that the drug has been delivered. This allows the user to take other appropriate drugs/therapeutic agents as well as make other related decisions (e.g., for diabetics to eat a meal or not and what foods should be eaten). The handheld device can also be configured to send a signal to the swallowable device to over-ride the actuating mechanism and so prevent, delay or accelerate the delivery of drug. In use, such embodiments allow the user to intervene to prevent, delay or accelerate the delivery of drug based upon other symptoms and/or patient actions (e.g., eating a meal, deciding to go to sleep, exercise etc).

The user may also externally activate the actuating mechanism at a selected time period after swallowing the capsule. The time period can be correlated to a typical transit time or range of transit times for food moving through the user's GI tract to a particular location in the tract such as the small intestine.

Another aspect of the invention provides therapeutic agent preparations for delivery into the wall of the small intestine (or other luminal wall in the intestinal tract) using embodiments of the swallowable device described herein. The preparation comprises a therapeutically effective dose of at least one therapeutic agent (e.g., insulin, an anti-seizure compound, NSAIDs, an antibiotic, etc.). It may comprise a solid, liquid or combination of both and can include one or more pharmaceutical excipients. The preparation has a shape and material consistency to be contained in embodiments of the swallowable capsule, delivered from the capsule into the lumen wall and degrade within the lumen wall to release the dose of therapeutic agent. The preparation may also have a selectable surface area to volume ratio so as enhance or otherwise control the rate of degradation of the preparation in the wall of the small intestine or other body lumen. In various embodiments, the preparation can be configured to be coupled to an actuator (such as a release element (and/or other components coupled to the release element) which has a first configuration in which the preparation is contained in the capsule and a second configuration in which the preparation is advanced out of the capsule and into the wall of the small intestine. The dose of the drug or other therapeutic agent in the preparation can be titrated downward from that which would be required for conventional oral delivery methods so that potential side effects from the drug can be reduced.

Typically, though not necessarily, the preparation will be shaped and otherwise configured to be contained in the lumen of a tissue penetrating member, such as a hollow needle which is configured to be advanced out of the capsule and into the wall of the small intestine. The preparation itself may comprise a tissue penetrating member configured to be advanced into the wall of the small intestine or other lumen in the intestinal tract.

Another aspect of the invention provides methods for the delivery of drugs and the therapeutic agents into the walls of the GI tract using embodiments of the swallowable drug delivery devices. Such methods can be used for the delivery of therapeutically effective amounts of a variety of drugs and other therapeutic agents. These include a number of large molecule peptides and proteins which would otherwise require injection and/or IV infusion due to chemical degradation by the digestive fluids in the stomach and lumen of the small intestine. Such compounds which can be delivered with various embodiments of the invention can include without limitation, growth hormone, parathyroid hormone, insulin compounds, antibodies and other gamma globulin proteins (e.g., gamma globulin) interferons and other cytokines, glucagon like peptides e.g., (GLP-1, exenatide) and other incretins, parathyroid hormones, growth hormones (e.g., IFG and other growth factors), chemotherapeutic agents (doxorubicin) and other like compounds. Other drugs and other therapeutic agents which can be delivered by embodiments of invention include any number of orally delivered agents, antibiotics (vancomycin, penicillin, erythromycin, etc.), antivirals (protease inhibitors anti-seizure compounds (furosemide, dilatin), NSIAD's (ibuprofen), immune suppression agents and anti parasitic agents such as various anti malarial agents. Many of these compounds can include various therapeutic agents which if taken by standard oral delivery methods would cause deleterious effects in the intestinal tract and elsewhere such as cramping, bleeding, diarrhea and irritable bowel. Because various embodiments of the inventions provide for the drug or other therapeutic agent being injected directly into the small intestine, these effects can largely be avoided and the dosage of the compound can be adjusted accordingly (e.g., increased in many cases). In various embodiments, the dosage of a particular drug can be titrated for these considerations as well as the patient's weight, age and condition to be treated.

In various method embodiments, embodiments of the swallowable drug delivery device can be used to deliver a plurality of drugs for the treatment of multiple conditions or for the treatment of a particular condition (e.g., a mixture of protease inhibitors for treatment HIV AIDS). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream at about the same time. Due to differences in chemical makeup, molecular weight, etc., drugs can be absorbed through the intestinal wall at different rates, resulting in different pharmacokinetic distribution curves. Embodiments of the invention address this issue by injecting the desired drug mixtures into the intestinal wall at about the same time. This in turn improves pharmacokinetics and thus, the efficacy of the selected mixture of drugs.

Further details of these and other embodiments and aspects of the invention are described more fully below, with reference to the attached drawing figures.

Embodiments of the invention provide devices, systems, kits and methods for delivering drugs and other therapeutic agents to various locations in the body. Many embodiments provide a swallowable device for delivering drugs and other therapeutic agents within the Gastrointestinal (GI) tract. Particular embodiments provide a swallowable device such as a capsule for delivering drugs and other therapeutic agents into the wall of the small intestine, large intestine or other GI organ wall. Embodiments of the invention are particularly useful for the delivery of drugs and other therapeutic agents which are poorly absorbed, poorly tolerated and/or degraded within the GI tract. Further, embodiments of the invention can be used to deliver drugs which were previously only capable of or preferably delivered by intravenous or other form of parenteral administration (e.g., intramuscular, etc). Additionally, embodiments of the invention are useful for achieving rapid release of a drug into the blood stream via oral delivery.

In one aspect, the invention provides a swallowable device for delivering drugs or other therapeutic agent into the wall of the small or large intestine or other intestinal tract organ. The devise comprises a capsule sized to be swallowed and pass through the intestinal tract, an expandable member positioned within capsule and a tissue penetrating member advanceable into the intestinal wall by expansion of the expandable member. The capsule includes an interior volume and at least one aperture through which the tissue penetrating member can be advanced into the intestinal wall. The tissue penetrating member is formed at least in part from a drug or other therapeutic. The capsule can be fabricated from various non-toxic materials including various biodegradable polymers. The capsule may also have a enteric other coating for protecting the capsule from stomach acids while allowing for biodegradation in the small intestine so as to allow the device to deliver drugs and other therapeutic agents into the wall of the small intestine responsive to pH or other conditions in the small intestine.

A balloon or other expandable member is disposed within the capsule interior volume and coupled to the tissue penetrating member. The balloon will typically be attached to an interior wall of the capsule in a least a partially non-expanded state and can comprise various non compliant polymers known in the art such as PET, polyethylene and polyimide. Desirably, the balloon will be thin walled e.g., less than about 0.001 inches. The balloon also will typically include at least a first and a second portion or compartment which are separated by be a separation valve or other separation means. A liquid, typically water, can be disposed within the first compartment and at least one reactant disposed in the second compartment which can be liquid though typically is solid. The reactants will typically include at least two reactants for example, an acid such as citric acid and a base such as sodium hydroxide, which can have about a 1:2 ratio. Other reactants including other acids, e.g., ascetic acid and bases are also contemplated. When the valve or other separation means opens, the reactants mix in the liquid and produce a gas such as carbon dioxide which expands the balloon and advances the tissue penetrating member into the intestinal wall as will be explained more fully herein. In addition to advancing the tissue penetrating members into tissue, the device can also be configured to have the inflated balloon break or otherwise separate apart the capsule into one or more pieces for easier passage through the intestinal tract.

The separation valve can be configured to open in a number of ways and responsive to a number of conditions. Typically, the separation valve will be configured to open by having one or more portions degrade in response to the higher pH or other conditions found within the small intestine so that upon degradation, the valve opens. Also, typically, the separation valve will be placed in a central portion of the balloon, though other locations are also contemplated. In particular embodiments, the separation valve can have a beam like structure that is placed within the capsule to compress the portion of the balloon between the first and second compartments. The beam can be attached at one or both ends to the internal surface of the capsule. In preferred embodiments, the beam is attached to the radial sides of the capsule preferably, using an interference fit so that the beam can be snapped into place using pick and place and other like methods known in the manufacturing arts. When the beam degrades, the compressive forces are released. These and other embodiments of the valve can include one or more pinching features such as a ridge which engages a depression or other mating feature on the internal surface of the capsule to apply additional force on the balloon wall beneath the pinching feature and redundancy to the seal. In another embodiment, the separation valve can comprise a necked section of the expandable member with an overlying pinching collar made from biodegradable material. The collar holds the valve closed and releases the valve when degraded.

The separation valve can be positioned in a variety of locations on or within the capsule so as to exposed to and degraded by the intestinal fluids. While at least a portion of the valve may be exposed to the capsule surface, typically, the valve will be positioned within the capsule interior where it is exposes to intestinal fluids which enter through the at least one aperture or other opening. In these and related embodiments, at least a portion of the capsule surface including the portion containing the at least one aperture is desirably coated with a protective layer, such as an enteric coating which also degrades in response to pH or other conditions within the small intestine. Such coatings provide a protective seal over the at least one aperture so that digestive fluids do not enter the capsule interior and start to degrade the separation valve until the capsule has reached the small intestine. In use, embodiments employing a degradable coating/seal over the aperture and a degradable valve provide a primary and secondary means assuring that balloon does not expand and deploy its tissue penetrating members until the capsule has reached the small intestine.

As an alternative or additional embodiment, the valve may also be configured to open in response to compressive forces applied by a peristaltic contraction within the small intestine. In still another approach, the valve may be a time release valve configured to open after a certain period of time after an activation step initiated by the patient such as the pealing of a tab or pressing of a button.

In addition to the release valve, the balloon or other expandable member will also typically include a deflation valve which serves to deflate the expandable member after inflation. The deflation valve can comprise biodegradable materials which are configured to degrade upon exposure to the fluids in the small intestine and/or liquid in one of the compartments of the balloon so as to create an opening or channel for escape of gas within balloon. In one embodiment, the deflation valve can comprise a biodegradable section positioned on an end portion of the balloon so as to join opposing ends of the balloon wall together. In this and related embodiments, when the degradable section degrades from exposure to the liquid, the balloon wall tears or otherwise comes apart providing for a high assurance of rapid deflation. Multiple degradable sections can be placed, desirably in the solid reactant portion of the balloon wall to provide an even higher degree of reliability in deflation. For embodiments where the deflation valve is degraded by fluids within the small intestine, degradation of the valve can be facilitated by configuring the inflated balloon to break apart the capsule into two or more pieces so that large sections of the balloon are directly exposed to degrading fluids within the small intestine. This can be achieved by fabricating the capsule from separate parts (e.g., two halves mechanically fit together) and/or through the use of seams as is described herein.

Additionally, as further backup for insured deflation, one or more puncture elements can be attached to the inside surface of the capsule wall such that when the balloon fully deflates it is contacts and is punctured by the puncture element. In another alternative or additional embodiment of means for deflation, one or more of the tissue penetrating members can be directly coupled to the balloon and configured to tear away from the balloon when they detach, tearing the balloon wall in the process.

The tissue penetrating member in this aspect of the invention can be fabricated from various drugs and other therapeutic agents. Typically, the drug or other therapeutic agent will be mixed in with a biodegradable polymer such as PGLA. In such embodiments, the penetrating member may comprise a substantially heterogeneous mixture of drug and biodegradable polymer. Alternatively, the penetrating member may include a portion formed substantially from biodegradable and a separate section or compartment that is formed from or contains the drug. The penetrating member can be formed to have a shaft and a needle tip or other pointed distal tip so as to readily penetrate tissue of the intestinal wall. Once placed in intestinal wall, the tissue penetrating member is degraded by the interstitial fluids within the wall tissue, the drug dissolves in those fluids and is absorbed into the blood stream. The penetrating member will also typically include one or more tissue retaining features such as a barb or hook to retain the penetrating member within the tissue of the intestinal wall after advancement. The retaining features can be arranged in various patterns to enhance tissue retention such as two or more barbs symmetrically distributed around the member shaft. The drug can be in solid form and then formed into the shape of the tissue penetrating member using molding or other like method or may be in solid or liquid form and then added to the biodegradable polymer in liquid form with the mixture then formed into the penetrating member using molding or other forming method known in the polymer arts. Desirably, embodiments of the tissue penetrating member comprising a drug and degradable polymer are formed (e.g., cured) at temperatures which do not produce any substantial thermal degradation of the drug including drugs such as various peptides and proteins. This can be achieved through the use of room-temperature curing polymers and room temperature molding and solvent evaporation techniques known in the art. In particular embodiments, the amount of thermally degraded drug within the tissue penetrating member is desirably less than about 10% by weight, more preferably less than 5% and still more preferably less than 1%. The thermal degradation temperatures for a particular drug are known or can be determined using methods known in the art and then this temperature can be used to select and adjust the particular polymer processing methods (e.g., molding, curing, solvent evaporation etc.).

The tissue penetrating member is desirably detachably coupled (directly or indirectly) to the balloon or other expandable member so that after advancement of the tissue penetrating member into the intestinal wall, the tissue penetrating member detaches from the balloon. The penetrating member can be configured to detach as a result of balloon deflation where the retaining features hold the penetrating member in tissue as the balloon deflates and/or the forces exerted on the capsule by a peristaltic contraction of the small intestine. Typically, the tissue penetrating member will be indirectly coupled to the balloon by an advancement member comprising a rigid structure attached to the balloon surface which detachably engages the penetrating member. The advancement member engages the penetrating member by means of an attachment feature such as a pin which fits into a recess or other mating feature of the penetrating member. The pin and recess can be configured to detach from the force of balloon deflation and/or force applied to the capsule by peristaltic contraction. The rigid advancement member can have a larger horizontal surface area than the penetrating member so as to function as a force concentration element to increase the force per unit area applied to the penetrating member from balloon expansion. In some embodiments, the advancement member can be coupled to the balloon via a platform also described herein as a support member having one surface attached to the balloon surface and the other attached to the advancement member. The support member can be sized to allow for attachment and advancement of multiple advancement and tissue penetrating members. Additionally, the support member can have a larger surface area than the advancement members/tissue penetrating members so as to have a force concentrating function similar to that described above for the advancement member. As an additional or alternative embodiment, the tissue penetrating member may be directly coupled to the balloon, e.g., by an adhesive. In these and related embodiments the tissue penetrating members may be configured to tear the balloon wall when they detach and thus provide a means for balloon deflation.

Multiple tissue penetrating members can be coupled to the balloon or other expandable member and they may have a number of arrangements. In specific embodiments, the capsule can include two, three or four penetrating members with additional numbers contemplated. The penetrating members can carry the same or a different drug. The former provides for larger amounts of delivery of a particular drug, the later allows two or more drugs to be delivered into the intestinal wall at about the same time. The tissue penetrating members can be placed and distributed in number of locations and patterns on the balloon surface. In particular embodiments, the penetrating members can be placed on opposite sides of the balloon (e.g., 180 apart with respect to the perimeter of the balloon) so that balloon inflation can place tissue penetrating members on opposite sides of the intestinal wall lumen. In preferred embodiments having multiple tissue penetrating members, the tissue penetrating members can be symmetrically distributed around the perimeter of the capsule so as to anchor the capsule onto the intestinal wall during delivery of drug as well as place the tissue penetrating members in multiple locations in the intestinal wall. This not only allows for additional amounts of drug to be delivered but also provides for a more even distribution of the drug within the intestinal wall providing for faster absorption into the blood stream.

As an additional or alternative embodiment to the use of drug carrying tissue penetrating members, various embodiments of the device can also include drug reservoirs disposed in the capsule which are compressible by expansion of the balloon or other expandable member. The reservoirs contain drug or other therapeutic agent in liquid or powder form. For liquid form, the drug will be dissolved in an aqueous drug solution. In these and related embodiments, the reservoirs are fluidically coupled to advanceable hollow tissue penetrating members such that inflation of the balloon compresses the reservoirs so as to force the drug solution through tissue penetrating member and into the intestinal wall. Multiple reservoirs are contemplated including two, three, four or more. In particular embodiments, two reservoirs can be coupled to a hollow tissue penetrating member with the reservoirs placed about 180 degrees apart with respect to the lengthwise axis of the penetrating member. Typically, the reservoirs will be fluidically coupled to the hollow penetrating member by means of a manifold. Suitable manifolds include a t-shaped manifold having connectors on either of it lateral ends for the reservoirs a central connector for the hollow tissue penetrating member and a central lumen or channel going to all connectors. Other shapes and manifold configurations are also contemplated.

In another aspect, the invention provides a swallowable device for delivering drugs or other therapeutic agent into the wall of the small or large intestine comprising a capsule sized to be swallowed and pass through the intestinal tract wherein the capsule includes at least one guide tube, one or more tissue penetrating members positioned in the at least one guide tube, a delivery member and an actuating mechanism. In these and related embodiments, the tissue penetrating member will typically comprise a hollow needle or other like structure and will have a lumen and a tissue penetrating end for penetrating a selectable depth into the intestinal wall. In various embodiments, the device can include a second and a third tissue penetrating member with additional numbers contemplated. Each tissue penetrating member can include the same or a different drug. In preferred embodiments having multiple tissue penetrating members, the tissue penetrating members can be symmetrically distributed around the perimeter of the capsule so as to anchor the capsule onto the intestinal wall during delivery of drug. In some embodiments, all or a portion of the tissue penetrating member (e.g., the tissue penetrating end) can be fabricated from the drug itself. In these and related embodiments, the drug can have a needle or dart-like structure (with or without barbs) configured to penetrate and be retained in the intestinal wall.

Embodiments of the tissue penetrating member in this aspect of the invention can be fabricated from various biodegradable materials (e.g., PGLA) so as to degrade within the small intestine and thus provide a fail-safe mechanism for detaching the tissue penetrating member from the intestinal wall should this component become retained in the intestinal wall. Additionally, in theses and related embodiments, selectable portions of the capsule can be fabricated from such biodegradable materials so as to allow the entire device to controllably degrade into smaller pieces. Such embodiments facilitate passage and excretion of the devices through GI tract. In particular embodiments, the capsule can include seams of biodegradable material which controllably degrade to produce capsule pieces of a selectable size and shape to facilitate passage through the GI tract. The seams can be pre-stressed, perforated or otherwise treated to accelerate degradation. The seams can also be so treated so to allow the capsule to be broken apart into smaller pieces by the forces applied from expansion of the balloon or other expandable member. In other embodiments for producing capsule degradation after deployment of the tissue penetrating members, the capsule can be comprise two halves or other fractional sections which are mechanically fit together, e.g., by a snap fit and thus readily separated by the forces applied from balloon inflation.

The delivery member is configured to advance the drug from the capsule through the tissue penetrating member lumen and into the intestinal wall. Typically, at least a portion of the delivery member is advanceable within the tissue penetrating member lumen. The delivery member can have a piston or like structure sized to fit within the delivery member lumen. The distal end of the delivery member (the end which is advanced into tissue) can have a plunger element which advances the drug within tissue penetrating member lumen and also forms a seal with the lumen. The plunger element can be integral or attached to the delivery member. Preferably, the delivery member is configured to travel a fixed distance within the needle lumen so as to deliver a fixed or metered dose of drug into the intestinal wall. This can be achieved by one or more of the selection of the diameter of the delivery member (e.g., the diameter can be distally tapered), the diameter of the tissue penetrating member (which can be narrowed at its distal end), use of a stop, and/or the actuating mechanism. For embodiments of the device having a tissue penetrating member fabricated from a drug (e.g., a drug dart), the delivery member is adapted to advance the tissue penetrating member out of the capsule and into tissue.

The delivery member and tissue penetrating member can be configured for the delivery of liquid, semi-liquid or solid forms of drug or all three. Solid forms of drug can include both powder or pellet. Semi liquid can include a slurry or paste. The drug can be contained within a cavity of the capsule, or in the case of the liquid or semi-liquid, within an enclosed reservoir. In some embodiments, the capsule can include a first second, or a third drug (or more). Such drugs can be contained within the tissue penetrating member lumen (in the case of solids or powder) or in separate reservoirs within the capsule body.

The actuating mechanism can be coupled to at least one of the tissue penetrating member or the delivery member. The actuating mechanism is configured to advance the tissue penetrating member a selectable distance into the intestinal wall as well as advance the delivery member to deliver the drug and then withdraw the tissue penetrating member from the intestinal wall. In various embodiments, the actuating mechanism can comprise a preloaded spring mechanism which is configured to be released by the release element. Suitable springs can include both coil (including conical shaped springs) and leaf springs with other spring structures also contemplated. In particular embodiments, the spring can be cone shaped to reduce the length of the spring in the compressed state even to the point where the compressed length of the spring is about the thickness of several coils (e.g., two or three) or only one coil.

In particular embodiments, the actuating mechanism comprises a spring, a first motion converter, and a second motion converter and a track member. The release element is coupled to the spring to retain the spring in a compressed state such that degradation of the release element releases the spring. The first motion converter is configured to convert motion of the spring to advance and withdraw the tissue penetrating element in and out of tissue. The second motion converter is configured to convert motion of the spring to advance the delivery member into the tissue penetrating member lumen. The motion converters are pushed by the spring and ride along a rod or other track member which serves to guide the path of the converters. They engage the tissue penetrating member and/or delivery member (directly or indirectly) to produce the desired motion. They are desirably configured to convert motion of the spring along its longitudinal axis into orthogonal motion of the tissue penetrating member and/or delivery member though conversion in other directions is also contemplated. The motion converters can have a wedge, trapezoidal or curved shape with other shapes also contemplated. In particular embodiments, the first motion converter can have a trapezoidal shape and include a slot which engages a pin on the tissue penetrating member that rides in the slot. The slot can have a trapezoidal shape that mirrors or otherwise corresponds to the overall shape of the converter and serves to push the tissue penetrating member during the upslope portion of the trapezoid and then pull it back during the down slope portion. In one variation, one or both of the motion converters can comprise a cam or cam like device which is turned by the spring and engages the tissue penetrating and/or delivery member.

In other variations, the actuating mechanism can also comprise an electro-mechanical device/mechanism such as a solenoid, or a piezoelectric device. In one embodiment, the piezoelectric device can comprise a shaped piezoelectric element which has a non-deployed and deployed state. This element can be configured to go into the deployed state upon the application of a voltage and then return to the non-deployed state upon the removal of the voltage. This and related embodiments allow for a reciprocating motion of the actuating mechanism so as to both advance the tissue penetrating member and then withdraw it.

The release element is coupled to at least one of the actuating mechanism or a spring coupled to the actuating mechanism. In particular embodiments, the release element is coupled to a spring positioned within the capsule so as to retain the spring in a compressed state. Degradation of the release element releases the spring to actuate the actuation mechanism. In many embodiments, the release element comprises a material configured to degrade upon exposure to chemical conditions in the small or large intestine such as pH. Typically, the release element is configured to degrade upon exposure to a selected pH in the small intestine, e.g., 6.0, 6.3, 6.5, 6.7, 7.0, 7.1, 7.2, 7.3, 7.4, 8.0 or greater. However, it can also be configured to degrade in response to other conditions in the small intestine, e.g., the presence of various enzymes. In particular embodiments, the release element can be configured to degrade in response to particular chemical conditions in the fluids in the small intestine such as those which occur after ingestion of a meal (e.g., a meal high in fats or proteins).

Biodegradation of the release element from one or more conditions in the small intestine (or other location in the GI tract) can be achieved by selection of the materials for the release element, the amount of cross linking of those materials as well as the thickness and other dimensions of the release elements. Lesser amounts of cross linking and or thinner dimensions can increase the rate of degradation and vice versa. Suitable materials for the release element can comprise biodegradable materials such as various enteric materials which are configured to degrade upon exposure to the higher pH or other condition in the small intestine. The enteric materials can be copolymerized or otherwise mixed with one or more polymers to obtain a number of particular material properties in addition to biodegradation. Such properties can include without limitation stiffness, strength, flexibility and hardness.

In particular embodiments, the release element can comprise a film or plug that fits over or otherwise blocks the guide tube and retains the tissue penetrating member inside the guide tube. In these and related embodiments, the tissue penetrating member is coupled to a spring loaded actuating mechanism such that when the release element is degraded sufficiently, it releases the tissue penetrating member which then springs out of the guide tube to penetrate into the intestinal wall. In other embodiments, the release element can be shaped to function as a latch which holds the tissue penetrating element in place. In these and related embodiments, the release element can be located on the exterior or the interior of the capsule. In the interior embodiments, the capsule and guide tubes are configured to allow for the ingress of intestinal fluids into the capsule interior to allow for the degradation of the release element.

In some embodiments, the actuating mechanism can be actuated by means of a sensor, such as a pH or other chemical sensor which detects the presence of the capsule in the small intestine and sends a signal to the actuating mechanism (or to an electronic controller coupled to the actuating mechanism to actuate the mechanism). Embodiments of a pH sensor can comprise an electrode-based sensor or it can be a mechanically-based sensor such as a polymer which shrinks or expands upon exposure to the pH or other chemical conditions in the small intestine. In related embodiments, an expandable/contractible sensor can also comprise the actuating mechanism itself by using the mechanical motion from the expansion or contraction of the sensor.

According to another embodiment for detecting that the swallowable device is in the small intestine (or other location in the GI tract), the sensor can comprise a strain gauge or other pressure/force sensor for detecting the number of peristaltic contractions that the capsule is being subject to within a particular location in the intestinal tract. In these embodiments, the capsule is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments detection of the number of peristaltic contractions can be used to not only determine if the capsule is in the small intestine but the relative location within the intestine as well.

As an alternative or supplement to internally activated drug delivery, in another aspect of the invention, the user may externally activate the actuating mechanism to deliver drug by means of RF, magnetic or other wireless signaling means known in the art. In these and related embodiments, the user can use a handheld device (e.g., a hand held RF device) which not only includes signaling means, but also means for informing the user when the device is in the small intestine or other location in the GI tract. The later embodiment can be implemented by including an RF transmitter on the swallowable device to signal to the user when the device is in the small intestine or other location (e.g., by signaling an input from the sensor). The same handheld device can also be configured to alter the user when the actuating mechanism has been activated and the selected drug(s) delivered. In this way, the user is provided confirmation that the drug has been delivered. This allows the user to take other appropriate drugs/therapeutic agents as well as make other related decisions (e.g., for diabetics to eat a meal or not and what foods should be eaten). The handheld device can also be configured to send a signal to the swallowable device to over-ride the actuating mechanism and so prevent, delay or accelerate the delivery of drug. In use, such embodiments allow the user to intervene to prevent, delay or accelerate the delivery of drug based upon other symptoms and/or patient actions (e.g., eating a meal, deciding to go to sleep, exercise etc).

The user may also externally activate the actuating mechanism at a selected time period after swallowing the capsule. The time period can be correlated to a typical transit time or range of transit times for food moving through the user's GI tract to a particular location in the tract such as the small intestine.

Another aspect of the inventions provides therapeutic agent preparations for delivery into the wall of the small intestine (or other wall of a lumen in the intestinal tract) using embodiments of the swallowable device described herein. The preparation comprises a therapeutically effective dose of at least one therapeutic agent (e.g., insulin, an anti-seizure compound, NSAIDs, an antibiotic, etc). It may comprise a solid, liquid or combination of both and can include one or more pharmaceutical excipients. The preparation has a shape and material consistency to be contained in embodiments of the swallowable capsule, delivered from the capsule into the lumen wall and degrade within the lumen wall to release the dose of therapeutic agent. The preparation may also have a selectable surface area to volume ratio so as enhance or otherwise control the rate of degradation of the preparation in the wall of the small intestine or other body lumen. In various embodiments, the preparation can be configured to be coupled to an actuator such as a release element (and/or other components coupled to the release element) which has a first configuration in which the preparation is contained in the capsule and a second configuration in which the preparation is advanced out of the capsule and into the wall of the small intestine. The dose of the drug or other therapeutic agent in the preparation can be titrated downward from that which would be required for conventional oral delivery methods so that potential side effects from the drug can be reduced.

Typically, though not necessarily, the preparation will be shaped and otherwise configured to be contained in the lumen of a tissue penetrating member, such as a hollow needle which is configured to be advanced out of the capsule and into the wall of the small intestine. Also, as described herein, in various embodiments, the preparation itself may comprise a tissue penetrating member shaped and configured to be advanced into the wall of the small intestine or other lumen in the intestinal tract.

Another aspect of the invention provides methods for the delivery of drugs and the therapeutic agents into the walls of the GI tract using embodiments of the swallowable drug delivery devices. Such methods can be used for the delivery of therapeutically effective amounts of a variety of drugs and other therapeutic agents. These include a number of large molecule peptides and proteins which would otherwise require injection due to chemical breakdown in the stomach e.g., growth hormone, parathyroid hormone, insulin, interferons and other like compounds. Suitable drugs and other therapeutic agents which can be delivered by embodiments of the invention include various chemotherapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents, immune suppression agents and anti parasitic agents such as various anti malarial agents. The dosage of the particular drug can be titrated for the patient's weight, age, condition or other parameter.

In various method embodiments, embodiments of the swallowable drug delivery device can be used to deliver a plurality of drugs for the treatment of multiple conditions or for the treatment of a particular condition (e.g., a mixture of protease inhibitors for treatment HIV AIDS). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream at about the same time. Due to differences in chemical makeup, molecular weight, etc, drugs can be absorbed through the intestinal wall at different rates, resulting in different pharmacokinetic distribution curves. Embodiments of the invention address this issue by injecting the desired drug mixtures at about the same time. This in turn, improves the pharmacokinetics and thus, the efficacy of the selected mixture of drugs.

In one embodiment, an ingestible device is suitable for swallowing into a lumen of a gastrointestinal tract of a patient. The lumen has a wall. The device comprises a capsule sized to pass through the intestinal tract. A therapeutic agent preparation is disposable in the capsule. The preparation comprises at least one therapeutic agent and the therapeutic agent preparation would chemically degrade or impose a deleterious effect on the patient if released within the lumen of the gastrointestinal tract. An actuator is coupled to the therapeutic agent preparation and has a first configuration and a second configuration. The preparation being retained within the capsule when the actuator is in the first configuration and the preparation is advanced from the capsule and into the lumen wall by movement of the actuator from the first configuration to the second configuration such that the deleterious effect or chemical degradation of the therapeutic agent in the lumen is inhibited.

In another embodiment, a method for delivering a therapeutic agent into the wall of a small intestine of a patient comprises swallowing a drug delivery capsule device including a therapeutic agent, a release element and a tissue penetrating member. The therapeutic agent would chemically degrade or impose a deleterious effect on the patient if released within a lumen of the gastrointestinal tract. The release element is released in the small intestine responsive to a condition in the small intestine; and the therapeutic agent is delivered into the wall of the small intestine using the tissue penetrating member such that the deleterious effect or degradation of the therapeutic agent in the lumen is inhibited.

In yet another embodiment, a swallowable device for inserting a therapeutic agent preparation into the intestinal wall of a patient's intestinal tract comprises a swallowable capsule sized to pass through the intestinal tract. The capsule has a capsule wall including an aperture. At least a portion of the capsule wall comprises a material or coating which overlies the aperture and protects the capsule from degradation in the stomach and degrades in response to the pH in the small intestine. A tissue penetrating member includes a therapeutic agent preparation and a means for advancing the tissue penetrating member from the capsule through the aperture and into the intestinal wall of the patient responsive to a selected pH in the intestine.

In another embodiment, a swallowable device for delivering a therapeutic agent preparation into the intestinal wall of a patient's intestinal tract comprises a swallowable capsule sized to pass through the intestinal tract. The capsule has a capsule wall including an aperture. An expandable member is disposed within capsule in at least a partially non expanded state. The expandable member includes a first portion and a second portion separated by a separation valve which degrades upon exposure to a selected pH in the intestine. The first portion includes a liquid and the second portion includes a reactant configured to react with the liquid to produce a gas which expands the expandable member when the valve degrades. The liquid from the first portion mixes with the reactant in the second portion, to produce the gas which expands the expandable member. A tissue penetrating member is formed at least in part from a therapeutic agent preparation, the tissue penetrating member, including a proximal and distal portion. The proximal portion is detachably coupled to the expandable member. The tissue penetrating member includes at least one retaining feature for retaining the tissue penetrating member within the intestinal wall. Upon expansion of the expandable member, the tissue penetrating member is advanced through the aperture into the intestinal wall where it is retained by the at least one retaining feature so as to detach from the expandable member.

In still another embodiment, a swallowable device for delivering a therapeutic agent preparation into the intestinal wall of a patient's intestinal tract comprises a swallowable capsule sized to pass through the intestinal tract. The capsule has a capsule wall including an aperture. An expandable member is disposed within capsule in at least a partially non expanded state. The expandable member includes a first portion and second portion separated by a separation valve which degrades upon exposure to a selected pH in the intestine. The first portion includes a liquid, the second portion includes a reactant configured to react with the liquid to produce a gas which expands the expandable member when the valve degrades the liquid from the first portion mixes with the reactant in the second portion, to produce the gas which expands the expandable member. A tissue penetrating member has a lumen and a proximal and a distal portion. The proximal portion is coupled to the expandable member such that upon expansion of the expandable member, the tissue penetrating member is advanced through the aperture into the intestinal wall. At least one reservoir stores a therapeutic agent preparation. The reservoir is fluidicallly coupled to tissue penetrating member lumen. The reservoir is configured and positioned within the capsule to be collapsible by expansion of the expandable member to eject the therapeutic agent from the reservoir through the lumen and into the intestinal wall.

In another embodiment, a swallowable device for delivering a drug into the intestinal wall comprises a capsule sized to pass through the intestinal tract. A tissue penetrating member is positioned in the capsule and contains the drug. The tissue penetrating member has a tissue penetrating end for penetrating the intestinal wall. A delivery member delivers the drug from the tissue penetrating member into tissue. An actuating mechanism is coupled to at least one of the tissue penetrating member or the delivery member. The actuating mechanism configured to advance the tissue penetrating member into the intestinal wall and advance the delivery member to deliver the drug. A release element is operatively coupled to the actuating mechanism, the release element comprising a material configured to degrade upon exposure to a selected pH in the intestine such that upon degradation, the actuating mechanism is actuated to release the tissue penetrating member and advance the advanceable member to deliver drug into the intestinal wall.

In yet another embodiment, a method of drug delivery comprises swallowing a drug delivery device comprising a capsule, a drug, an actuating mechanism, a release element and a tissue penetrating member. The release element is released in the small intestine responsive to a condition in the small intestine and the actuation mechanism is actuated to deliver the drug into the wall of the small intestine using the tissue penetrating member.

Further details of these and other embodiments and aspects of the invention are described more fully below, with reference to the attached drawing figures.

BRIEF DESCRIPTION OF THE DRAWINGS

FIGS. 8a-8c are side view illustrating positioning of the drug delivery device in the small intestine and deployment of the tissue penetrating members to deliver drug; FIG. 8a shows the device in the small intestine prior to deployment of the tissue penetrating members with the release element in tact; FIG. 8b shows the device in the small intestine with the release element degraded and the tissue penetrating elements deployed; and FIG. 8c shows the device in the small intestine with the tissue penetrating elements retracted and the drug delivered.

FIG. 14a shows the balloon in a non-inflated state with the separation valve closed; FIG. 14b shows the balloon with valve open and mixing of the chemical reactants; and FIG. 14c shows the balloon in an inflated state.

FIG. 16a shows the balloon in a non-inflated state with the capsule coating intact and the separation valve closed; FIG. 16b shows the capsule coating degraded and resulting ingress of intestinal fluid into the capsule interior to make contact with the isolation valve; and FIG. 16c shows the degradation and opening of the isolation valve from contact with intestinal fluid.

FIG. 17b shows is a top view of the embodiment of FIG. 17a.

FIG. 18 shows an embodiment of a separation valve comprising a collar valve

FIG. 22b is a lateral view showing an embodiment of a platform having multiple advancement members and tissue penetrating members.

FIG. 23a shows the balloon in a non inflated state and FIG. 23b shows the balloon inflated with the penetrating members deployed.

FIG. 24a shows the balloon in a non inflated state and FIG. 24b shows the balloon inflated and the penetrating members placed in a distributed pattern within the intestinal wall.

FIG. 25a shows the balloon in a non inflated state, and FIG. 25b shows the balloon inflated with drug injected from the reservoir into the intestinal wall.

FIG. 27a shows the valve in the closed position and FIG. 27b shows the valve in the open position.

FIG. 28a shows the valve in the closed position and FIG. 28b shows the valve in the open position.

FIGS. 29a-29b, show an embodiment of a capsule having tearable seams arranged in a radial or lateral pattern for tearing of the capsule by inflation of the expandable balloon; FIG. 29a shows the capsule prior to inflation and FIG. 29b shows the capsule broken into pieces by the inflation of the balloon.

DETAILED DESCRIPTION OF THE INVENTION

Figure 1A:
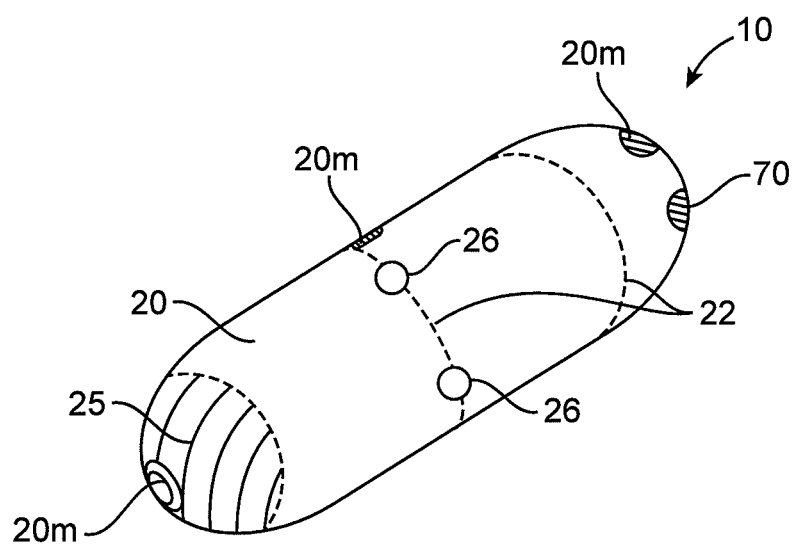
FIG. 1a is a lateral viewing showing an embodiment of a swallowable drug delivery device.

Embodiments of the invention provide devices, systems and methods for delivering medications in to various locations in the body. As used herein, the term "medication" refers to a medicinal preparation in any form which can include drugs or other therapeutic agents as well as one or more pharmaceutical excipients. Many embodiments provide a swallowable device for delivering medication within the GI tract. Particular embodiments provide a swallowable device such as a capsule for delivering medications to the wall of the small intestine or other GI organ.

Referring now to FIGS. 1-11, embodiments of a device 10 for the delivery of medication 100 to a delivery site DS in the intestinal tract, comprises a capsule 20 including at least one aperture 26, an expandable member 30, guide tube 30, and one or more tissue penetrating members 40 containing a medication 100. The tissue penetrating member 40 can be formed at least in part from medication 100, and/or contain a section or compartment 42 formed from or containing medication 100 that is integral with the tissue penetrating member 40 positioned or otherwise advanceable in the at least one guide tube, a delivery member 50, an actuating mechanism 60 and release element 70. Medication 100 also described herein as preparation 100, typically comprises at least one drug or therapeutic agent 101 and may include one or more pharmaceutical excipients known in the art.

Device 10 including tissue penetrating member 40 can be configured for the delivery of liquid, semi-liquid or solid forms of medication 100 or all three. Solid forms of medication/preparation 100 can include both powder or pellet. Semi liquid can include a slurry or paste. Whatever the form, medication/preparation 100 desirably has a shape and material consistency allowing the medication to be advanced out of the device, into the intestinal wall (or other luminal wall in the GI tract) and then degrade in the intestinal wall to release the drug or other therapeutic agent 101. The material consistency can include one or more of the hardness, porosity and solubility of the preparation (in body fluids). The material consistency can be achieved by one or more of the following: i) the compaction force used to make the preparation; ii) the use of one or more pharmaceutical disintegrants known in the art; iii) use of other pharmaceutical excipients; iv) the particle size and distribution of the preparation (e.g., micronized particles); and v) use of micronizing and other particle formation methods known in the art. Suitable shapes for preparation 100 can include cylindrical, cubical, rectangular, conical, spherical, hemispherical and combinations thereof. Also, the shape can be selected so as to define a particular surface area and volume of preparation 100 and thus, the ratio between the two. The ratio of surface area to volume can in turn, be used to achieve a selected rate of degradation within the intestinal or other lumen wall. Larger ratios (e.g., larger amounts of surface area per unit volume) can be used to achieve faster rates of degradation and vice versa. In particular embodiments, the surface area to volume ratio can be in the range of about 1:1 to 100:1, with specific embodiments of 2:1, 5:1, 20:1, 25:1, 50:1 and 75:1. Medication/preparation 100 will typically be pre-packed within a lumen 44 of tissue penetrating members 40, but can also be contained at another location within an interior 24 of capsule 20, or in the case of a liquid or semi-liquid, within an enclosed reservoir 27. The medication can be pre-shaped to fit into the lumen or packed for example, in a powder form. Typically, the device 10 will be configured to deliver a single drug 101 as part of medication 100. However in some embodiments, the device 10 can be configured for delivery of multiple drugs 101 including a first second, or a third drug which can be compounded into a single or multiple medications 100. For embodiments having multiple medications/drugs, the medications can be contained in separate tissue penetrating members 40 or within separate compartments or reservoirs 27 within capsule 20. In another embodiment, a first dose 102 of medication 100 containing a first drug 101 can be packed into the penetrating member(s) 40 and a second dose 103 of medication 100 (containing the same or a different drug 101) can be coated onto the surface 25 of capsule as is shown in the embodiment of FIG. 1a. The drugs 101 in the two doses of medication 102 and 103 can be the same or different. In this way, a bimodal pharmacokinetic release of the same or different drugs can be achieved. The second dose 103 of medication 100 can have an enteric coating 104 to ensure that it is released in the small intestine and achieve a time release of the medication 100 as well. Enteric coating 104 can include one or more enteric coatings described herein or known in the art.

Figure 1B:
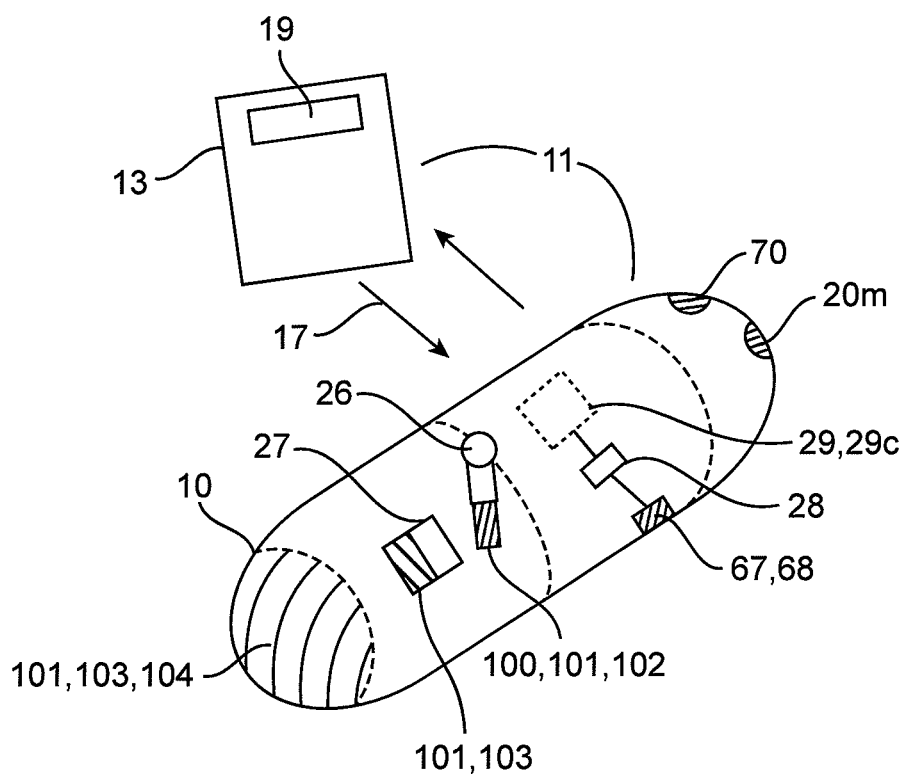
FIG. 1b is a lateral viewing showing an embodiment of a system including a swallowable drug delivery device.
Figure 1C:
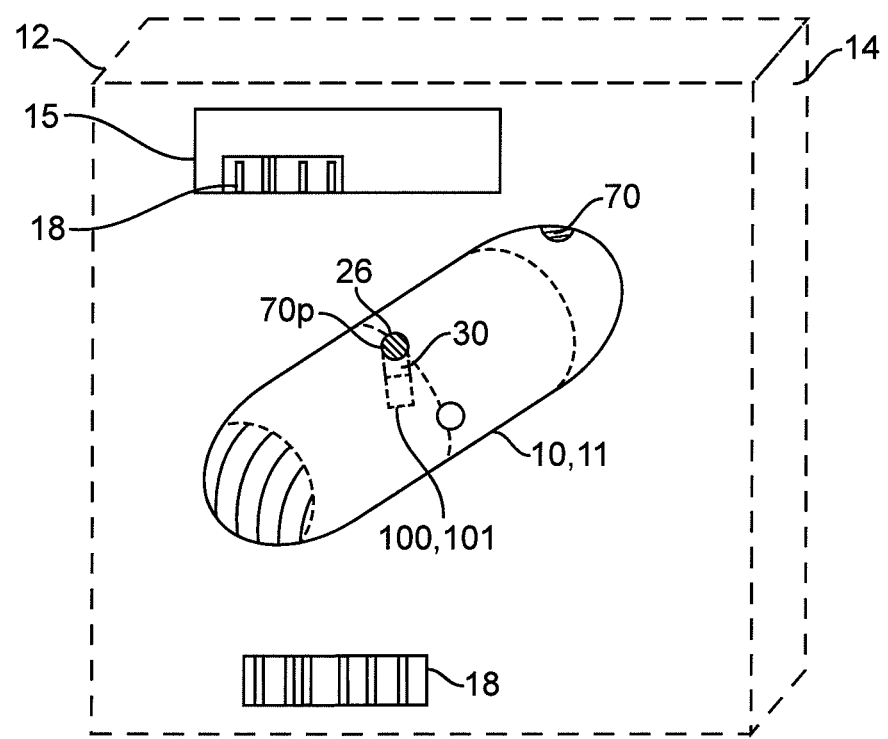
FIG. 1c is a lateral viewing showing an embodiment of a kit including a swallowable drug delivery device and a set of instructions for use.
Figure 1D:
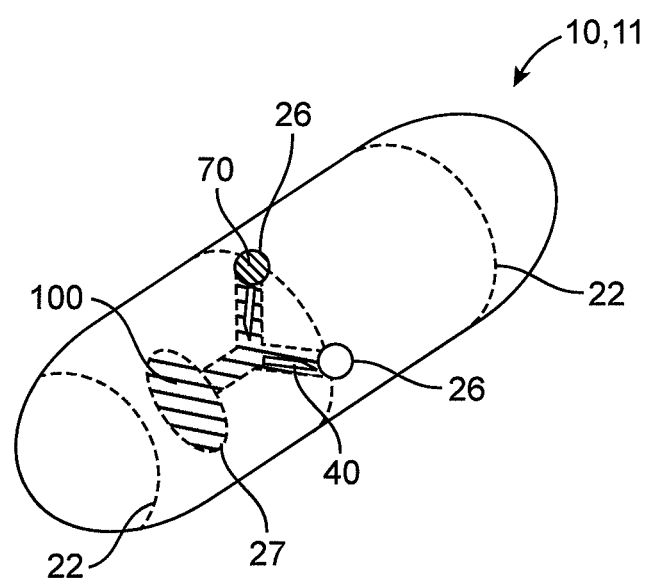
FIG. 1d is a lateral viewing showing an embodiment of a swallowable drug delivery device including a drug reservoir.

A system 11 for delivery of medication 100 into the wall of the small intestine or other location within the GI tract, may comprise device 10, containing one or more medications 100 for the treatment of a selected condition or conditions. In some embodiments, the system may include a hand held device 13, described herein for communicating with device 10 as is shown in the embodiment of FIG. 1b. System 11 may also be configured as a kit 14 including system 11 and a set of instructions for use 15 which are packaged in packaging 12 as is shown in the embodiment of FIG. 1c. The instructions can indicate to the patient when to take the device 10 relative to one or more events such as the ingestion of a meal or a physiological measurement such as blood glucose, cholesterol, etc. In such embodiments, kit 14 can include multiple devices 10 containing a regimen of medications 100 for a selected period of administration, e.g., a day, week, or multiple weeks depending upon the condition to be treated.

Capsule 20 is sized to be swallowed and pass through the intestinal tract. The size can also be adjusted depending upon the amount of drug to be delivered as well as the patient's weight and adult vs. pediatric applications. Typically the capsule will have a tubular shape with curved ends similar to a vitamin. In these and related embodiment, capsule lengths 20L can be in the range of 0.5 to 2 inches and diameters 20D in the range of 0.1 to 0.5 inches with other dimensions contemplated. The capsule 20 includes a capsule wall 21w, having an exterior surface 25 and an interior surface 24 defining an interior space or volume 24v. The capsule wall 21w includes volume 24 and an outer surface 25 having one or more apertures 26 sized for the outward advancement of tissue penetrating members 40. via guide tubes 30. In addition to the other components of device 10, (e.g., the expandable member, actuation mechanism etc.) the interior volume can include one or more compartments or reservoirs 27.

One or more portions of capsule 20 can be fabricated from various biocompatible polymers known in the art, including various biodegradable polymers which in a preferred embodiment can comprise PGLA (polylactic-co-glycolic acid). Other suitable biodegradable materials include various enteric materials described herein as well as lactide, glycolide, lactic acid, glycolic acid, para-dioxanone, caprolactone, trimethylene carbonate, caprolactone, blends and copolymers thereof.

Use of biodegradable materials for capsule 20, including biodegradable enteric materials allows the capsule to degrade in whole or part to facilitate passage through the GI system after drug deliver. As is described in further detail herein, in various embodiments, capsule 20 can include seams 22 of bio-degradable material so as to controllably degrade into smaller pieces 23 which are more easily passed through the intestinal tract.

Additionally, in various embodiments, the capsule 20 can include various radio-opaque or echogenic materials for location of the device using fluoroscopy, ultrasound or other medical imaging modality. In specific embodiments, all or a portion of the capsule can include radio-opaque/echogenic markers 20m as is shown in the embodiment of FIGS. 1a and 1b. In use, such materials not only allow for the location of device 10 in the GI tract, but also allow for the determination of transit times of the device through the GI tract.

Expandable member 30 can comprise a variety of expandable devices shaped and sized to fit within capsule 20, but will typically comprise an expandable balloon 30. Other suitable expandable members include various shape memory devices, and/or chemically expandable polymer devices having an expanded shape and size corresponding to the interior volume 24v of the capsule 20. For ease of discussion, expandable member 30 will now be referred to as balloon 30, but other embodiments are equally applicable. Balloon 30 will typically be attached to an interior surface 24 of the capsule 20 in at least a partially non-expanded state. Means of attachment can include the use of various adhesive known in the medical device arts. The balloon can be packed inside capsule 20 in a furled or other compact configuration to conserve space within the interior portion of the capsule. Furling may be achieved by placement of separation valve 50 over a selected portion of the un-inflated balloon 30. In a particular embodiments, furling can be facilitated by the use of a collar type separation valve 55 described herein that is placed around the un-inflated balloon to hold in a furled configuration. In another approach, furling can also be achieved by the use of one or more pre-formed creases 30c placed along the balloon in a lateral, spiral or other configuration. In preferred embodiments, tissue penetrating members 40 are positioned within guide tubes 30 which serve to guide and support the advancement of members 40 into tissue such as the wall of the small intestine or other portion of the GI tract. In other embodiments, tissue penetrating members 40 can be positioned in capsule 20 without guide tubes. The tissue penetrating members 40 will typically comprise a hollow needle or other like structure and will have a lumen 44 and a tissue penetrating end 45 for penetrating a selectable depth into the intestinal wall IW. Member 40 may also include a pin 41 for engagement with a motion converter 90 described herein. The depth of penetration can be controlled by the length of member 40, the configuration of motion converter 90 described herein as well as the placement of a stop or flange 40s on member 40 which can, in an embodiment, correspond to pin 41 described herein. Medication 100 will typically be delivered into tissue through lumen 44. In many embodiments, lumen 44 is pre-packed with the desired medication 100 which is advanced out of the lumen using delivery member 50 or other advancement means (e.g. by means of force applied to a collapsible embodiment of member 40). As an alternative, medication 100 can be advanced into lumen 44 from another location/compartment in capsule 20. In some embodiments, all or a portion of the tissue penetrating member 40 can be fabricated from medication 100 itself. In these and related embodiments, the medication can have a needle or dart-like structure (with or without barbs) configured to penetrate and be retained in the intestinal wall such as the wall of the small intestine. The dart can be sized and shaped depending upon the medication, dose and desired depth of penetration into the intestinal wall. Medication 100 can be formed into darts, pellets or other shapes using various compression molding and other related methods known in the pharmaceutical arts.

Figure 7A:
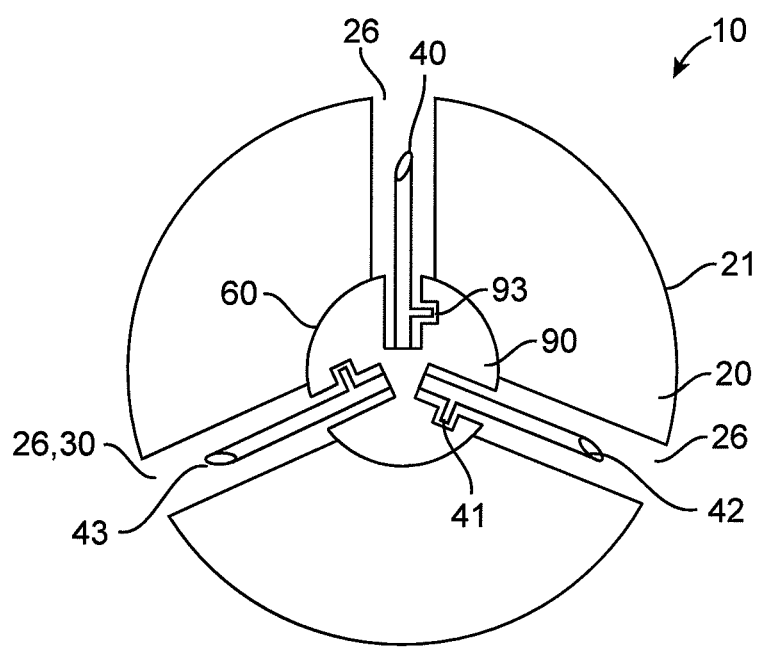
FIG. 7a is a cross sectional view illustrating an embodiment of the swallowable drug delivery device having a multiple tissue penetrating members and an actuating mechanism for advancing the tissue penetrating members.
Figure 7B:
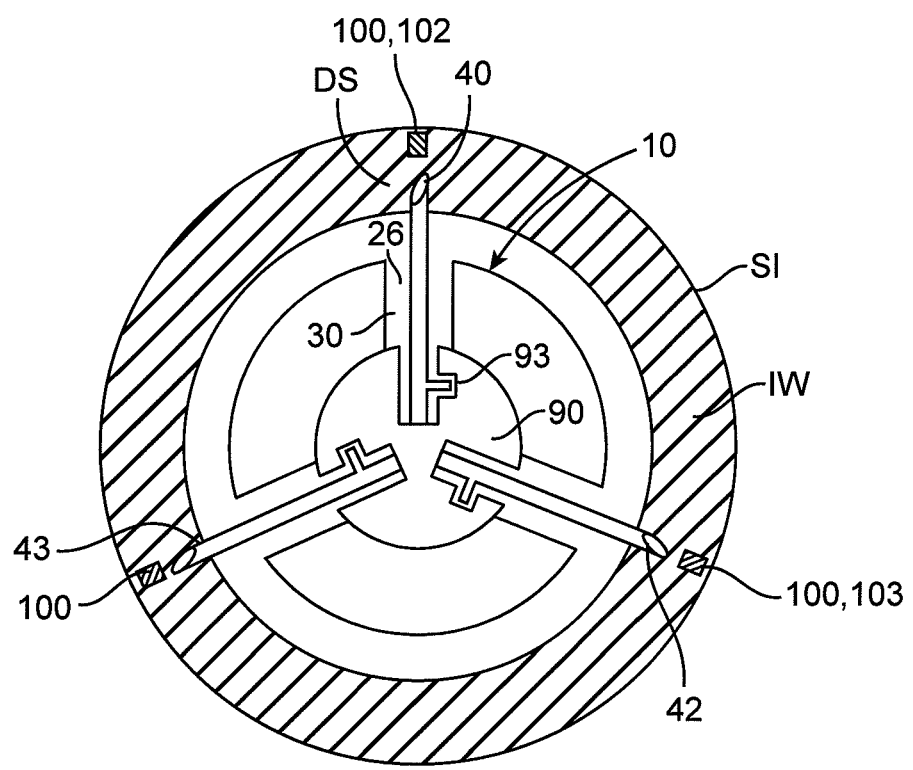
FIG. 7b is a cross sectional view illustrating deployment of the tissue penetrating members of the embodiment of FIG. 7a to deliver medication to a delivery site and anchor the device in the intestinal wall during delivery.
Figure 8B:
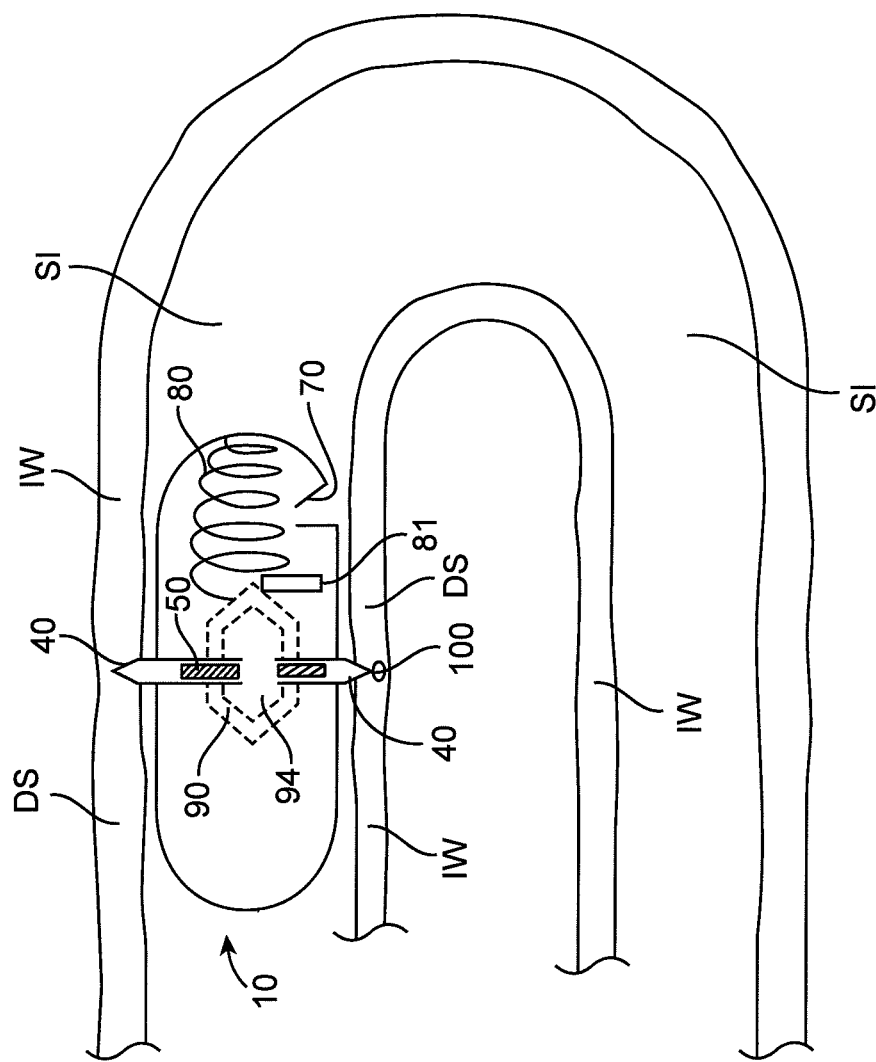
Figure 8C:
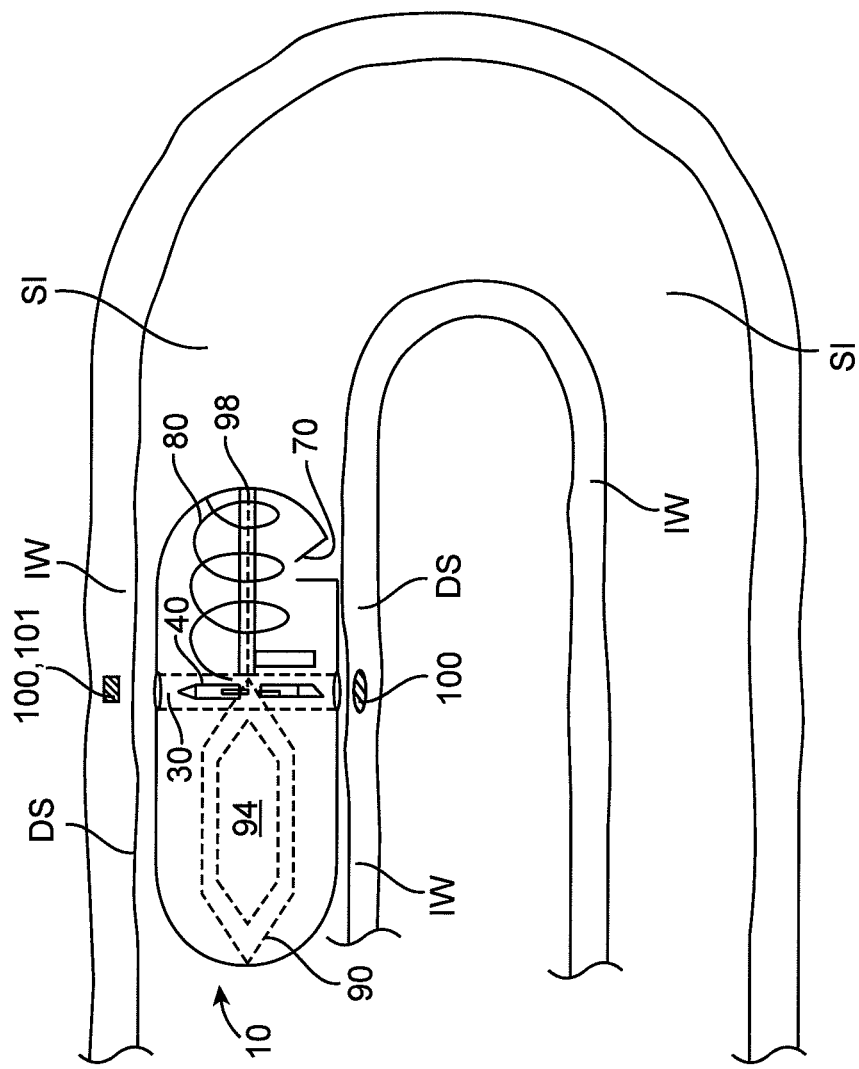

Balloon 30 can comprise various polymers known in the medical device arts, but preferably comprises non-compliant polymers such as PET (Polyethylene Teraphalate) and other non compliant materials known in the art. It can be fabricated using various balloon blowing methods known in the balloon catheters arts (e.g., mold blowing) to have a shape 30s and size which corresponds approximately to the interior volume 24v of capsule 20. Suitable shapes 30s for balloon 30 include various cylindrical shapes having tapered or curved end portions 31 (an example of such a shape including a hot dog). In some embodiments, the inflated size of balloon 30, including its diameter 30D can be slightly larger than capsule 20 so as to cause the capsule to come apart from the force of inflation, (e.g., due to hoop stress). Desirably, the walls 32 of balloon 30 will be thin and can have a wall thickness 33 in the range of 0.005 to 0.0001" more preferably, in the range of 0.001 to 0.0001, with specific embodiments of 0.002, 0.001, and 0.0005). In various embodiments, device 10 can include a second 42 and a third 43 tissue penetrating member 40 as is shown in the embodiments of FIGS. 7a and 7b, with additional numbers contemplated. Each tissue penetrating member 40 can be used to deliver the same or a different medication 100 as well as different doses of the same drug. In preferred embodiments, the tissue penetrating members 40 can be substantially symmetrically distributed around the perimeter 21 of capsule 20 so as to anchor the capsule onto the intestinal wall IW during delivery of medications 100. Anchoring capsule 20 in such a way reduces the likelihood that the capsule will be displaced or moved by peristaltic contractions occurring during delivery of the medication. In specific embodiments, the amount of anchoring force can be adjusted to the typical forces applied during peristaltic contraction of the small intestine. Anchoring can be further facilitated by configured some or all of tissue penetrating members 40 to have a curved or arcuate shape.

Figure 14A:
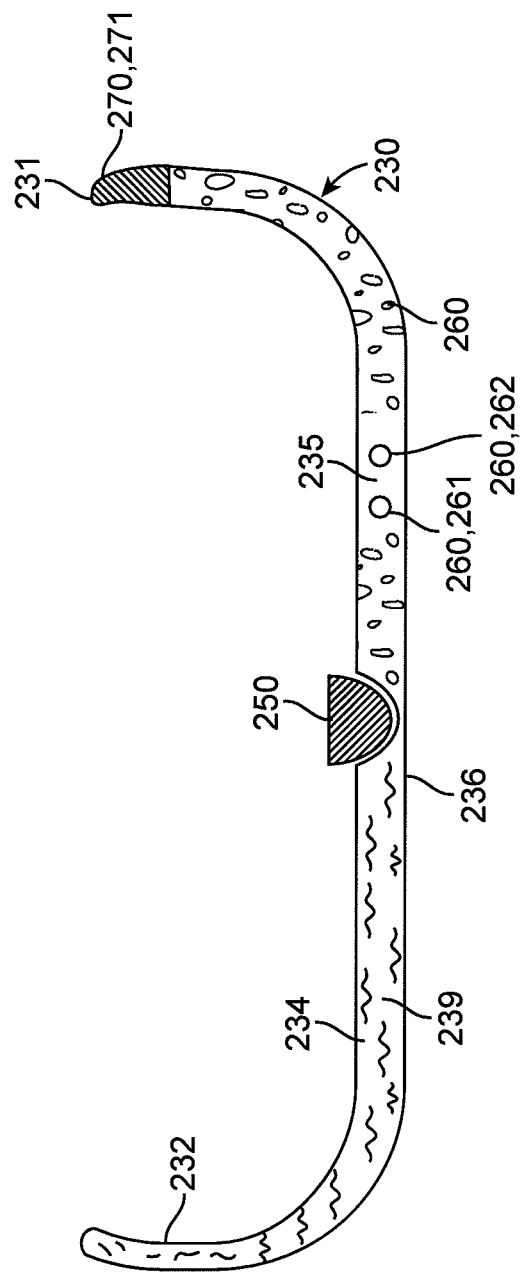
FIG. 14a-14c are lateral views illustrating inflation of the expandable balloon using chemical reactants.
Figure 14B:
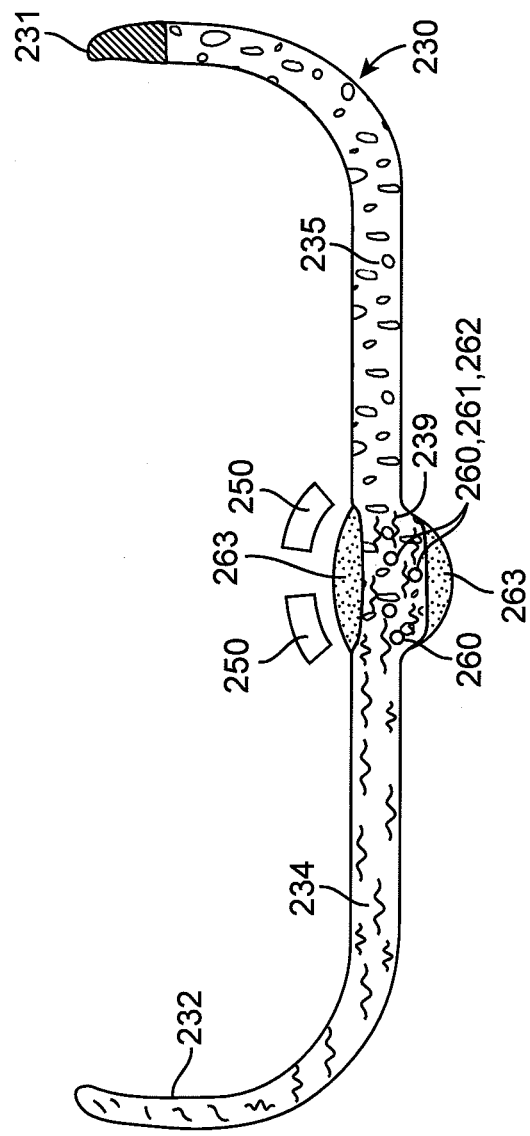
Figure 14C:
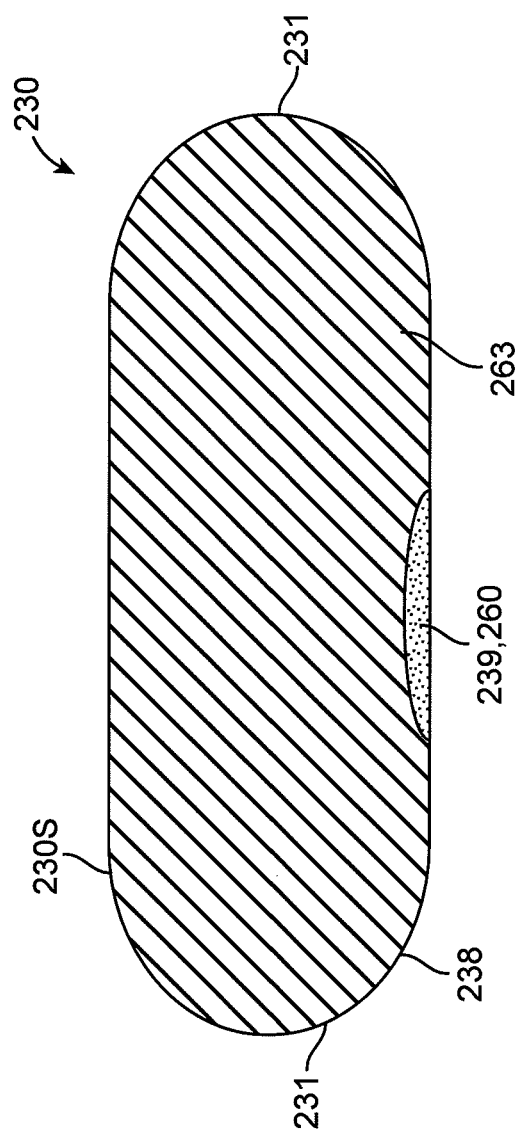

Balloon 230 also will typically include at least a first and a second portion or compartment 234 and 235 which are separated by a separation valve, delivery member, or other separation means which separates the contents of each compartment. In many embodiments, compartments 234 and 235 will have at least a small connecting section 236 between them which is where separation valve 250 will typically be placed. A liquid 239, typically water, can be disposed within first compartment 234 and one or more reactants 260 disposed in second compartment 235 (which typically are solid though liquid may also be used) as is shown in the embodiment of FIG. 14a. When valve 250 opens (e.g., from degradation caused by fluids within the small intestine) liquid 239 enters compartment 235 (or vice versa or both), the reactant(s) 260 mix with the liquid and produce a gas 263 such as carbon dioxide which expands balloon 230 as is shown in the embodiments of FIGS. 14b-14c. Expansion of balloon 230 is configured to advance medication 100 through the tissue penetrating member 240 into the intestinal wall IW as will be explained more fully herein. Accordingly, at least a portion of the delivery member 250 is advanceable within the tissue penetrating member lumen 244 and thus member 250 has a size and shape (e.g., a piston like shape) configured to fit within the delivery member lumen 244 or other chamber or compartment within tissue penetrating member 240.

Reactants 260 will typically include at least a first and a second reactant, 261 and 262 for example, an acid such as citric acid and a base such as sodium hydroxide. Additional numbers of reactants are also contemplated. For embodiments using citric acid and sodium hydroxide, the ratio's between the two reactants (citric acid to sodium hydroxide) can be in the range of 1:1 to 1:4, with a specific ratio of 1:2. Desirably, solid reactants 260 have little or no absorbed water. Accordingly, one or more of the reactants, such as sodium hydroxide can be pre-dried (e.g., by vacuum drying) before being placed within balloon 230. Other reactants 260 including other acids, e.g., ascetic acid and bases are also contemplated. The amounts of particular reactants 260, including combinations of reactants can be selected to produce particular pressures using known stoichiometric equations for the particular chemical reactions as well as the inflated volume of the balloon and the ideal gas law (e.g., PV=nRT).

In some embodiments, the distal end 50d of the delivery member (the end which is advanced into tissue) can have a plunger element 51 which advances the medication within the tissue penetrating member lumen 44 and also forms a seal with the lumen. Plunger element 51 can be integral or attached to delivery member 50. Preferably, delivery member 50 is configured to travel a fixed distance within the needle lumen 44 so as to deliver a fixed or metered dose of drug into the intestinal wall IW. This can be achieved by one or more of the selection of the diameter of the delivery member (e.g., the diameter can be distally tapered), the diameter of the tissue penetrating member (which can be narrowed at its distal end), use of a stop, and/or the actuating mechanism. However in some embodiments, the stroke or travel distance of member 50 can be adjusted in situ responsive to various factors such as one or more sensed conditions in the GI tract. In situ adjustment can be achieved through use of logic resource 29 (including controller 28c) coupled to an electro-mechanical embodiment of actuating mechanism 60. This allows for a variable dose of medication and/or variation of the distance the medication is injected into the intestinal wall.

Figure 15:
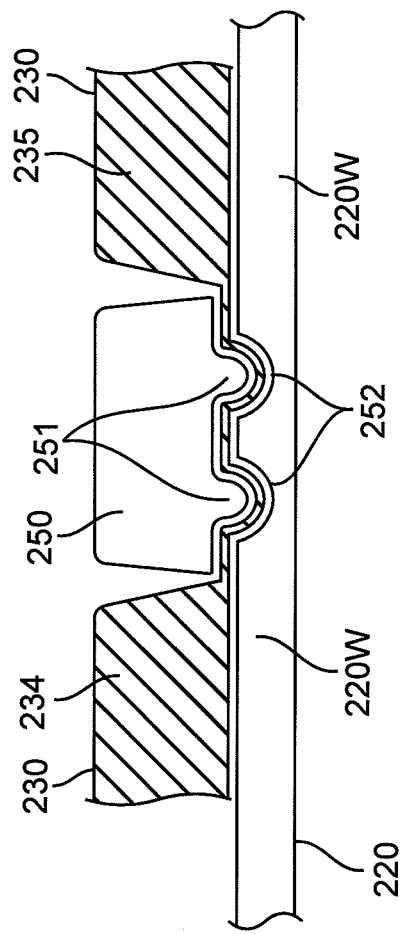
FIG. 15 shows an embodiment of a separation valve having pinching features.

Various embodiments of the invention provide a number of structures and configurations for a separation valve 250 or other separation means 250. As is described below, in one or more embodiments, valve 250 may comprise a beam like structure, or collar type valve. Still other structures are considered. In one or more of these embodiments, valve 250 can include one or more pinching features 251 such as a ridge which engages a depression or other mating feature 252 on the internal surface 224 of capsule 220 as is shown in the embodiment of FIG. 15. In use, pinching features 251 provide for the application of additional force on the balloon wall 232 beneath the pinching feature and redundancy to the seal. Valve 250 may include multiple pinching features 251 to create a seal under each feature.

Actuating mechanism 60 can be coupled to at least one of the tissue penetrating member 40 or delivery member 50. The actuating mechanism is configured to advance tissue penetrating member 40 a selectable distance into the intestinal wall IW as well as advance the delivery member to deliver medication 100 and then withdraw the tissue penetrating member from the intestinal wall. In various embodiments, actuating mechanism 60 can comprise a spring loaded mechanism which is configured to be released by release element 70. Suitable springs 80 can include both coil (including conical shaped springs) and leaf springs with other spring structures also contemplated. In particular embodiments, spring 80 can be substantially cone-shaped to reduce the length of the spring in the compressed state even to the point where the compressed length of the spring is about the thickness of several coils (e.g., two or three) or only one coil.

Also in various embodiments, separation valve 250 can be configured to open in a number of ways and responsive to a number of conditions within the GI tract. In many embodiments, the separation valve 250 will be configured to open by having one or more portions degrade in response to the higher pH or other conditions found within the small intestine such that upon degradation, the valve opens. As an alternative or additional approach, separation valve 250 may also be configured to open in response to compressive forces applied by a peristaltic contraction within the small intestine. In still another approach, separation valve 250 may be a time-release valve configured to open after a certain period of time after a trigger event, e.g., an activation step initiated by the patient such as the pealing of a tab or pressing of a button.

Figure 2:
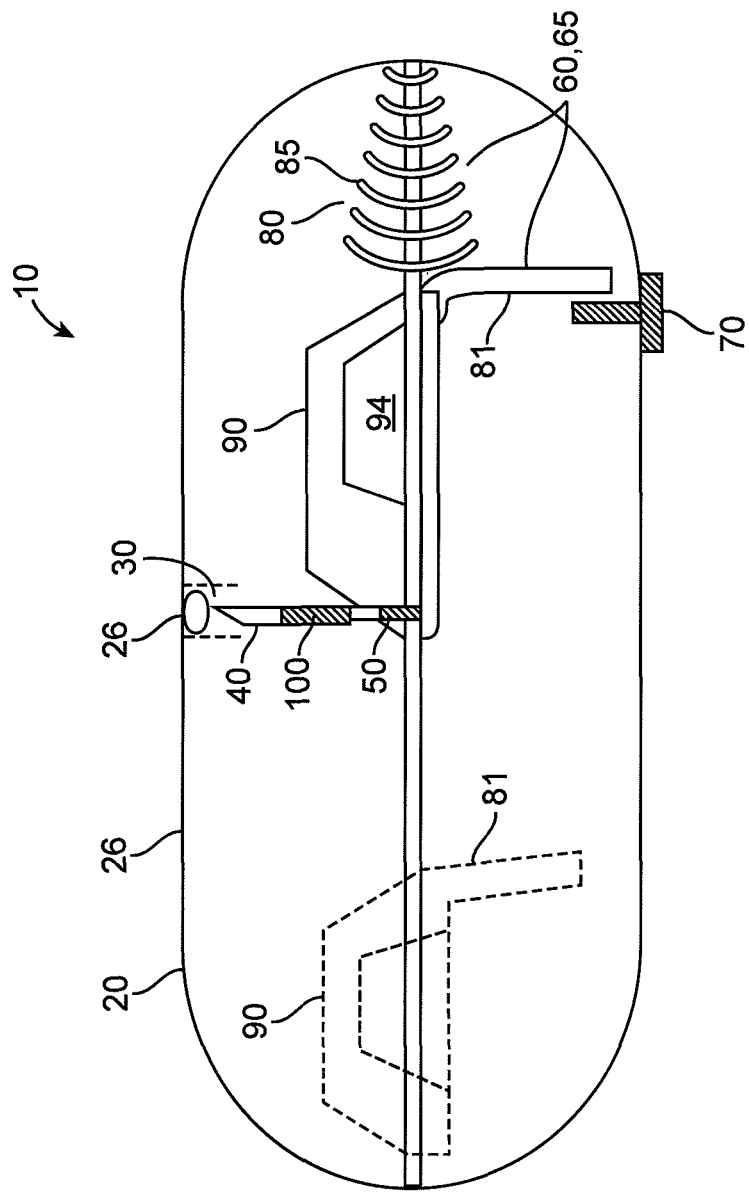
FIG. 2 is a lateral view illustrating an embodiment of the swallowable drug delivery device having a spring loaded actuation mechanism for advancing tissue penetrating members into tissue.
Figure 3:
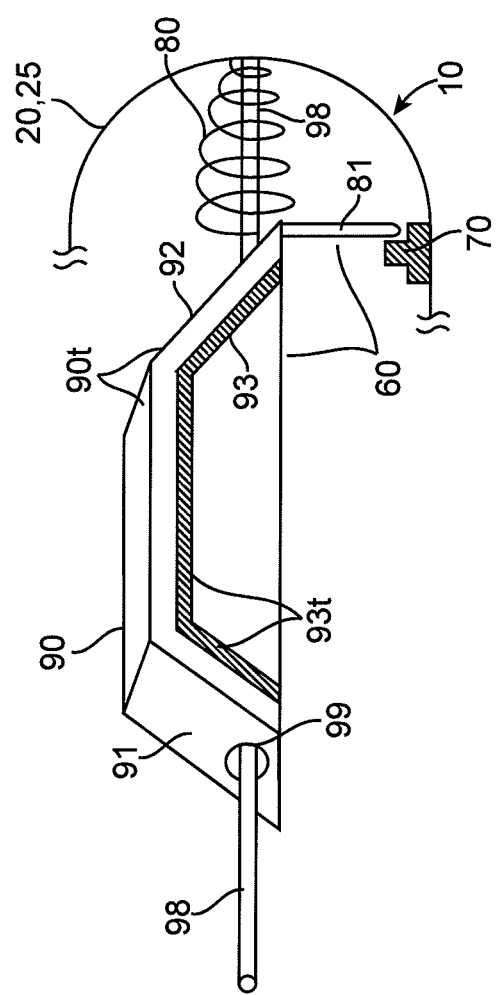
FIG. 3 is a lateral view illustrating an embodiment of the swallowable drug delivery device having a spring loaded actuation mechanism having a first motion converter.
Figure 4:
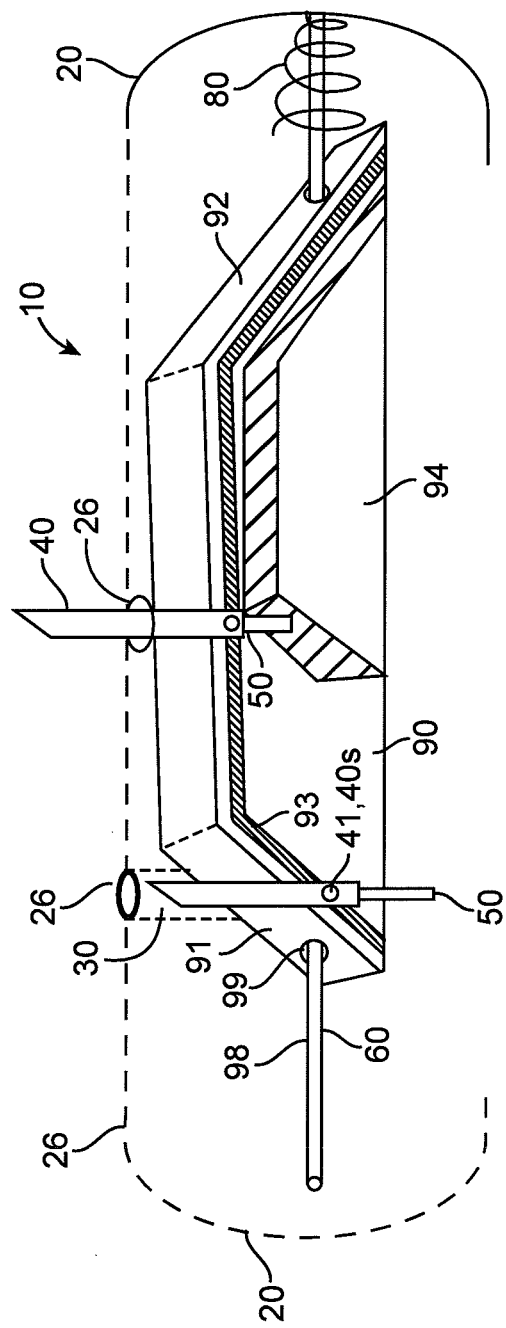
FIG. 4 is a lateral view illustrating an embodiment of the swallowable drug delivery device having a spring loaded actuation mechanism having first and a second motion converter.
Figure 5:
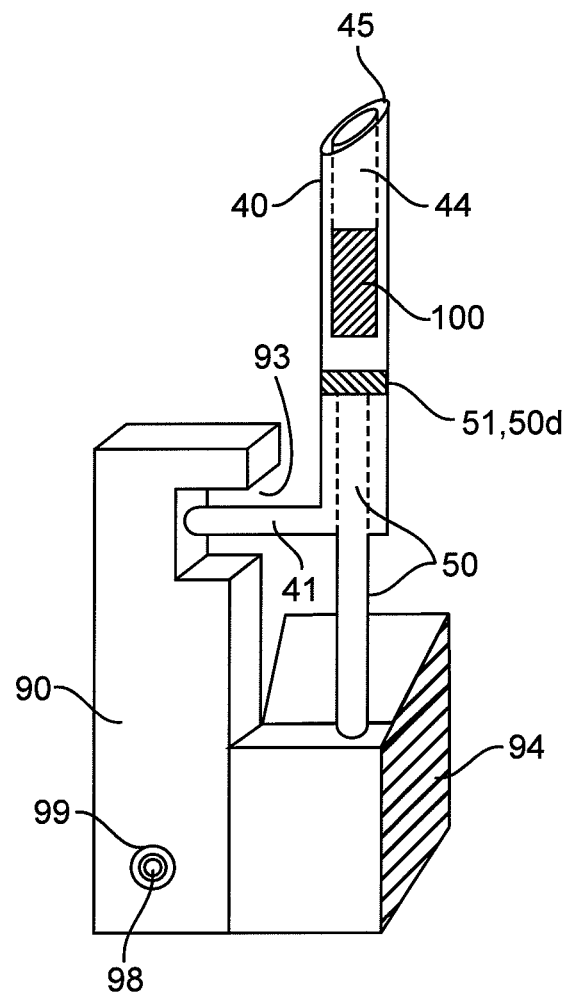
FIG. 5 is a perspective view illustrating engagement of the first and second motion converters with the tissue penetrating member and delivery members.
Figure 6:
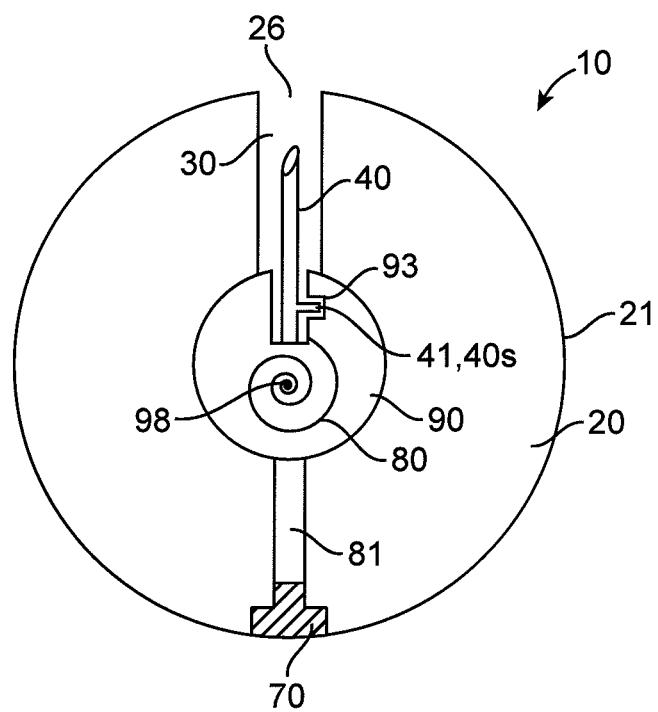
FIG. 6 is a cross sectional view illustrating an embodiment of the swallowable drug delivery device having a single tissue penetrating member and an actuating mechanism for advancing the tissue penetrating member.

In particular embodiments actuating mechanism 60 can comprise a spring 80, a first motion converter 90, and a second motion converter 94 and a track member 98 as is shown in the embodiments of FIGS. 2, 4 and 8a-8c. The release element 70 is coupled to spring 80 to retain the spring in a compressed state such that degradation of the release element releases the spring. Spring 80 may be coupled to release element 70 by a latch or other connecting element 81. First motion converter 90 is configured to convert motion of spring 80 to advance and withdraw the tissue penetrating member 40 in and out of the intestinal wall or other tissue. The second motion converter 94 is configured to convert motion of the spring 80 to advance the delivery member 50 into the tissue penetrating member lumen 44. Motion converters 90 and 94 are pushed by the spring and ride along a rod or other track member 98 which fits into a track member lumen 99 of converter 90. The track member 98 which serves to guide the path of the converters 90. Converters 90 and 94 engage the tissue penetrating member 40 and/or delivery member 50 (directly or indirectly) to produce the desired motion. They have a shape and other characteristics configured to convert motion of the spring 80 along its longitudinal axis into orthogonal motion of the tissue penetrating member 40 and/or delivery member 50 though conversion in other directions is also contemplated. The motion converters can have a wedge, trapezoidal or curved shape with other shapes also contemplated. In particular embodiments, the first motion converter 90 can have a trapezoidal shape 90t and include a slot 93 which engages a pin 41 on the tissue penetrating member that rides in the slot as is shown in the embodiments of FIGS. 2, 3 and 4. Slot 93 can also have a trapezoidal shape 93t that mirrors or otherwise corresponds to the overall shape of converter 90. Slot 93 serves to push the tissue penetrating member 40 during the upslope portion 91 of the trapezoid and then pull it back during the down slope portion 92. In one variation, one or both of the motion converters 90 and 94 can comprise a cam or cam like device (not shown). The cam can be turned by spring 80 so as to engage the tissue penetrating and/or delivery members 40 and 50. One or more components of mechanism 60 (as well as other components of device 10) including motion converters 90 and 94 can be fabricated using various MEMS-based methods known in the art so as to allow for selected amounts of miniaturization to fit within capsule 10.

Also as is described herein, they can be formed from various biodegradable materials known in the art.

Figure 16A:
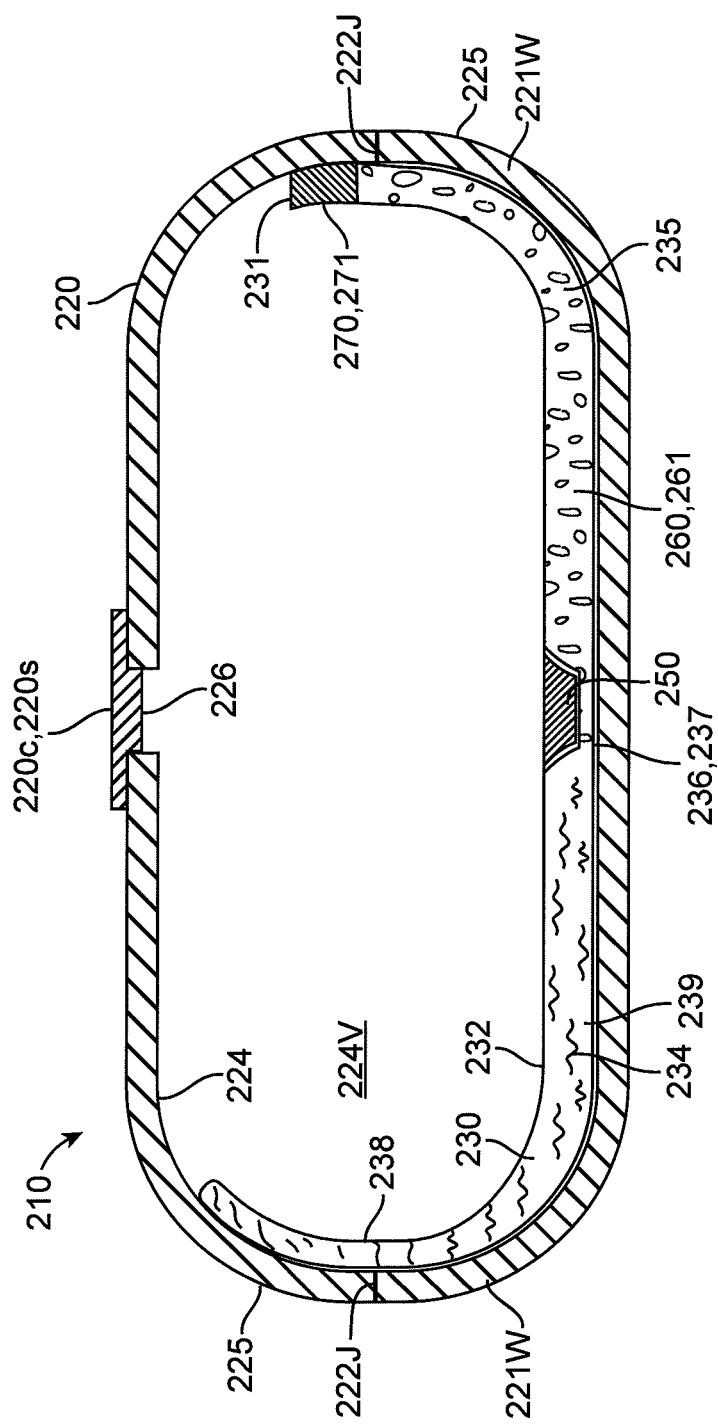
FIG. 16a-16c are lateral views illustrating use of a swallowable drug delivery device having a biodegradable coated capsule coating and a biodegradable separation valve to initiate inflation of the balloon in the small intestine.
Figure 16B:
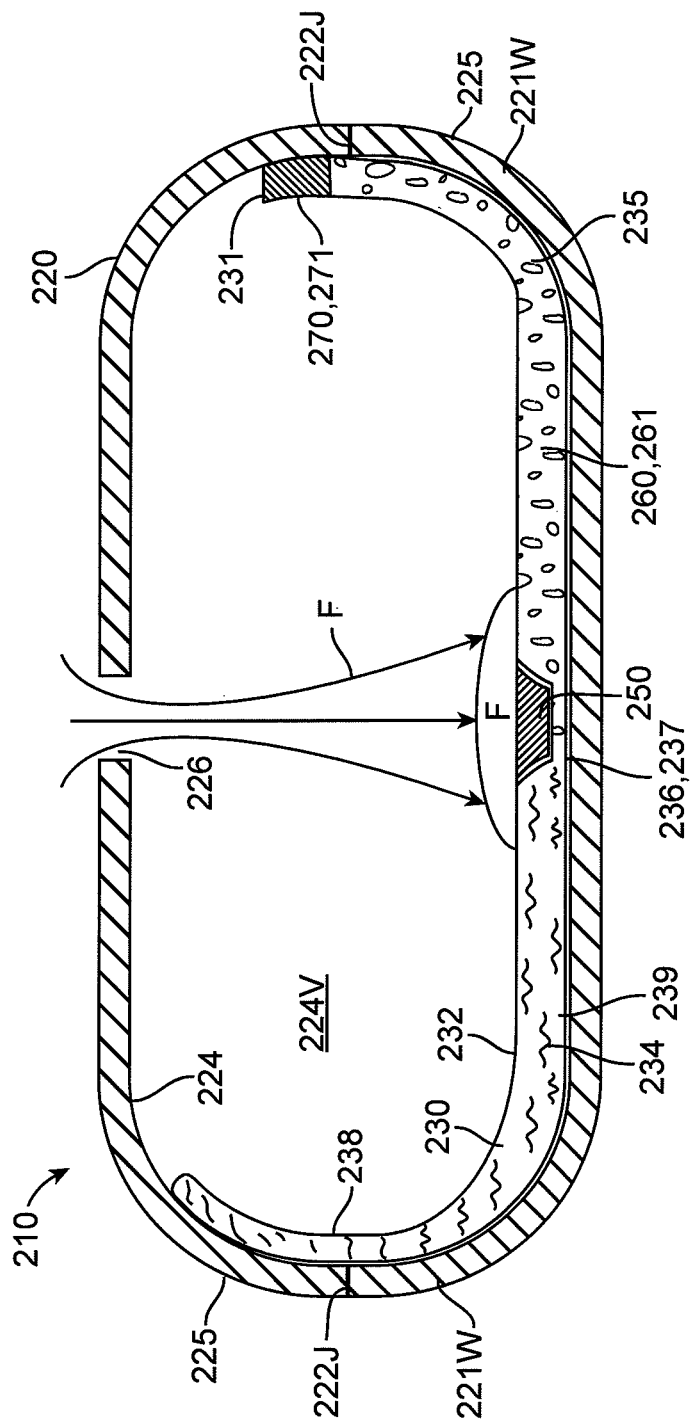
Figure 16C:
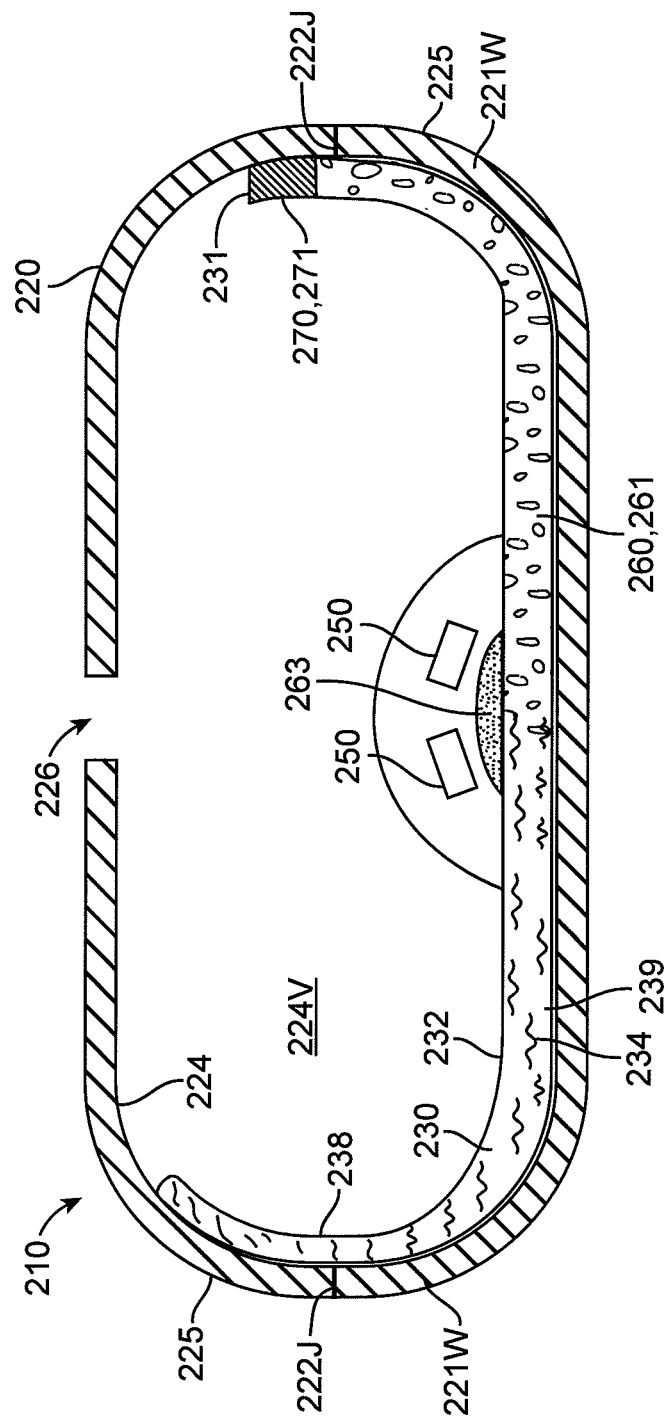

Embodiments of a degradable separation valve 250 can be positioned in a variety of locations on or within capsule 220 so as to exposed to and degraded by the intestinal fluids. While at least a portion of the valve may be exposed to the capsule exterior surface 225, typically, the valve will be positioned within the capsule interior 224v where it is exposed to intestinal fluids which enter through the at least one aperture 226 or other opening. In these and related embodiments, at least a portion of the capsule exterior surface 225 including the portion containing the at least one aperture 226 is desirably coated with a protective layer or coating 220c, such as an enteric coating which also degrades in response to pH or other conditions within the small intestine. Typically, the entire capsule will be so coated, however in some embodiments only a portion over apertures 226 will be coated. Such coatings provide a protective seal 226s over the at least one aperture 226 so that digestive fluids do not enter the capsule interior 224v and start to degrade the separation valve 250 until the capsule has reached the small intestine. The embodiments of FIGS. 16a-16c illustrate the sequence of degradation of the coating, ingress of intestinal or other fluid F into the capsule interior and subsequent degradation of the separation valve. In use, embodiments of device 210 employing a degradable coating 220c over the aperture 226 and a degradable valve 250 provide a primary and secondary seal for assuring that balloon 230 does not prematurely expand and deploy its tissue penetrating members 240 until capsule 220 has reached the small intestine.

In other variations, the actuating mechanism 60 can also comprise an electro-mechanical device/mechanism such as a solenoid, or a piezoelectric device. In one embodiment, a piezoelectric device used in mechanism 60 can comprise a shaped piezoelectric element which has a non-deployed and deployed state. This element can be configured to go into the deployed state upon the application of a voltage and then return to the non-deployed state upon the removal of the voltage. This and related embodiments allow for a reciprocating motion of the actuating mechanism 60 so as to both advance the tissue penetrating member and then withdraw it. The voltage for the piezoelectric element can be obtained generated using a battery or a piezoelectric based energy converter which generates voltage by mechanical deformation such as that which occurs from compression of the capsule 20 by a peristaltic contraction of the small intestine around the capsule. Further description of piezoelectric based energy converters is found in U.S patent application Ser. No. 12/556,524 which is fully incorporated by reference herein for all purposes. In one embodiment, deployment of tissue penetrating members 40 can in fact be triggered from a peristaltic contraction of the small intestine which provides the mechanical energy for generating voltage for the piezoelectric element.

Figure 17A:
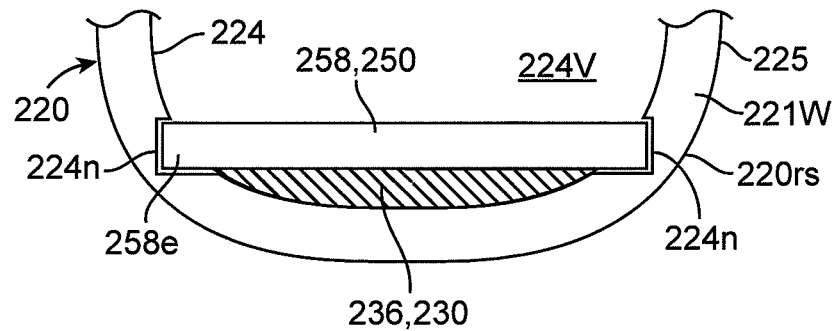
FIG. 17a shows is cross sectional view of an embodiment of a separation valve having a beam like structure.
Figure 17B:
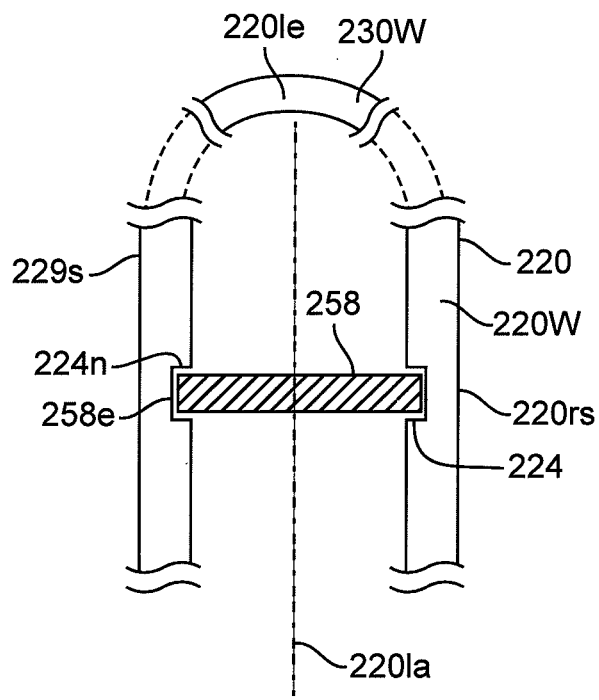

According to one or more embodiments, separation valve 250 may comprise a beam-like structure 258 that is placed within capsule 220 to compress and seal the portion of the balloon 236 between the first and second compartments 234 and 235 as is shown in the embodiment of FIGS. 17a and 17b. Beam 258 is desirably constructed of one more degradable materials described herein, e.g., PGLA, cellulose, etc. which degrade in response to the fluids found within the small intestine. When beam 258 degrades, the compressive forces of the balloon are released and contents from the first and second compartments 234 and 235 mix causing balloon expansion as described herein. Beam 258 can be attached at one or both sides of the interior surface 224 of the capsule. Typically, the beam will be placed proximate a central portion 236 of balloon 230, though other locations are also contemplated. In preferred embodiments, the beam 258 is positioned in radially oriented fashion with respect to balloon lateral axis 201a, attached to the radial sides 220rs of capsule interior surface 224 as is shown in the embodiment of FIGS. 17a and 17b. However, beam 258 may also be attached to the lateral ends 201e of the capsule interior surface. Preferably, in either of these two embodiments, beam 258 is attached to capsule interior surface 224 using an interference fit so that the beam can be snapped into place within the capsule using pick and place and other like methods known in the manufacturing arts. In specific embodiments, interior surface 224 can include notches 224n for placement of beam ends 258e to allow a snap or press fit of the beam 258 into the capsule 220.

Release element 70 will typically be coupled to the actuating mechanism 60 and/or a spring coupled to the actuating mechanism; however other configurations are also contemplated. In preferred embodiments, release element 70 is coupled to a spring 80 positioned within capsule 20 so as to retain the spring in a compressed state 85 as shown in the embodiment of FIG. 2. Degradation of the release element 70 releases spring 80 to actuate actuation mechanism 60. Accordingly, release element 70 can thus function as an actuator 70a (actuator 70a may also include (singularly or coupled to release element 70) spring 80 and other elements of mechanism 60). As is explained further below, actuator 70a has a first configuration where the therapeutic agent preparation 100 is contained within capsule 20 and a second configuration where the therapeutic agent preparation is advanced from the capsule into the wall of the small intestine or other luminal wall in the intestinal tract.

In many embodiments, release element 70 comprises a material configured to degrade upon exposure to chemical conditions in the small or large intestine such as pH. Typically, release element 70 is configured to degrade upon exposure to a selected pH in the small intestine, e.g., 7.0, 7.1, 7.2, 7.3, 7.4, 7.5, 7.6 8.0 or greater. The release element can also be configured to degrade within a particular range of pH such as, e.g., 7.0 to 7.5. In particular embodiments, the pH at which release element 70 degrades (defined herein as the degradation pH) can be selected for the particular drug to be delivered so as to release the drug at a location in small intestine which corresponds to the selected pH. Further, for embodiments of device 10 having multiple medications 100, the device can include a first release element 70 (coupled to an actuating mechanism for delivering a first drug) configured to degrade at first pH and a second release element 70 (coupled to an actuating mechanism for delivering a second drug) configured to degrade at a second pH (with additional numbers of release elements contemplated for varying number of drugs).

According to another embodiment shown in FIG. 18, the separation valve 250 can comprise a collar valve 255 including a connecting 236 of the expandable member 230 with an overlying constricting collar 255c made from biodegradable material. Collar 255c holds connection section 236 closed and releases it when the collar is degraded.

Release element 70 can also be configured to degrade in response to other conditions in the small intestine (or other GI location). In particular embodiments, the release element 70 can be configured to degrade in response to particular chemical conditions in the fluids in the small intestine such as those which occur after ingestion of a meal (e.g., a meal containing fats, starches or proteins). In this way, the release of medication 100 can be substantially synchronized or otherwise timed with the digestion of a meal. Such embodiments are particularly useful for the delivery of medication to control levels of blood sugar/glucose (e.g., insulin), serum cholesterol and serum triglycerides.

Figure 19A:
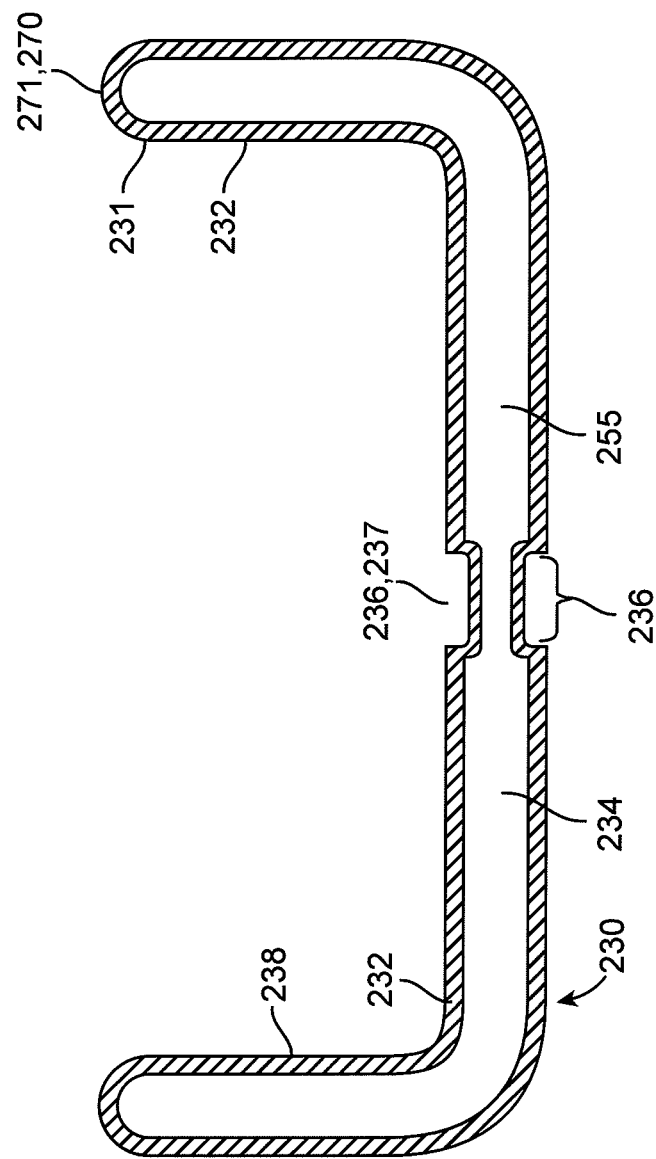
FIGS. 19a and 19b show an embodiment of the expandable balloon having a deflation valve comprising a biodegradable section of the balloon wall.
Figure 19B:
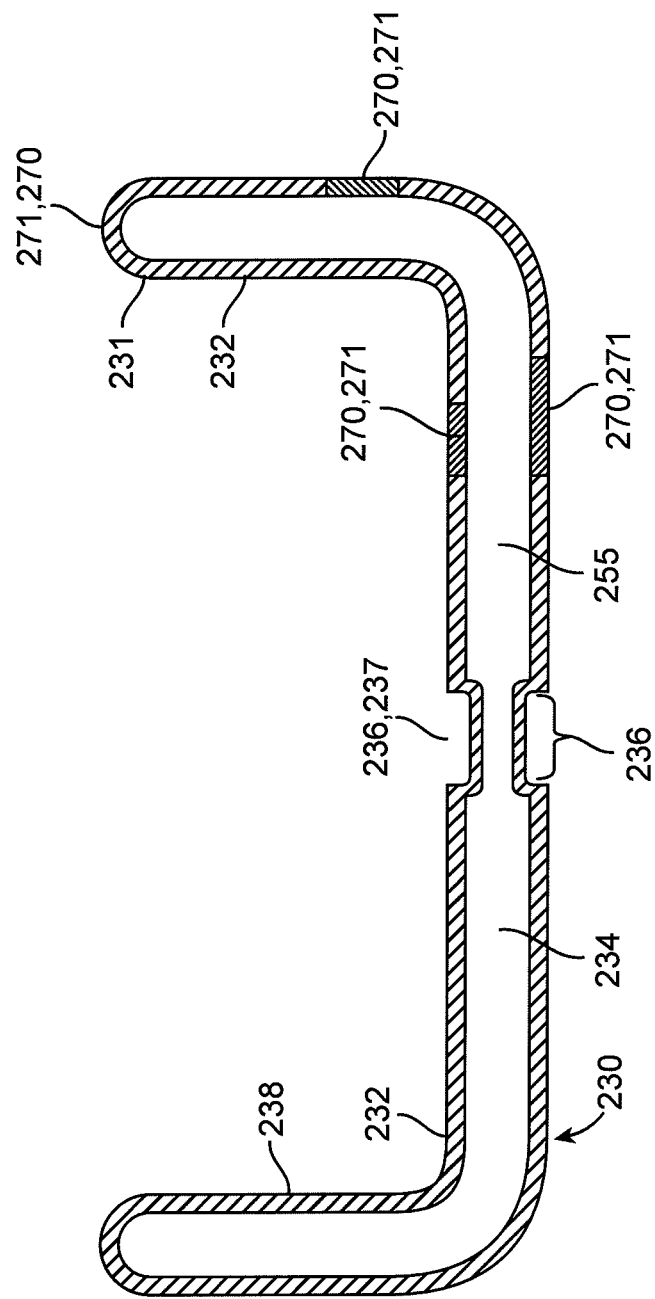

In addition to release valve 250, the balloon or other expandable member 230 will also typically include a deflation valve 270 which serves to deflate balloon 230 after inflation. Deflation valve 270 can comprise biodegradable materials which are configured to degrade upon exposure to the fluids in the small intestine and/or liquid in one of the compartments of the balloon so as to create an opening or channel for escape of gas within balloon. In one embodiment shown in FIG. 19a, the deflation valve 270 can comprise a biodegradable section 271 positioned on an end portion 231 of the balloon 230 so as to join opposing ends of the balloon wall 232 together. In this and related embodiments, when degradable section 271 degrades from exposure to the liquid, balloon wall 232 tears or otherwise comes apart providing for a high assurance of rapid deflation. Multiple degradable sections 271 can be placed at various locations within balloon wall 232 is shown in the embodiment of FIG. 19b, to provide an even higher degree of reliability in deflation. Desirably, sections 271 are only placed within the wall 232 of compartment 235. For embodiments where the deflation valve 270 is degraded by fluids within the small intestine, degradation of the valve can be facilitated by configuring inflated balloon 230 to break apart capsule 220 into two or more pieces so that large sections of the balloon are directly exposed to degrading fluids within the small intestine. This can be achieved by fabricating capsule 220 from separate parts (e.g., two halves mechanically fit together) and/or through the use of seams 222 in the capsule wall as is described herein.

Various approaches are contemplated for biodegradation of release element 70. In particular embodiments, biodegradation of release element 70 from one or more conditions in the small intestine (or other location in the GI tract) can be achieved by one or more of the following: i) selection of the materials for the release element, ii) the amount of cross linking of those materials; and iii) the thickness and other dimensions of the release element. Lesser amounts of cross linking and or thinner dimensions can increase the rate of degradation and visa versa. Suitable materials for the release element can comprise biodegradable materials such as various enteric materials which are configured to degrade upon exposure to the higher pH in the intestines. Suitable enteric materials include, but are not limited to, the following: cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters as well as other enteric materials known in the art. The selected enteric materials can be copolymerized or otherwise combined with one or more other polymers to obtain a number of other particular material properties in addition to biodegradation. Such properties can include without limitation stiffness, strength, flexibility and hardness.

Additionally, as further backup for insured deflation, one or more puncture elements 72 can be attached to the inside surface 24 of the capsule wall such that when the balloon fully deflates it is contacts and is punctured by the puncture element. Puncture elements 72 can comprise short protrusions from surface 24 having a pointed tip 73. In another alternative or additional embodiment of means for balloon deflation, one or more of the tissue penetrating members 40 can be directly coupled to balloon wall 32 and configured to tear away from the balloon when they detach, tearing the balloon wall in the process.

In alternative embodiments, the release element 70 can comprise a film or plug 70p that fits over or otherwise blocks guide tubes 30 and retains the tissue penetrating member 40 inside the guide tube (FIG. 1c). In these and related embodiments, tissue penetrating member 40 is coupled to a spring loaded actuating mechanism such that when the release element is degraded sufficiently, it releases the tissue penetrating member which then springs out of the guide tube to penetrate into the intestinal wall. In still other embodiments, release element 70 can be shaped to function as a latch which holds the tissue penetrating member 40 in place. In these and related embodiments, the release element can be located on the exterior or the interior of capsule 20. In the latter case, capsule 20 and/or guide tubes 30 can be configured to allow for the ingress of intestinal fluids into the capsule interior to allow for the degradation of the release element.

Figure 20A:
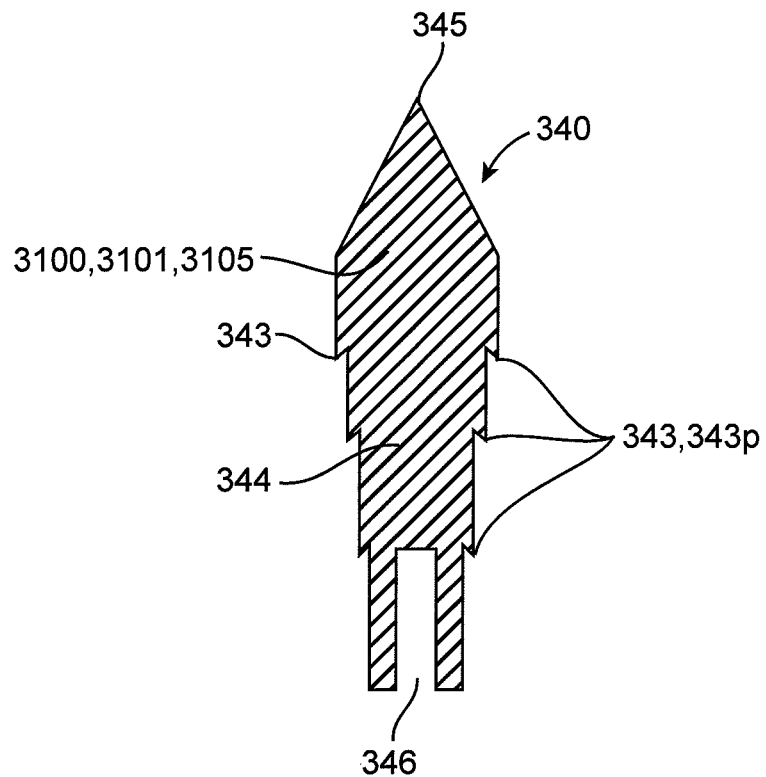
FIG. 20a is a side view of an embodiment of the tissue penetrating member.
Figure 20B:
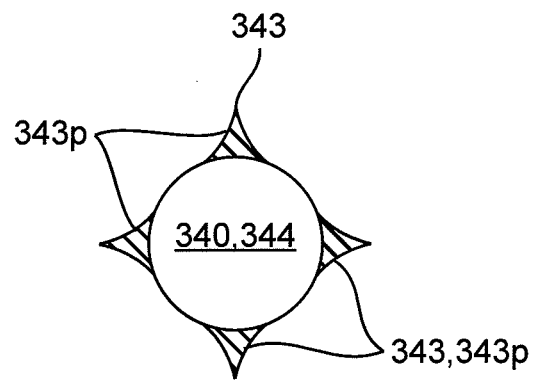
FIG. 20b is a bottom view of an embodiment of the tissue penetrating member illustrating placement of the tissue retaining features.
Figure 20C:
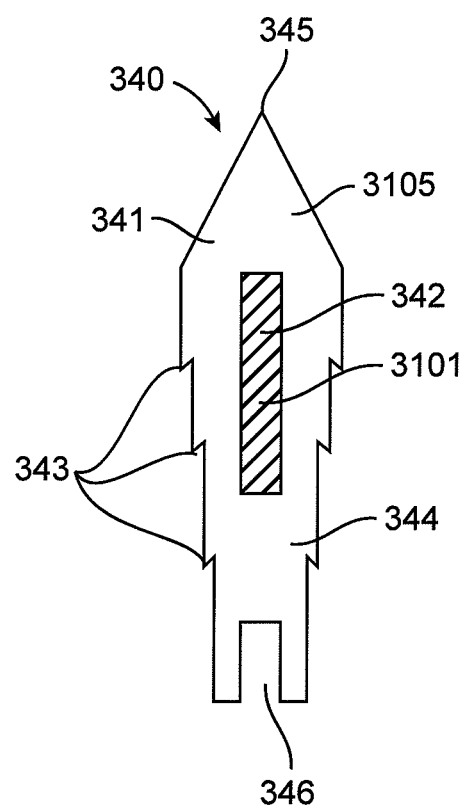
FIG. 20c is a side view of an embodiment of the tissue penetrating member having a separate drug containing section.

Tissue penetrating member 40 can be fabricated from various drugs and other therapeutic agents 101 as well as one or more biodegradable polymers to provide desired structural properties to the penetrating member (e.g., column strength) and/or control the release of drug. Referring now to FIGS. 20a-20c, in many embodiments, the penetrating member 40 can be formed to have a shaft 44 and a needle tip 45 or other pointed tip 45 so as to readily penetrate tissue of the intestinal wall as shown in the embodiment of FIG. 20a. Tip 45 may comprise degradable materials (within the body of the tip or as a coating), such as sucrose which increase the hardness and tissue penetrating properties of the tip. Once placed in the intestinal wall, the penetrating member 40 is degraded by the interstitial fluids within the wall tissue, the drug dissolves in those fluids and is absorbed into the blood stream. Penetrating member 40 will also typically include one or more tissue retaining features 43 such as a barb or hook to retain the penetrating member within the tissue of the intestinal wall after advancement. Retaining rememebers 43 can be arranged in various patterns 43p to enhance tissue retention such as two or more barbs symmetrically or otherwise distributed around and along member shaft 44 as is shown in the embodiments of FIGS. 20a and 20b. Additionally, in many embodiments, penetrating member will also include a recess or other mating feature 46 for attachment to a coupling component which attaches the penetrating member to the balloon (such as advancement member 80a described below).

As described above, tissue penetrating member 340 can be fabricated from a number of drugs and other therapeutic agents 3101. The penetrating member may be fabricated entirely from drug 3101 or may have other constituent components as well, e.g., various pharmaceutical excipients. Typically, the drug or other therapeutic agent 3101 will be mixed in with a biodegradable polymer 3105 such as PGLA, cellulose or other biodegradable material described herein or known in the art. In such embodiments, the penetrating member 340 may comprise a substantially heterogeneous mixture of drug 3101 and biodegradable polymer 3105. Alternatively, the penetrating member may 340 include a 341 portion formed substantially from biodegradable material 3105 and a separate section or compartment 342 that is formed from or contains drug 3101 as shown in the embodiment of FIG. 20c.

Tissue penetrating member 340 can be fabricated using one or more polymer and pharmaceutical fabrication techniques known in the art. For example, drug 3101 (with or without biodegradable material 3105) can be in solid form and then formed into the shape of the tissue penetrating member 340 using molding, compaction or other like method with one or more binding agents added. Alternatively, drug 3101 and/or drug preparation 3100 may be in solid or liquid form and then added to the biodegradable polymer 3105 in liquid form with the mixture then formed into the penetrating member 340 using molding or other forming method known in the polymer arts.

Desirably, embodiments of the tissue penetrating member 340 comprising a drug or other therapeutic agent 3101 and degradable polymer 3105 are formed at temperatures which do not produce any substantial thermal degradation of drug including drugs such as various peptides and proteins. This can be achieved through the use of room-temperature curing polymers and room temperature molding and solvent evaporation techniques known in the art. In particular embodiments, the amount of thermally degraded drug or other therapeutic agent within the tissue penetrating member is desirably less than about 10% by weight and more preferably, less than 5% and still more preferably less than 1%. The thermal degradation temperature(s) for a particular drug are either known or can be determined using methods known in the art and then this temperature can be used to select and adjust the particular polymer processing methods (e.g., molding, curing, solvent evaporation methods etc.) to minimize the temperatures and associated level of drug thermal degradation.

Tissue penetrating member 340 is desirably configured to be detachably coupled (directly or indirectly) to the balloon or other expandable member 330 so that after advancement of the tissue penetrating member 340 into the intestinal wall, the penetrating member detaches from the balloon. Detachability can be implemented by a variety of means including: i) the configuration and strength of the joint between penetrating member 340 and advancement member 380*a* (or other intermediary component(s) coupling member 340 to balloon 330); 2) the configuration and placement of tissue retaining features 343 on penetrating member 340; and iii) the depth of penetration of shaft 344 into the intestinal wall. Using one or more of these factors, penetrating member 340 be configured to detach as a result of balloon deflation (where the retaining features 343 hold the penetrating member in tissue as the balloon deflates or otherwise pulls back away from the intestinal wall) and/or the forces exerted on capsule 320 by a peristaltic contraction of the small intestine.

Figure 21A:
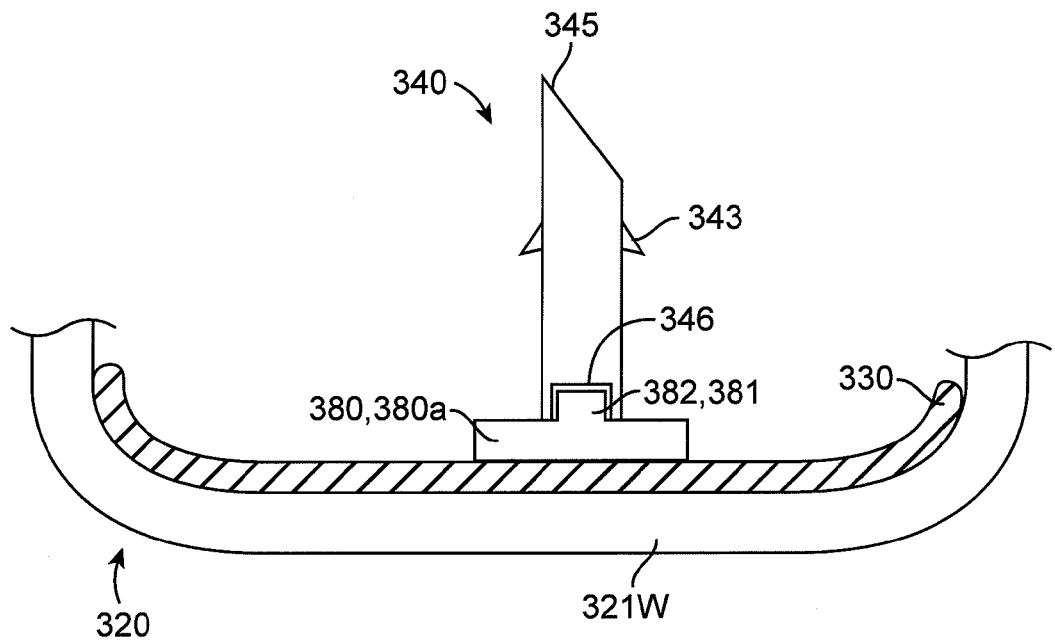
FIG. 21a is a lateral view showing use of an advancement member to couple the tissue penetrating member to the expandable balloon.
Figure 21B:
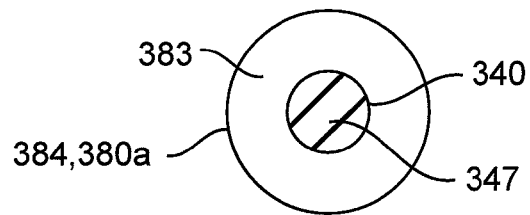
FIG. 21b is a bottom view showing an embodiment of an advancement member having a larger surface area than the tissue penetrating member so as to function as a force concentrating element.

Tissue penetrating member 340 can be directly or indirectly coupled to balloon 330. Referring now to FIGS. 21*a*-21*b* and 22, indirect coupling can be implemented using one or more coupling components 380 such as an advancement member 380*a*. Accordingly, in particular embodiments, the tissue penetrating member 340 may be coupled to balloon 330 by an advancement member 380*a* comprising a rigid structure attached to the balloon surface 338 which detachably engages the penetrating member 340. The advancement member 380*a* engages the penetrating member 340 by means of an attachment feature 381 such as a pin or other protrusion 382 (integral or attached to member 380*a*) which fits into a recess or other mating feature 346 of the penetrating member as is shown in the embodiment of FIG. 21*a*. The pin 382 and recess 346 can be configured to detach from the force of balloon deflation and/or force applied to capsule 320 by peristaltic contraction. In many embodiment, advancement member 380*a* can have a larger horizontal surface area 383 than the surface area 347 of penetrating member 340 so as to function as a force concentration element 384 as is shown in the embodiment of FIG. 21*b*. In use force concentration element 384 functions to increase the force per unit area applied to the penetrating member from expansion of balloon 330 or other expandable member.

Figure 22A:
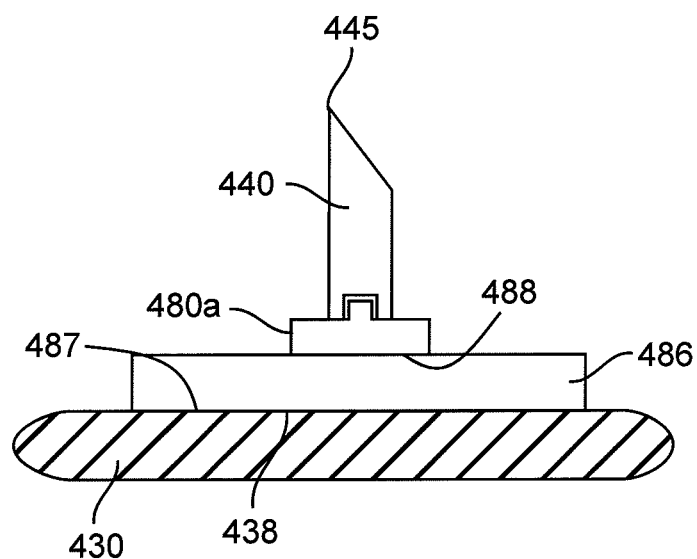
FIG. 22a is a lateral view showing use of an advancement member and an underlying platform to couple one or more tissue penetrating members to the expandable balloon.

In some embodiments, the advancement member 480*a* can be coupled to the balloon 430 via a support member 486 as is shown in the embodiments of FIGS. 22*a* and 22*b*. Support member 486 may correspond to a platform 486 having one surface 487 attached to the balloon surface 438 and the other surface 488 attached to the advancement member 480*a* (one or both of these attachments can be an adhesive attachment) as is shown in the embodiment of FIG. 22*a*. Platform 486 is desirably rigid, can have a plate-like structure and can be sized to allow for attachment and advancement of multiple advancement members 480*a* and tissue penetrating members 440 at the same time as is shown in the embodiment of FIG. 22*b*. For example, in particular embodiments, three, four or five groups of advancement and tissue penetrating members can be attached to platform 486, with additional numbers contemplated. In such embodiments, the platform may include a recess 489 for positioning of isolation valve 450.

Figure 23A:
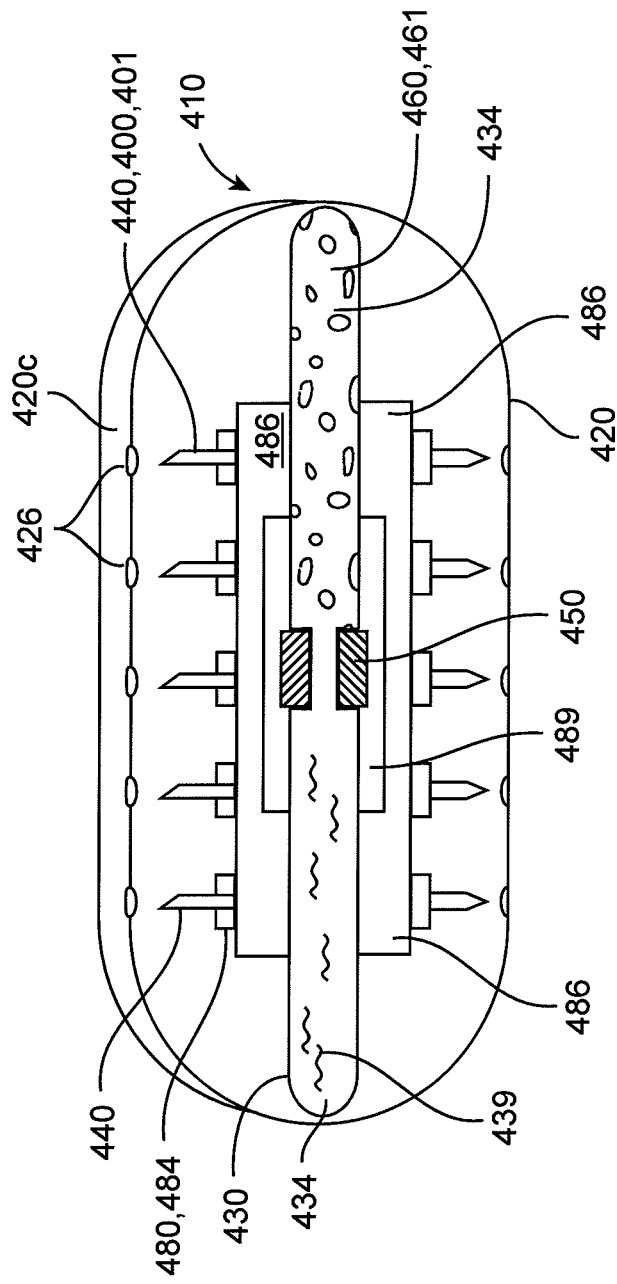
FIGS. 23a and 23b are lateral views illustrating use of an embodiment of a swallowable device having platforms and tissue penetrating members placed on opposite sides of the balloon to achieve bilateral deployment of the tissue penetrating members.
Figure 23B:
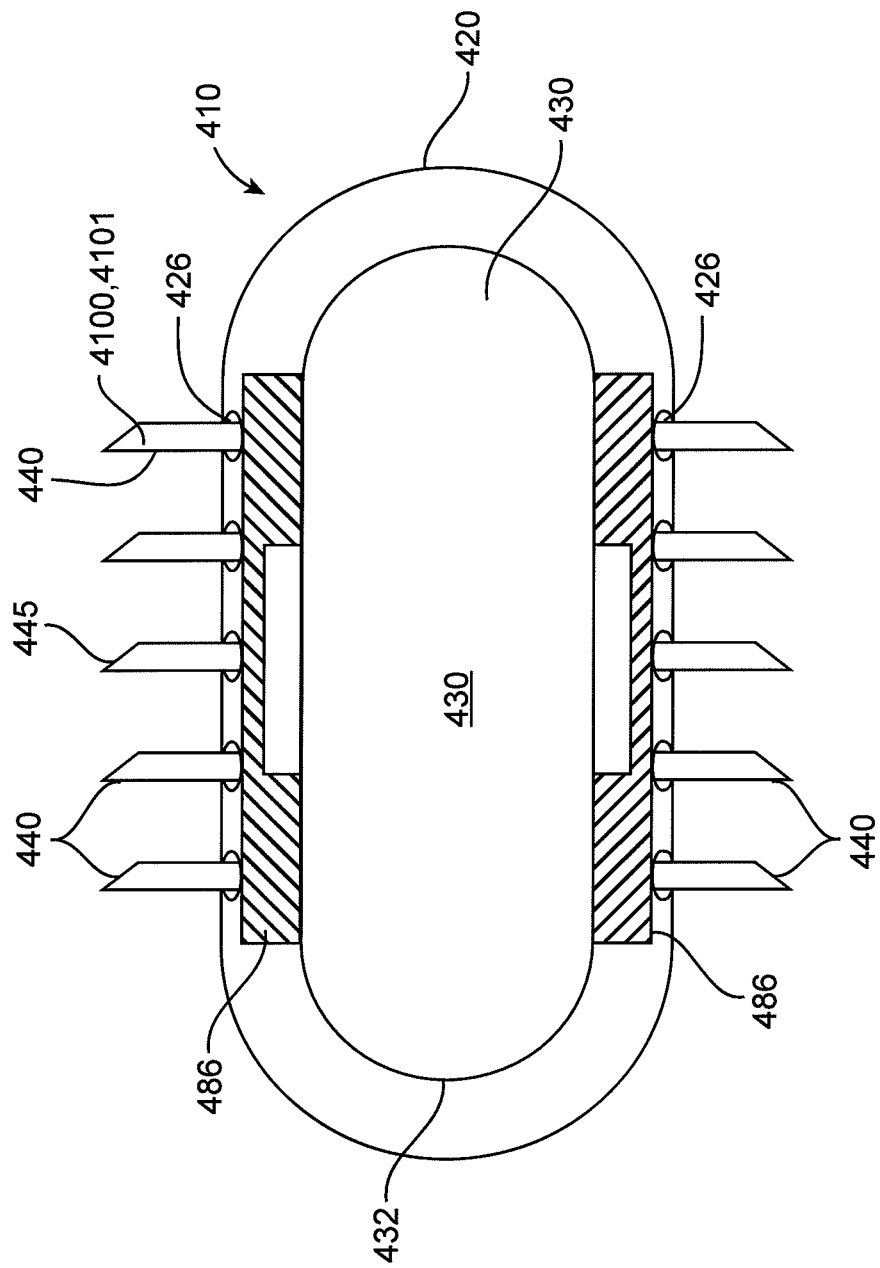

Also, platforms 486 can be placed on either side of balloon 430 to allow for bilateral deployment of tissue penetrating members 440 into intestinal wall IW as is shown in the embodiment of FIGS. 23*a* and 23*b*. In addition to delivering more drug, bilateral deployment serves to anchor capsule 420 on both sides of the intestinal wall IW during deployment of penetrating members 440, thus reducing the likelihood of the capsule from being dislodged during deployment (e.g., due to peristaltic contraction). In these and related embodiments tissue penetrating members 440 can be directly coupled to platform 486 without necessarily using advancement members 480*a*. Desirably, both advancement members 480 and platform 486 are constructed from biodegradable materials such as PGLA, which can be cross linked and/or copolymerized with to have increased rigidity to support the advancement of penetrating members 440 into tissue.

As an additional or alternative embodiment to the use of advancement member 480*a* and/or platform 468, tissue penetrating members 440 may be directly coupled to the balloon 430, e.g., by an adhesive where the adhesive force is less than the necessary to pull penetrating member out of tissue once it is deployed into the intestinal wall. In these and related embodiments, the tissue penetrating members 440 may also be configured to tear the balloon wall 432 when they detach from the balloon and thus provide a means for balloon deflation.

In various embodiments, penetrating members 440 can carry the same or a different drug 4101 or other therapeutic agent. The former configuration allows for the delivery of greater amounts of a particular drug 4101, while the later, allows two or more different drugs to be delivered into the intestinal wall at about the same time to facilitate drug treatment regimens requiring substantial concurrent delivery of multiple drugs.

Figure 24A:
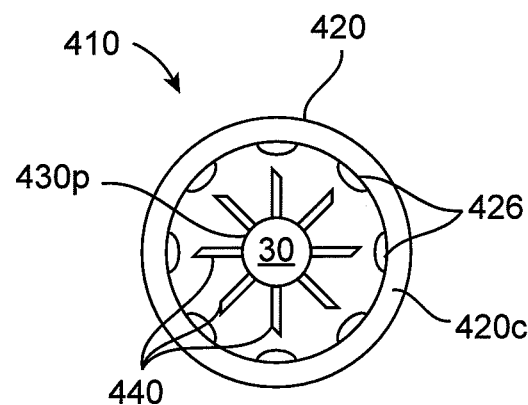
FIGS. 24a and 24b are cross sectional views illustrating use of an embodiment of a swallowable device having tissue penetrating members distributed around the entire perimeter of the balloon.
Figure 24B:
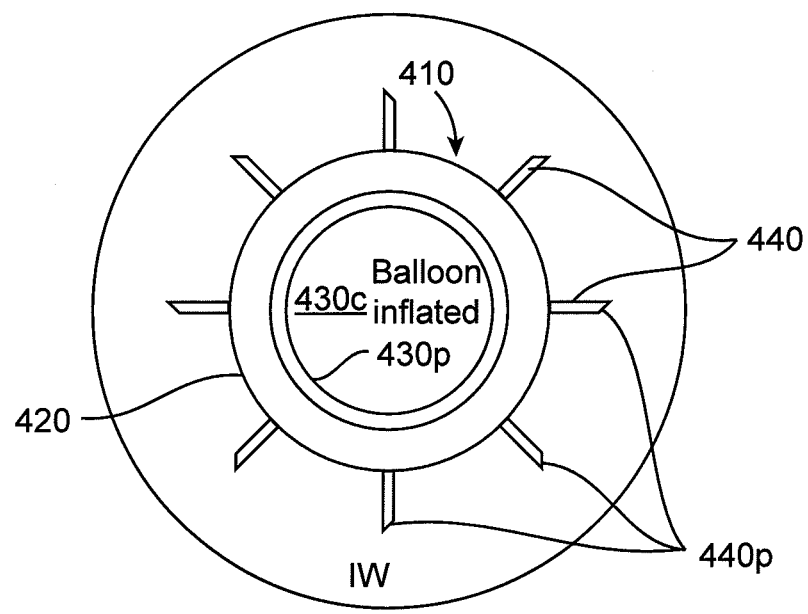

In various embodiments, depending upon the drug and associated drug regimen (e.g., dose and times per day, etc), tissue penetrating members 440 can be placed and distributed in a number of locations and patterns on the balloon surface. As described above for the embodiments of FIGS. 23*a* and 23*b*, tissue penetrating members 440 can be placed on opposite sides of balloon surface 438 so that balloon inflation can place tissue penetrating members 440 on opposite sides of the intestinal wall IW. Referring now to FIGS. 24*a*-24*b*, in other embodiments, tissue penetrating members 440 can be symmetrically or otherwise distributed around substantially the entire perimeter 430*p* of the balloon 430 or other expandable member 430 as is shown in the embodiments of FIGS. 24*a* and 24*b*. In use, such embodiments not only anchor capsule 420 into the intestinal wall IW (as described above for bidirectional deployment) but also place tissue penetrating members 440 in a distributed pattern 440*p* around the circumference of the intestinal wall IW. Embodiments of the invention utilizing such a distributed delivery of drug into the intestinal wall can achieve the following: i) allow for additional amounts of a particular drug to be delivered; and ii) provide for faster absorption of the drug into the blood stream due to a more even distribution of the drug within the intestinal wall (e.g., due to placement of the tissue penetrating members within a larger volume of intestinal vascular for mass transfer and absorption into the blood).

Figure 25A:
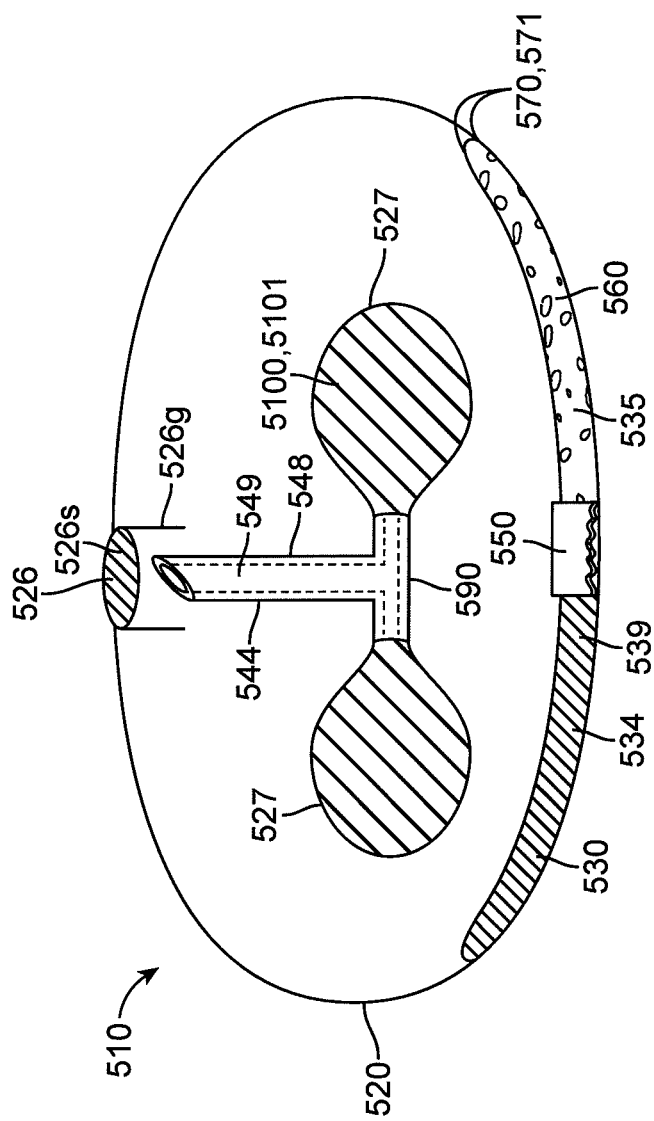
FIGS. 25a and 25b are lateral views illustrating use of an embodiment of a swallowable device having drug reservoirs compressible by expansion of the inflatable balloon.
Figure 25B:
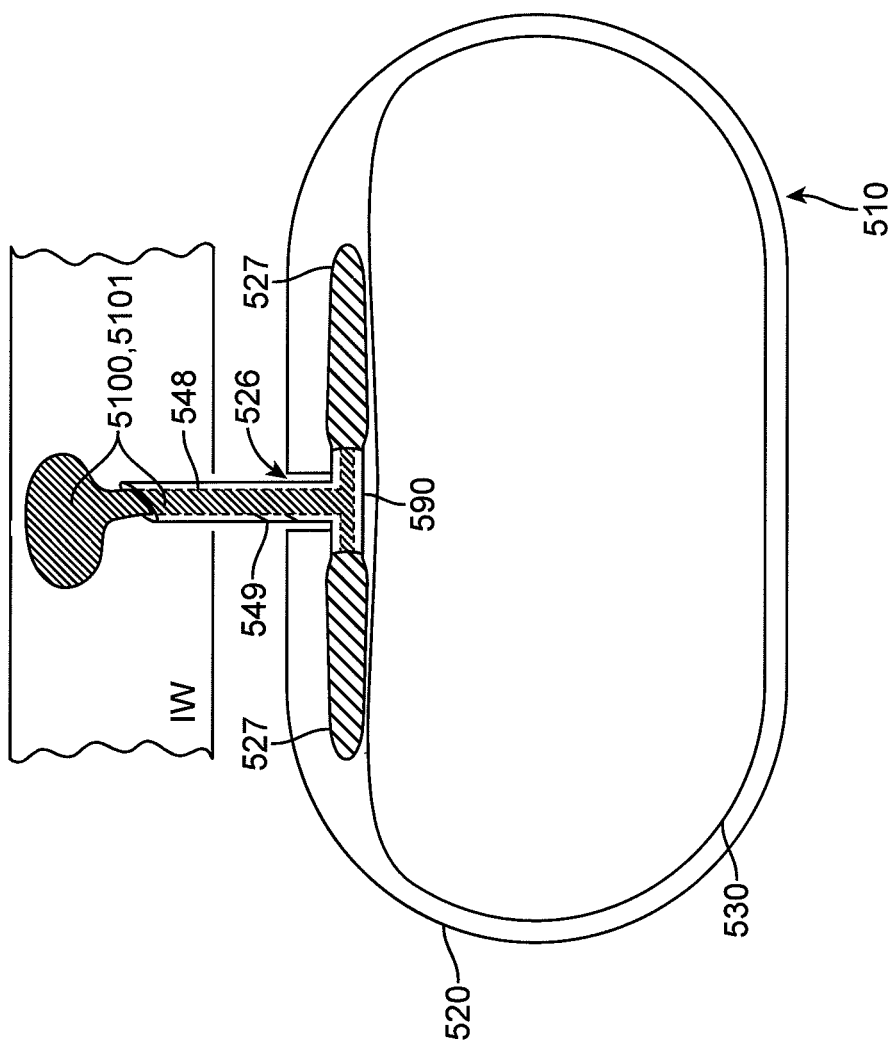
Figure 26:
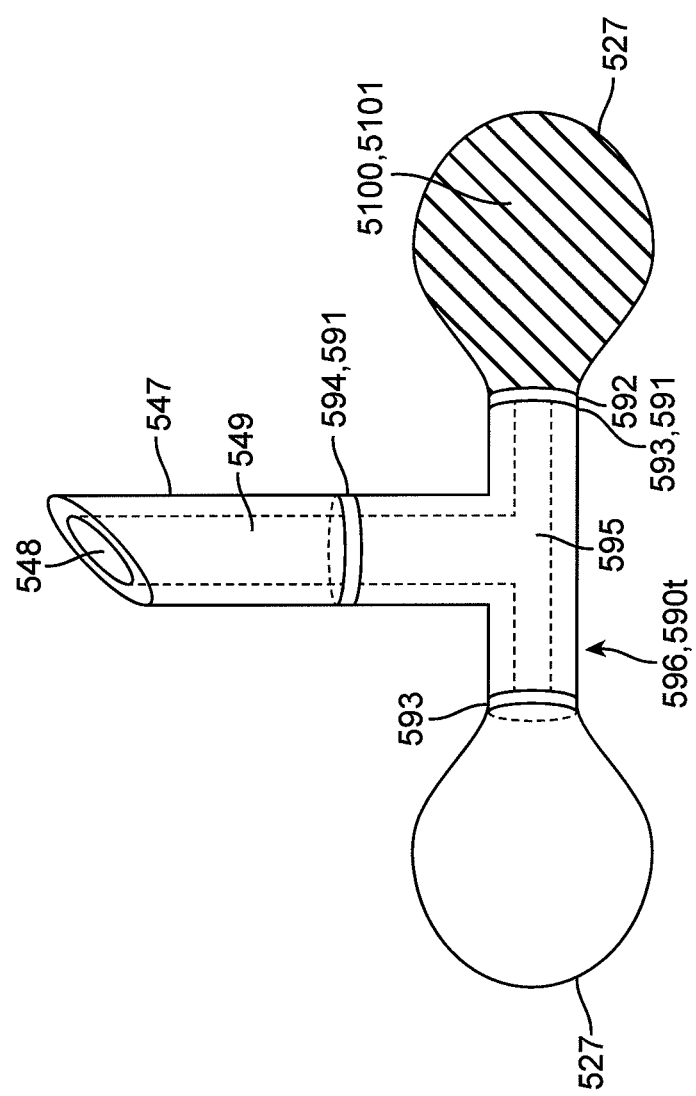
FIG. 26 is a lateral view illustrating an embodiment of a manifold for coupling two or more drug reservoirs to a hollow tissue penetrating member.

As described herein, many embodiments of device 510 include a drug carrying tissue penetrating member 540 as a means for delivering drug or other therapeutic agent 5101 into the intestinal wall. Referring now to FIGS. 25a-25b and 26, as an alternative or additional means for delivering drug into the intestinal wall, in various embodiments, device 510 can also be configured to inject drug 5101 into the intestinal wall by means of hollow tissue penetrating members 548 coupled to one or more drug reservoirs 527. Hollow tissue penetrating members 548 include at least one lumen 549. Reservoirs 527 are desirably compressible by expansion of the balloon or other expandable member 530 and can thus comprise various biodegradable elastic polymers. The reservoirs 527 can contain drug or other therapeutic agent 5101 in liquid or powder form. For liquid form, the drug will be dissolved in an aqueous drug solution 5104. In these and related embodiments, reservoirs 527 are fluidically coupled to hollow tissue penetrating members 548 such that inflation of balloon 530 compresses the reservoirs 527 so as to force the drug solution 5104 through tissue penetrating member lumen 549 and into the intestinal wall as is shown in FIGS. 25a and 25b. In these and related embodiments apertures 526, can include a guide tube 526g, which is horizontally aligned with the tip 544 of penetrating member 548 and configured to guide the advancement of penetrating member 548 out of capsule 520 and into the intestinal wall. Multiple reservoirs 527 are contemplated including two, three, four or more. In particular embodiments, two reservoirs 527 can be coupled to a hollow tissue penetrating member with the reservoirs placed about 180 degrees apart with respect to penetrating member shaft 544. Typically, the reservoirs 527 will be fluidically coupled to the hollow penetrating member 548 by means of a manifold 590. Suitable manifolds 590 include a t-shaped manifold 590t having connectors 592 on either of its lateral ends 593 for connection to reservoirs 527 and a central connector 594 for connection to hollow tissue penetrating member 547 and a central lumen or channel 595 going to all connectors 591 (FIG. 16). Other shapes and manifold configurations are also contemplated, for example, Y-shaped (connecting two reservoirs to tissue penetrating member 548).

In some embodiments, balloon 30 or other expandable member 30 can be expanded responsive to a sensor 67, such as a pH sensor 68 or other chemical sensor which detects the presence of the capsule in the small intestine. Sensor 67 (FIG. 1b) can then send a signal to a controllable embodiment of isolation valve 50 or to an electronic controller 28c coupled to a controllable isolation valve 50 to open and thus expand balloon 30 as is described herein. Embodiments of a pH sensor 68 can comprise an electrode-based sensor or it can be a mechanically-based sensor such as a polymer which shrinks or expands upon exposure to a selected pH or other chemical conditions in the small intestine. In related embodiments, an expandable/contractable sensor 67 can also comprise the actuating mechanism 60 itself by using the mechanical motion from the expansion or contraction of the sensor.

Figure 27A:
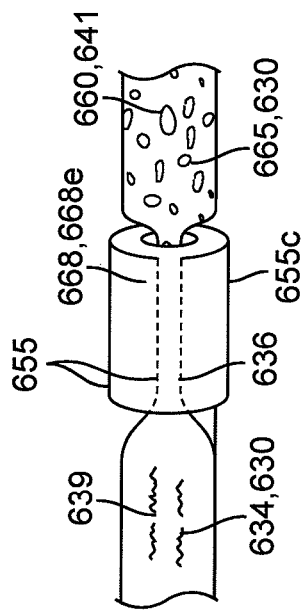
FIGS. 27a and 27b shows an embodiment of a colar type separation valve incorporating use of an expandable pH sensor for opening of the valve.
Figure 27B:
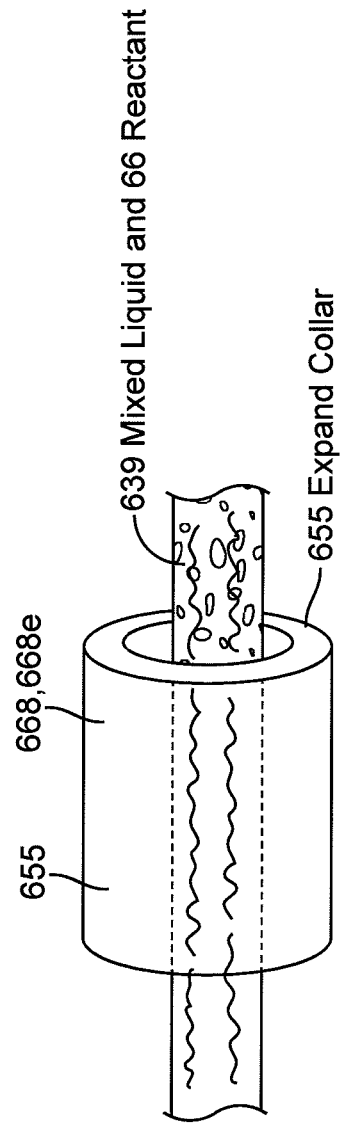
Figure 28A:
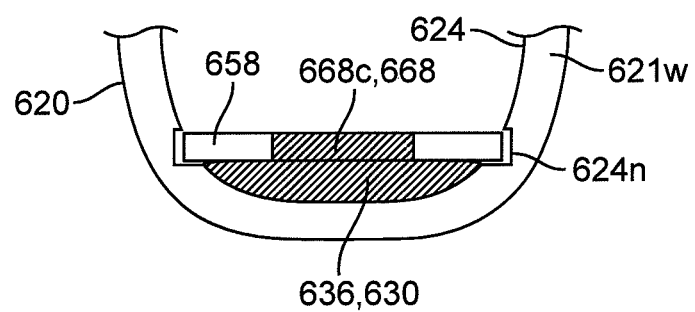
FIGS. 28a-28b are cross sectional views of an embodiment of a beam like separation valve incorporating use of a contractible pH sensor for opening of the valve.
Figure 28B:
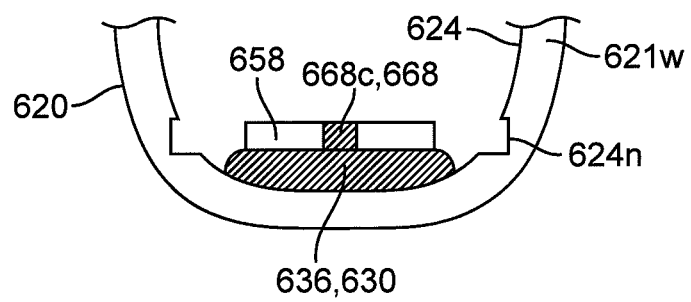

Referring now to FIGS. 27a-27b and 28a-28b, in related embodiments, an expandable/contractible pH sensor 668 can also comprise the isolation valve 650 itself, by configuring the sensor to expand or contract so as to open a channel between balloon compartments 634 and 635. According to one embodiment for such an approach, a pH sensor 668 may be integrated into a collar valve 655 where sensor 668 comprises all or a portion of a collar 655c that is placed over connecting portion 636 of balloon 630 (FIGS. 27a and 27b). In this embodiment, sensor 668 would be an expandable sensor 668e, configured to expand upon exposure to the pH conditions in the small intestine (e.g., a pH above 6.0, 6.5, 7.0, 7.1, 7.2, etc) so as to either have the collar come off or significantly loosen collar 655c enough to allow contents of compartments 634 and 635 to mix. According to another embodiment shown in FIGS. 28a and 28b, a pH sensor 668 could be integrated into a beam valve 658 described herein, where the beam is under compressive load by being snap fit against the capsule interior surface 624. The beam applies a portion of this compressive load onto balloon connecting section 636 so as to maintain the seal between compartments 634 and 635. In this case, sensor 668 would be a contractible sensor 668c configured to open valve 650 by contracting upon exposure to higher pH in the intestine, so that the beam shortens sufficiently so that it falls out of place against capsule surface 624 or other wise no longer applies a compressive load sufficient to maintain a seal over balloon connecting section 636.

According to another embodiment for detecting when the device is in the small intestine (or other location in the GI tract), sensor 67 can comprise pressure/force sensor such as strain gauge for detecting the number of peristaltic contractions that capsule 20 is being subject to within a particular location in the intestinal tract (in such embodiments capsule 20 is desirably sized to be gripped by the small intestine during a peristaltic contraction). Different locations within the GI tract have different number of peristaltic contractions. The small intestine has between 12 to 9 contractions per minute with the frequency decreasing down the length of the intestine. Thus, according to one or more embodiments, detection of the number of peristaltic contractions can be used to not only determine if capsule 20 is in the small intestine, but the relative location within the intestine as well. In use, these and related embodiments allow for release of medication 100 at a particular location in the small intestine.

As an alternative or supplement to internally activated drug delivery (e.g., using a release element and/or sensor), in some embodiments, the user may externally send a signal to expand balloon 30 or other expandable member 30 to activate the actuating mechanism 60 to deliver medication 100 by means of RF, magnetic or other wireless signaling means known in the art. In various embodiments, including those with reference to FIG. 1b, external activation can be achieved by use of a controllable isolation valve 50 for example, a radio frequency (RF) controlled miniature solenoid valve or other electro-mechanical control valve (not shown). In other embodiments, a controllable isolation valve 50 may correspond to a miniature magnetically valve such as a magnetically controlled miniature reed switch (not shown). Such electromechanical or magnetic-based valves can be fabricated using MEMS and other micro-manufacturing methods. In these and related embodiments, the user can use a handheld communication device 13 (e.g., a hand held RF device such as a cell phone) as is shown in the embodiment of FIG. 1b, to send a receive signals 17 from device 10. In such embodiments, swallowable device may include a transmitter 28 such as an RF transceiver chip or other like communication device/circuitry. Handheld device 13 may not only includes signaling means, but also means for informing the user when device 10 is in the small intestine or other location in the GI tract. The later embodiment can be implemented through the use of logic resources 29 (e.g., a processor 29) coupled to transmitter 28 to signal to detect and singe to the user when the device is in the small intestine or other location (e.g., by signaling an input from the sensor). Logic resources 29 may include a controller 28c (either in hardware or software) to control one or more aspects of the process. The same handheld device can also be configured to alert the user when balloon 30 or actuating mechanism 60 has been expanded or activated (respectively) and the selected medication 100 delivered (e.g., using processor 29 and transmitter 28). In this way, the user is provided confirmation that medication 100 has been delivered. This allows the user to take other appropriate drugs/ therapeutic agents as well as make other related decisions (e.g., for diabetics to eat a meal or not and what foods should be eaten). The handheld device can also be configured to send a signal to swallowable device 10 to over-ride isolation valve 50 or actuating mechanism 60 and so prevent delay or accelerate the delivery of medication 100. In use, such embodiments allow the user to intervene to prevent, delay or accelerate the delivery of medication, based upon other symptoms and/or patient actions (e.g., eating a meal, deciding to go to sleep, exercise etc). The user may also externally expand balloon 30 or activate actuating mechanism 60 at a selected time period after swallowing the capsule. The time period can be correlated to a typical transit time or range of transit times for food moving through the user's GI tract to a particular location in the tract such as the small intestine.

Figure 10:
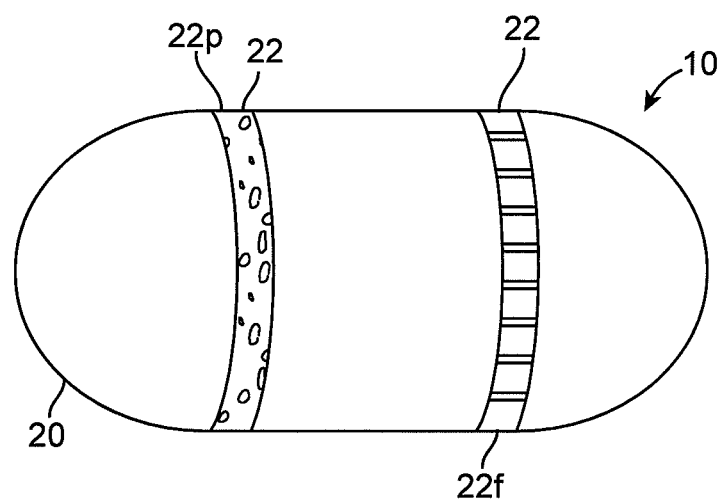
FIG. 10 shows an embodiment of a capsule having biodegradable seams including pores and/or perforations to accelerate biodegradation of the capsule.
Figure 11:
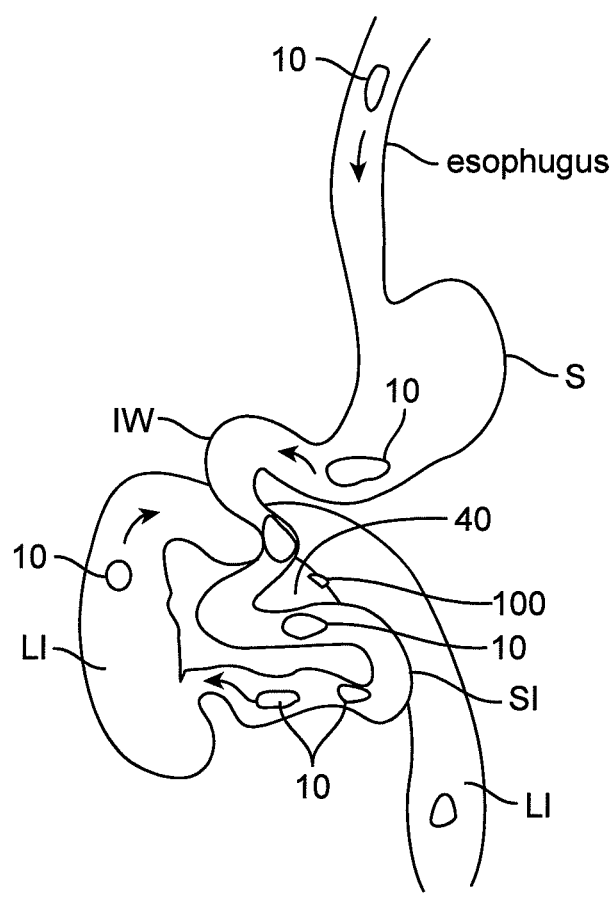
FIG. 11 is a lateral viewing illustrating use of an embodiment of a swallowable drug delivery device including transit of device in the GI tract and operation of the device to deliver drug.
Figure 12:
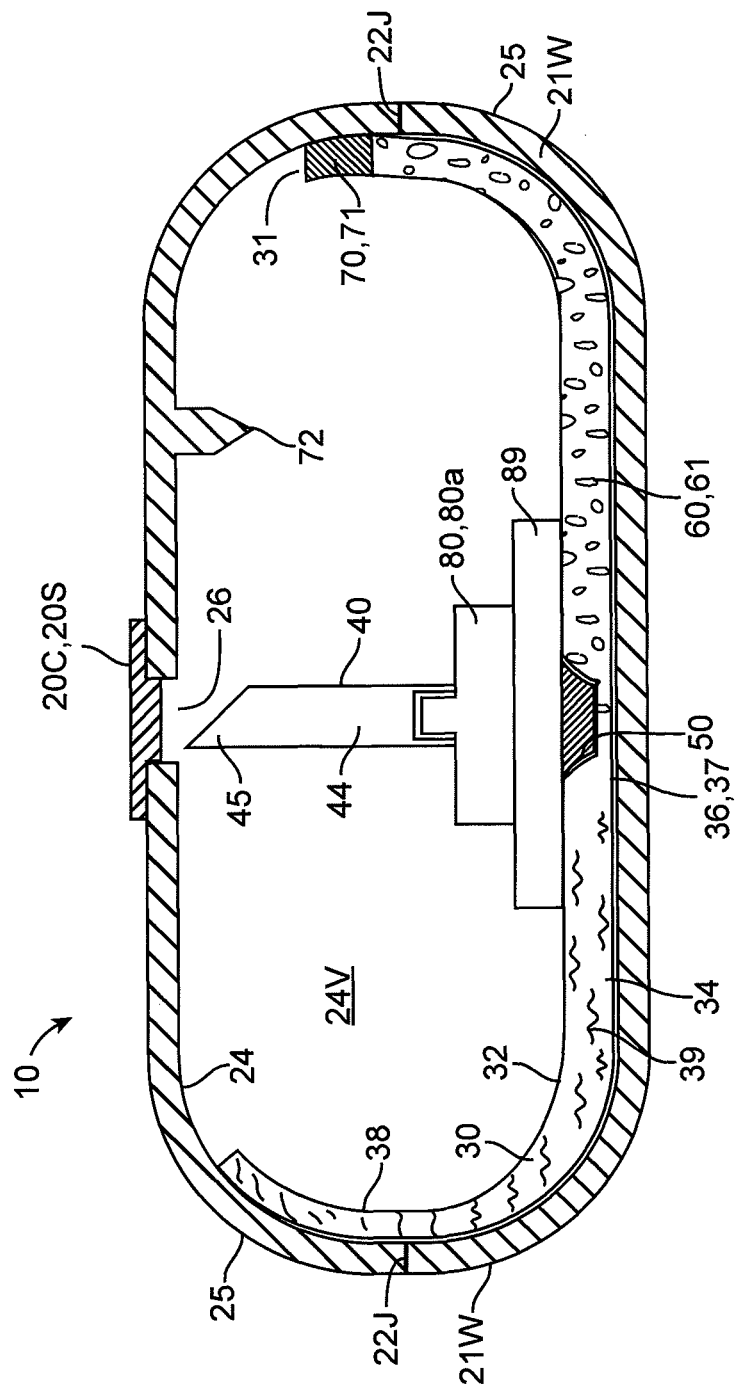
FIG. 12 is a lateral cross sectional view illustrating an embodiment of the swallowable drug device having an expandable member such as an expandable balloon.
Figure 13:
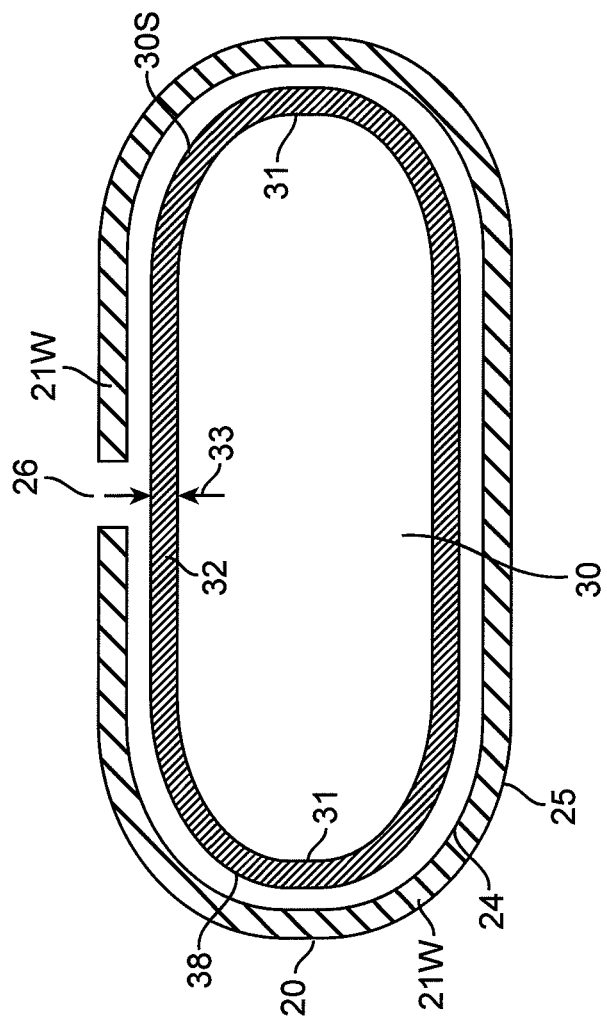
FIG. 13 is a lateral view illustrating an embodiment of an expandable balloon in an inflated state inside an embodiment of the swallowable capsule
Figure 30:
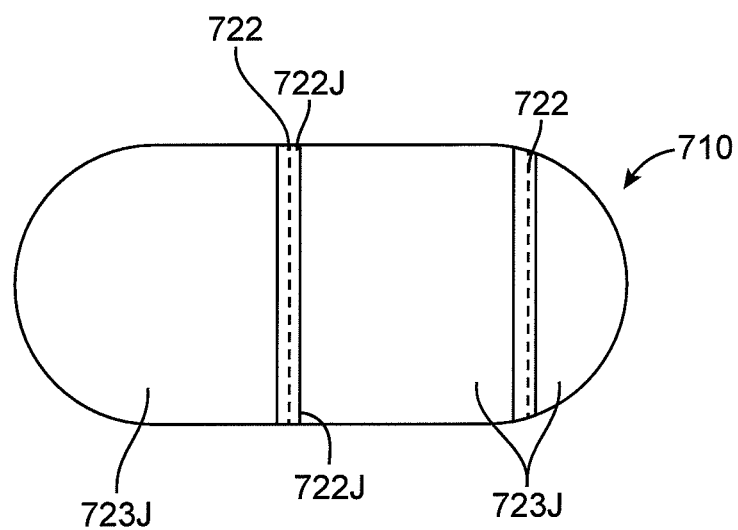
FIG. 30 shows an embodiment of a balloon tearable capsule fabricated from separate portions joined by seams, which can be torn by inflation of the expandable balloon.

Referring now to FIGS. 29a-29b and 30, in various embodiments, the capsule 720 can include seams 722 of biodegradable material which controllably degrade to produce capsule pieces 723 of a selectable size and shape to facilitate passage through the GI tract as is shown in the embodiment of FIGS. 11, 29a and 29b, for example. Seams 722 can also include pores or other openings 722p for ingress of fluids into the seam to accelerate biodegradation as is shown in the embodiment of FIG. 10. Other means for accelerating biodegradation of seams 722 can include pre-stressing the seam and/or including perforations 722f in the seam (FIG. 10). In still other embodiments, seam 722 can be constructed of materials and/or have a structure which is readily degraded by absorption of ultrasound energy, e.g. high frequency ultrasound (HIFU), allowing the capsule to be degraded into smaller pieces using externally or endoscopically (or other minimally invasive method) administered ultrasound.

Referring now to FIGS. 29a-29b and 30, in many embodiments seams 722 can also be configured and arranged so as to allow capsule 720 to be broken into smaller pieces by the inflation of balloon 730 or other expandable member 730. In particular embodiments, seams 722 can be oriented with respect to capsule radial perimeter 721, including having a radial pattern 722rp so as to have the capsule break into halves or other fractional pieces along its perimeter. Seams 722 may also be longitudinally-oriented with respect to capsule lateral access 720la to have the capsule break up into lengthwise pieces.

As alternative or additional approach for breaking up capsule 720 by balloon inflation (or expansion of other expandable member 730), capsule 720 can be fabricated from two or more separate joinable pieces 723j (e.g., radial halves) that are joined at a joint 722j formed by seams 722 (which function as an adhesive joint) as shown in the embodiment of FIG. 30. Alternatively, joinable pieces 723j may be merely joined by a mechanical fit such as a snap or press fit.

Suitable materials for seams 722 can include one or more biodegradable materials described herein such as PGLA, glycolic acid etc. Seams 722 can be attached to capsule body 720 using various joining methods known in the polymer arts such as molding, hot melt junctions, etc. Additionally for embodiments of capsule 720 which are also fabricated from biodegradable materials, faster biodegradation of seam 722 can be achieved by one or more of the following: i) fabricating the seam from a faster biodegrading material, ii) pre-stressing the seam, or iii) perforating the seam. The concept of using biodegradable seams 722 to produce controlled degradation of a swallowable device in the GI tract can also be applied to other swallowable devices such as swallowable cameras (or other swallowable imaging device) to facilitate passage through the GI tract and reduce the likelihood of such a device becoming stuck in the GI tract. Accordingly, embodiments of biodegradable seam 722 can be adapted for swallowable imaging and other swallowable devices.

In still other embodiments, seam 722 can be constructed of materials and/or have a structure which is readily degraded by absorption of ultrasound energy, e.g. high frequency ultrasound (HIFU), allowing the capsule to be degraded into smaller pieces using externally or endoscopically (or other minimally invasive method) administered ultrasound.

Another aspect of the invention provides methods for the delivery of drugs and other therapeutic agents (in the form of medication 100) into the walls of the GI tract using one or more embodiments of swallowable drug delivery device 10. An exemplary embodiment of such a method will now be described. The described embodiment of drug delivery occurs in the small intestine SI. However, it should be appreciated that this is exemplary and that embodiments of the invention can be used for delivering drug in a number of locations in the GI tract including the stomach and the large intestine. For ease of discussion, the swallowable drug delivery device 10 will sometimes be referred to herein as a capsule. As described above, in various embodiments device 10 may be packaged as a kit 11 within sealed packaging 12 that includes device 10 and a set of instructions for use 15. If the patient is using a handheld device 13, the patient may instructed to enter data into device 13 either manually or via a bar code 18 (or other identifying indicia 18) located on the instructions 15 or packaging 12. If a bar code is used, the patient would scan the bar code using a bar code reader 19 on device 13. After opening packaging 12, reading the instructions 15 and entering any required data, the patient swallows an embodiment of the swallowable drug delivery device 10. Depending upon the drug, the patient may take the device 10 in conjunction with a meal (before, during or after) or a physiological measurement such as a blood glucose measurement. Capsule 20 is sized to pass through the GI tract and travels through the patient's stomach S and into the small intestine SI through peristaltic action as is shown in the embodiment of FIG. 11. Once the capsule 10 is in the small intestine, the release element 70 is degraded by the basic pH in the small intestine (or other chemical or physical condition unique to the small intestine) so as expand balloon 30 or other expandable member 30, actuate the actuating mechanism 60 and deliver medication 100 into the wall of the small intestine SI according to one or more embodiments of the invention. For embodiments including a hollow needle or other hollow tissue penetrating member 40, medication delivery is effectuated by using balloon 30 the actuating mechanism 60 to advance the needle 40 a selected distance into the mucosa of the intestinal wall IS, and then the medication is injected through the needle lumen by advancement of the delivery member 50. The delivery member 50 is withdrawn and the needle 40 is then withdrawn back within the body of the capsule (e.g. by recoil) detaching from the intestinal wall. For embodiments of device 10 having multiple needles, a second or third needle 42, 43 can also be used to deliver additional doses of the same drug or separate drugs 101. Needle advancement can be done substantially simultaneously or in sequence. In preferred embodiments that use multiple needles, needle advancement can be done substantially simultaneously so as to anchor device 10 in the small intestine during drug delivery.

Figure 9A:
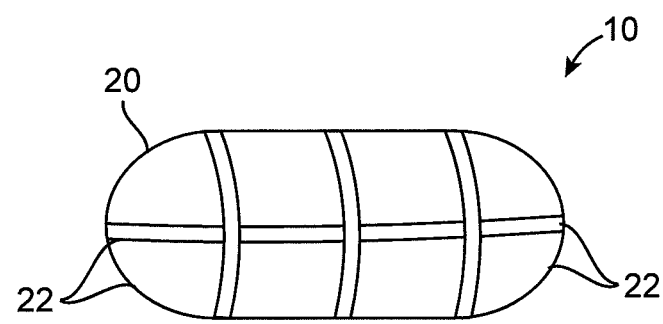
FIG. 9a shows an embodiment of a swallowable drug delivery device including a capsule having bio-degradable seams positioned to produce controlled degradation of the capsule in the GI tract.
Figure 9B:
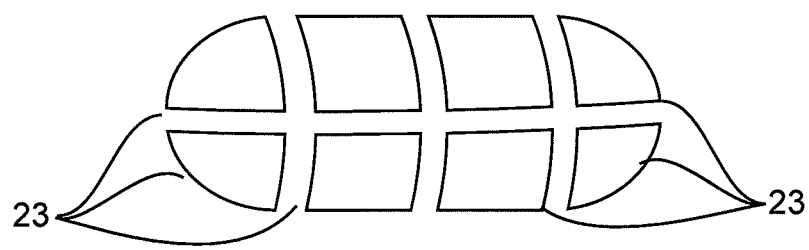
FIG. 9b shows the embodiment of FIG. 9a after having been degraded in the GI tract into smaller pieces.

After medication delivery, device 10 then passes through the intestinal tract including the large intestine LI and is ultimately excreted. For embodiments having a tearable capsule, the capsule may immediately be broken into smaller pieces by inflation of balloon 30. For embodiments of the capsule 20 having biodegradable seams 22 or other biodegradable portions, the capsule is degraded in the intestinal tract into smaller pieces, to facilitate passage through and excretion from the intestinal tract as is shown in the embodiments of FIGS. 9a and 9b. In particular embodiments having biodegradable tissue penetrating needles/members 40, should the needle get stuck in the intestinal wall, the needle biodegrades releasing the capsule 20 from the wall.

For embodiments of device 10 including a sensor 67, can be effectuated by the sensor sending a signal to a controllable embodiment of isolation valve 50 or actuating mechanism 60 and/or a processor 29/controller 28c coupled to the isolation valve 50 or actuating mechanism. For embodiments of device 10 including external actuation capability, the user may externally expand balloon 30 or activate actuating mechanism 60 at a selected time period after swallowing the capsule. The time period can be correlated to a typical transit time or range of transit times for food moving through the user's GI tract to a particular location in the tract such as the small intestine.

One or more embodiments of the above methods can be used for the delivery of preparations 100 containing therapeutically effective amounts of a variety of drugs and other therapeutic agents 101 to treat a variety of diseases and conditions. These include a number of large molecule peptides and proteins which would otherwise require injection and/or IV infusion due to chemical breakdown or other degradation of the compound by the digestive fluids in the stomach and/or the lumen of the small intestine. Such compounds which can be delivered with various embodiments of the invention can include without limitation, parathyroid hormones, growth hormones (e.g., IFG and other growth factors), insulin compounds, antibodies and other gamma globulin proteins (e.g., gamma globulin) interferons and other cytokines, glucagon like peptides e.g., (GLP-1, exenatide) and other incretins, chemotherapeutic agents (doxorubicin) and other like compounds. Embodiments of the invention allow these and other compounds to be delivered into the wall of the small intestine and subsequently absorbed into the blood stream with minimal or no loss of activity of the compound, e.g., in the case of an antibody, minimal or no loss in affinity and/or specificity to a target antigen; in the case of an interferon or other cytokine, minimal or no loss in an immune stimulating effect, in the case of insulin or GLP-1, minimal or no loss in glucose regulating ability; in the case of growth hormone, minimal or no loss in growth stimulating effect; in the case of a chemotherapeutic agent for the treatment of cancer, minimal or no loss in cancer treatment effect (e.g., a tumor necrosis, and/or reduced cell division); and in the case of any polypeptide, minimal or no loss in affinity and/or specificity to a target binding site. Suitable drugs and other therapeutic agents which can be delivered by embodiments of the invention include any number of orally delivered agents, antibiotics (vancomycin, penicillin, erythromycin, etc.), antivirals (protease inhibitors, anti-seizure compounds (fluosemide, dilatin), non-steroidal anti-inflamatory drugs (NSAIDS) such as ibuprofen), various chemotherapeutic agents (e.g., interferon), antibiotics, antivirals, insulin and related compounds, glucagon like peptides (e.g., GLP-1, exenatide), parathyroid hormones, growth hormones (e.g., IFG and other growth factors), anti-seizure agents (e.g., furosimide), anti-migraine medication (sumatriptan), immune suppression agents (e.g., cyclosporine) and anti-parasitic agents such as various anti-malarial agents. The dosage of the particular drug can be titrated for the patient's weight, age or other parameter. Embodiments of the invention also allow dosages of drug other therapeutic agent 101 to be advantageously adjusted for other factors as well. For example, for drugs that would otherwise be partially degraded or poorly absorbed in the GI tract, the amount or dose of drug 101 to achieve a desired or therapeutic effect (e.g., insulin for blood glucose regulation, furosimide for anti-seizure) can be less than the amount required should the drug have been delivered by conventional oral delivery (e.g., a swallowable pill that is digested in the stomach and absorbed through the wall of the small intestine). This is due to the fact that there is little or no degradation of the drug by acid and other digestive fluids in the stomach and the fact that all, as opposed to only a portion of the drug is delivered into the wall of the small intestine (or other lumen in the intestinal tract, e.g., large intestine, stomach, etc.). Depending upon the drug 101, the dose 102 delivered in preparation 100 can be in the range from 100 to 5% of a dose delivered by conventional oral delivery means (e.g., a formulated pill) to achieve a desired therapeutic effect (e.g., blood glucose regulation, seizure regulation, etc.) with even lower amounts contemplated. The particular dose reduction can be titrated based upon the particular drug, the condition to be treated, and the patient's weight, age and condition. For some drugs (with known levels of degradation in the intestinal tract) a standard dose reduction can be employed (e.g., 10 to 20%). Larger amounts of dose reduction can be used for drugs which are more prone to degradation in the GI tract and poor absorption. In this way, the potential toxicity (particularly to non target tissue sites) and other deleterious side effects (e.g., gastric cramping, diarrhea, irritable bowel, hemorrhage, etc.) of a particular drug or drugs delivered by device 10 can be reduced because the ingested dose is lowered and all or nearly all of the drug is delivered into the wall of the small intestine. This in turn, improves patient compliance because the patient has a reduction both in the severity and incidence of deleterious effects. Additional benefits of embodiments employ dose reduction of drug 101 that include a reduced likelihood for the patient to develop a tolerance to the drug (requiring higher doses) and, in the case of antibiotics or antivirals, for the patient to develop resistant strains of bacteria or viruses (e.g., resistance to the use of vancomycin by bacteria or to a protease inhibitor by the Aids virus). For the case of a chemotherapeutic agent for the treatment of cancer, the deleterious effect can comprise the development of resistance to the chemotherapeutic agent by cancer cells as well as toxicity to non-target tissue. For the case of an anti-seizure medication such as dilatin, the deleterious effects can include various neuromuscular conditions such as tremor, nystagmus, slurred speech, dizziness, memory and concentration problems as well conditions such as rash and bone loss. For anti-seizure and/or diuretics such as furesomide such deleterious effects can include various neuromuscular, vascular, gastro intestinal effects such as dizziness, low blood pressure, dehydration, nausea, loss of electrolytes, tinnitus and rash. Also, other levels of dose reduction can be achieved for patients who have undergone gastric bypass surgery and other procedures in which sections of the small intestine have been removed or its working (e.g., digestive) length otherwise effectively shortened. In these and related embodiments, levels of dose reduction can be achieved in the range of 25 to 50% or even greater and the patient need only take one dose of the drug versus multiple doses because of poor absorption issues. In still other embodiments, the dose of a particular orally delivered drug 101 can be increased because the various deleterious effects in the GI system (e.g., cramping, bleeding, etc.) are avoided since the drug or other therapeutic agent is injected directly into the wall of the small intestine. This increased dosage in turn allows for one or more of the following: fewer doses, faster treatment, faster obtainment of a therapeutic effective level of the drug in the blood stream, better control of blood concentrations and other pharmacokinetic parameters. In various embodiments, the dosage of a particular drug can increased in the range of 5 to 100% or higher. The amount of the increase can again be titrated based on the patient's, weight, age, condition and individual tolerance to the drug (which can be determined e.g., by using various biomarkers of tolerance and/or toxicity).

In addition to delivery of a single drug, embodiments of swallowable drug delivery device 10 and its methods of their use can be used to deliver a plurality of drugs for the treatment of multiple conditions or for the treatment of a particular condition (e.g., protease inhibitors for treatment HIV AIDS). In use, such embodiments allow a patient to forgo the necessity of having to take multiple medications for a particular condition or conditions. Also, they provide a means for facilitating that a regimen of two or more drugs is delivered and absorbed into the small intestine and thus, the blood stream, at about the same time. Due to difference in chemical makeup, molecular weight, etc, drugs can be absorbed through the intestinal wall at different rates, resulting in different pharmacokinetic distribution curves. Embodiments of the invention address this issue by injecting the desired drug mixtures at substantially the same time. This in turn, improves the pharmacokinetics and thus the efficacy of the selected mixture of drugs. Additionally, eliminating the need to take multiple drugs is particularly beneficial to patients who have one or more long term chronic conditions including those who have impaired cognitive or physical abilities.

In various applications, embodiments of the above methods can be used to deliver preparations 100 including drugs and therapeutic agents 101 to provide treatment for a number of medical conditions and diseases. The medical conditions and diseases which can be treated with embodiments of the invention can include without limitation: cancer, hormonal conditions (e.g., hypo/hyper thyroid, growth hormone conditions), osteoporosis, high blood pressure, elevated cholesterol and triglyceride, diabetes and other glucose regulation disorders, infection (local or septicemia), epilepsy and other seizure disorders, osteoporosis, coronary arrhythmia's (both atrial and ventricular), coronary ischemia anemia or other like condition. Still other conditions and diseases are also contemplated.

In many embodiments, the treatment of the particular disease or condition can be performed without the need for injecting the drug or other therapeutic agent (or other non-oral form of delivery such as suppositories) but instead, relying solely on the therapeutic agent(s) that is delivered into the wall of the small intestine or other portion of the GI tract. For example, diabetes or another glucose regulation disorder can be treated (e.g., by controlling blood glucose levels) solely through the use of insulin that is delivered into the wall of the small intestine without the need for the patient to ever inject insulin. Similarly, the patient need not take conventional oral forms of a drug or other therapeutic agent, but again rely solely on delivery into the wall of the small intestine using embodiments of the swallowable capsule. In other embodiments, the therapeutic agent(s) delivered into the wall of the small intestine can be delivered in conjunction with an injected dose of the agent(s). For example, the patient may take a daily dose of insulin or compound for blood glucose regulation using the embodiments of the swallowable capsule, but only need take an injected dose every several days or when the patient's condition requires it (e.g., hyperglycemia). The same is true for therapeutic agents that are traditionally delivered in oral form (e.g., the patient can take the swallowable capsule and take the conventional oral form of the agent as needed). The dosages delivered in such embodiments (e.g., the swallowed and injected dose) can be titrated as needed (e.g., using standard dose response curve and other pharmacokinetic methods can be used to determine the appropriate dosages). Also, for embodiments using therapeutic agents that can be delivered by conventional oral means, the dose delivered using embodiments of the swallowable capsule can be titrated below the dosage normally given for oral delivery of the agent since there is little or no degradation of the agent within the stomach or other portion of the intestinal tract (herein again standard dose response curve and other pharmacokinetic methods can be applied).

Various groups of embodiments of preparation 100 containing one or more drugs or other therapeutic agents 101 for the treatment of various diseases and conditions will now be described with references to dosages. It should be appreciated that these embodiments, including the particular therapeutic agents and the respective dosages are exemplary and the preparation 100 can comprise a number of other therapeutic agents described herein (as well as those known in the art) that are configured for delivery into a luminal wall in the intestinal tract (e.g., the small intestinal wall) using various embodiments of device 10. The dosages can be larger or smaller than those described and can be adjusted using one or more methods described herein or known in the art. In one group of embodiments, therapeutic agent preparation 100 can comprise a therapeutically effective dose of insulin for the treatment of diabetes and other glucose regulation disorders. The insulin can be human or synthetically derived as is known in the art. In one embodiment, preparation 100 can contain a therapeutically effective amount of insulin in the range of about 1-10 units (one unit being the biological equivalent of about 45.5 µg of pure crystalline insulin), with particular ranges of 2-4, 3-9, 4-9, 5-8 or 6-7. The amount of insulin in the preparation can be titrated based upon one or more of the following factors (herein, then "glucose control titration factors"): i) the patient's condition (e.g., type 1 vs. type II diabetes; ii) the patients previous overall level of glycemic control; iii) the patient's weight; iv) the patient's age; v) the frequency of dosage (e.g., once vs. multiple times a day); vi) time of day (e.g., morning vs. evening); vii) particular meal (breakfast vs. dinner); viii) content/glycemic index of a particular meal (e.g., meals having a high fat/lipid and sugar content (which tend to cause a rapid rise in blood sugar and thus have a higher glycemic index) vs. low fat and sugar content that do not (and thus have a lower glycemic index)); and ix) content of the patient's overall diet (e.g., amount of sugars and other carbohydrates, lipids and protein consumed daily).

In another group of embodiments, therapeutic agent preparation 100 can comprise a therapeutically effective dose of one or more incretins for the treatment of diabetes and other glucose regulation disorders. Such incretins can include Glucacon like peptides 1 (GLP-1) and their analogues, and Gastric inhibitory peptide (GIP). Suitable GLP-1 analogues include exenatide, liraglutide, albiglutide and taspoglutide as well as their analogues, derivatives and other functional equivalents. In one embodiment preparation 100 can contain a therapeutically effective amount of exenatide in the range of about 1-10 µg, with particular ranges of 2-4, 4-6, 4-8 and 8-10 µg respectively. In another embodiment, preparation 100 can contain a therapeutically effective amount of liraglutide in the range of about 1-2 mg (milligrams), with particular ranges of 1.0 to 1.4, 1.2 to 1.6 and 1.2 to 1.8 mg respectively. One or more of the glucose control titration factors can be applied to titrate the dose ranges for exenatide, liraglutide or other GLP-1 analogue or incretin.

In yet another group of embodiments, therapeutic agent preparation 100 can comprise a combination of therapeutic agents for the treatment of diabetes and other glucose regulation disorders. Embodiments of such a combination can include therapeutically effective doses of incretin and biguanide compounds. The incretin can comprise one or more GLP-1 analogues described herein, such as exenatide and the biguanide can comprise metformin (e.g., that available under the Trademark of GLUCOPHAGE® manufactured by Merck Santé S.A.S.) and its analogues, derivatives and other functional equivalents. In one embodiment, preparation 100 can comprise a combination of a therapeutically effective amount of exenatide in the range of about 1-10 µg and a therapeutically effective amount of metformin in a range of about 1 to 3 grams. Smaller and larger ranges are also contemplated with one or more of the glucose control titration factors used to titrate the respective dose of exenatide (or other incretin) and metformin or other biguanide. Additionally, the dosages of the exenatide or other incretin and metformin or other biguanide can be matched to improve the level of glucose control for the patient (e.g., maintenance of blood glucose within normal physiological levels and/or a reduction in the incidence and severity of instances of hyperglycemia and/or hypoglycemia) for extended periods of time ranging from hours (e.g., 12) to a day to multiple days, with still longer periods contemplated. Matching of dosages can also be achieved by use of the glucose control regulation factors as well as monitoring of the patient's blood glucose levels for extended periods using glycosylated hemoglobin (known as hemoglobin A1c, HbA1c, A1C, or Hb1c) and other analytes and measurements correlative to long term average blood glucose levels.

In still yet another group of embodiments, therapeutic agent preparation 100 can comprise a therapeutically effective dose of growth hormone for the treatment of one or more growth disorders, as well as wound healing. In one embodiment, preparation 100 can contain a therapeutically effective amount of growth hormone in the range of about 0.1-4 mg, with particular ranges of 0.1-1, 1-4, 1-2 and 2-4, with still larger ranges contemplated. The particular dose can be titrated based on one or more of the following: i) the particular condition to be treated and its severity (e.g., stunted growth, vs. wound healing); ii) the patient's weight; iii) the patient's age; and iv) the frequency of dosage (e.g., daily vs. twice daily).

In still yet another group of embodiments, therapeutic agent preparation 100 can comprise a therapeutically effective dose of parathyroid hormone for the treatment osteoporosis or a thyroid disorder. In one embodiment, preparation 100 can contain a therapeutically effective amount of parathyroid hormone in the range of about 1-40 µg, with particular ranges of 10-20, 20-30, 30-40 and 10-40 µg, with still larger ranges contemplated. The particular dose can be titrated based on one or more of the following: i) the particular condition to be treated and its severity (e.g., the degree of osteoporosis as determined by bone density measurements); ii) the patient's weight; iii) the patient's age; and iv) the frequency of dosage (e.g., daily vs. twice daily).

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the device can be sized and otherwise adapted for various pediatric and neonatal applications as well as various veterinary applications. Also those skilled in the art will recognize, or be able to ascertain using no more than routine experimentation, numerous equivalents to the specific devices and methods described herein. Such equivalents are considered to be within the scope of the present invention and are covered by the appended claims below.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for delivering a therapeutic agent into the wall of a small intestine of a patient, the method comprising:
    swallowing a drug delivery device comprising a release element and a solid therapeutic agent shaped as a tissue penetrating member configured to be inserted into the wall of a small intestine;
    wherein the solid therapeutic agent would chemically degrade if released within a lumen of the gastrointestinal tract;
    wherein the release element releases the solid therapeutic agent from the device into the wall of the small intestine responsive to a condition in the small intestine; and
    wherein the solid therapeutic agent penetrates into the wall of the small intestine such that the chemical degradation of the therapeutic agent in the lumen is inhibited.

2. The method of claim 1, wherein a dose of the therapeutic agent in the capsule does not include an amount to compensate for chemical degradation and/or lack of absorption of the therapeutic agent in the gastrointestinal tract.

3. The method of claim 1, wherein the dose of therapeutic agent is reduced in an amount between about 10 to 50 percent compared to a standard oral dosage.

4. The method of 1, wherein the patient has a shortened section of small intestine and a dose of the therapeutic agent in the capsule does not include a portion to compensate for lack of absorption of the therapeutic agent in the small intestine.

5. The method of claim 1, wherein the deleterious effect comprises one of gastric cramping, diarrhea, irritable bowel or hemorrhage within the GI tract.

6. The method of claim 1, wherein the deleterious effect comprises a toxic effect on non-target tissue.

7. The method of claim 1, wherein the therapeutic agent comprises a chemotherapeutic agent for the treatment of cancer and the deleterious effect comprises at least one of a toxic effect on non-target tissue or the development of resistance to the therapeutic agent by cancerous tissue within the patient.

8. The method of claim 1, wherein the therapeutic agent comprises an antibiotic and the deleterious effect comprises the development of bacterial resistance to the antibiotic.

9. The method of claim 1, wherein the therapeutic agent comprises an antiviral agent and the deleterious effect comprises the development of a viral resistance to the antiviral agent.

10. The method of claim 1, wherein the therapeutic agent comprises an anti-seizure compound and the deleterious effect comprises a neuromuscular, cardiovascular or gastrointestinal effect.

11. The method of claim 10, wherein the therapeutic agent comprises furosemide.

12. The method of claim 1, wherein the therapeutic agent comprises an antibody that is chemically degraded in the GI tract and the agent is delivered into the wall of the small intestine with minimal or no loss in the binding affinity or specificity to a target antigen site.

13. The method of claim 1, wherein the therapeutic agent comprises a polypeptide that is chemically degraded in the GI tract and the agent is delivered into the wall of the small intestine with minimal or no loss in binding affinity or specificity to a target binding site.

14. The method of claim 1, wherein the therapeutic agent comprises a cytokine or interferon that is chemically degraded in the GI tract and the agent is delivered into the wall of the small intestine with minimal or no loss in immune stimulating ability.

15. The method of claim 1, wherein the therapeutic agent comprises growth hormone that is chemically degraded in the GI tract and the agent is delivered into the wall of the small intestine with minimal or no loss in growth stimulating effect.

16. The method of claim 1, wherein the therapeutic agent comprises a chemotherapeutic agent for the treatment of cancer that is chemically degraded in the GI tract and the agent is delivered into the wall of the small intestine with minimal or no loss in cancer treatment effect.

17. The method of claim 1, wherein the therapeutic agent comprises a glucose regulating agent that is chemically degraded in the GI tract and the agent is delivered into the wall of the small intestine with minimal or no loss in glucose regulating ability.

18. The method of claim 17, wherein the glucose regulating agent comprises an insulin compound.

19. The method of claim 17, wherein the glucose regulating agent comprises an incretin compound, a GLP-1 compound or exenatide.

20. The method of claim 1, wherein the condition in the small intestine is a pH above about 7.1.

21. The method of claim 1, wherein the release element degrades in response to a chemical condition in the small intestine.

22. The method of claim 21, wherein the condition is a selected pH.

23. The method of claim 1, wherein the release element comprises an enteric material.

24. The method of claim 1, further comprising:
delivering a first therapeutic agent and a second therapeutic agent, wherein the first therapeutic agent is delivered using a first tissue penetrating member and the second therapeutic agent is delivered using a second tissue penetrating member.

25. A method of drug delivery, the method comprising, swallowing a drug delivery device comprising a capsule, a drug shaped as a tissue penetrating member configured to be inserted into a wall of the small intestine an actuating mechanism, and a release element; releasing the release element in the small intestine responsive to a condition in the small intestine; and actuating the actuation mechanism to deliver the drug into the wall of the small intestine by inserting the tissue penetrating member into the wall of the small intestine.

26. The method of claim 25, wherein the drug comprises a chemotherapeutic agent, interferon, an antibody, an antibiotic, growth hormone, parathyroid hormone, a glucose regulating agent, an insulin compound, an incretin hormone, a GLP-1 compound or exenatide.

27. The method of claim 25, wherein the release element degrades in response to a chemical condition in the small intestine.

28. The method of claim 25, wherein the release element comprises an enteric material.

29. The method of claim 25, wherein the actuating mechanism comprises a spring, a cam, an electromechanical mechanism, a solenoid, or a piezoelectric material.

* * * * *